US011845793B2

United States Patent
Waldmeier et al.

(10) Patent No.: US 11,845,793 B2
(45) Date of Patent: Dec. 19, 2023

(54) ANTI-ROR1 ANTIBODIES

(71) Applicant: NBE-THERAPEUTICS AG, Basel (CH)

(72) Inventors: Lorenz Waldmeier, Basel (CH); Ulf Grawunder, Hersberg (CH); Roger Beerli, Adlikon bei Regensdorf (CH)

(73) Assignee: NBE-THERAPEUTICS AG, Basel (CH)

( * ) Notice: Subject to any disclaimer, the term of this patent is extended or adjusted under 35 U.S.C. 154(b) by 129 days.

(21) Appl. No.: 15/768,235

(22) PCT Filed: Oct. 31, 2016

(86) PCT No.: PCT/EP2016/076244
§ 371 (c)(1),
(2) Date: Apr. 13, 2018

(87) PCT Pub. No.: WO2017/072361
PCT Pub. Date: May 4, 2017

(65) Prior Publication Data
US 2019/0153092 A1    May 23, 2019

(30) Foreign Application Priority Data
Oct. 30, 2015   (EP) ..................... 15192446

(51) Int. Cl.
| | |
|---|---|
| *C07K 16/28* | (2006.01) |
| *A61K 47/68* | (2017.01) |
| *A61K 31/704* | (2006.01) |
| *A61K 39/00* | (2006.01) |
| *A61P 35/00* | (2006.01) |
| *A61P 35/02* | (2006.01) |

(52) U.S. Cl.
CPC ........ *C07K 16/2803* (2013.01); *A61K 31/704* (2013.01); *A61K 47/6803* (2017.08); *A61K 47/6849* (2017.08); *A61K 47/6889* (2017.08); *A61P 35/00* (2018.01); *A61P 35/02* (2018.01); *A61K 2039/505* (2013.01); *C07K 2317/21* (2013.01); *C07K 2317/24* (2013.01); *C07K 2317/31* (2013.01); *C07K 2317/565* (2013.01); *C07K 2317/73* (2013.01); *C07K 2317/76* (2013.01); *C07K 2317/77* (2013.01); *C07K 2317/92* (2013.01); *C07K 2319/03* (2013.01); *C07K 2319/30* (2013.01); *C07K 2319/61* (2013.01)

(58) Field of Classification Search
CPC ............ C07K 2317/40; C07K 2319/55; A61K 47/6801
See application file for complete search history.

(56) References Cited

U.S. PATENT DOCUMENTS

| | | | | |
|---|---|---|---|---|
| 5,530,101 | A | * | 6/1996 | Queen ................ C07K 16/2866 530/387.3 |
| 5,859,205 | A | * | 1/1999 | Adair .................. C07K 16/241 530/387.3 |
| 7,462,608 | B2 | | 12/2008 | Chen et al. |
| 8,212,009 | B2 | | 7/2012 | Kipps et al. |
| 8,703,801 | B2 | | 4/2014 | Nair et al. |
| 9,150,647 | B2 | | 1/2015 | Mellstedt et al. |
| 9,163,258 | B2 | | 10/2015 | Riddell et al. |
| 9,228,023 | B2 | | 1/2016 | Rohlff et al. |
| 9,242,014 | B2 | | 1/2016 | Kipps et al. |
| 9,266,952 | B2 | | 2/2016 | Teige |
| 9,316,646 | B2 | | 4/2016 | Rader et al. |
| 9,758,586 | B2 | | 9/2017 | Rader et al. |
| 9,933,434 | B2 | | 4/2018 | Kipps et al. |
| 9,938,350 | B2 | | 4/2018 | Kipps et al. |
| 10,041,090 | B2 | | 8/2018 | Gao et al. |
| 11,364,301 | B2 | * | 6/2022 | Grawunder ........ A61K 47/6889 |
| 2003/0113762 | A1 | | 6/2003 | Warrington et al. |
| 2008/0318212 | A1 | * | 12/2008 | Wilson ................ C12Q 1/6886 435/6.14 |
| 2011/0008347 | A1 | | 1/2011 | Ullrich et al. |
| 2012/0058051 | A1 | | 3/2012 | Rader et al. |
| 2012/0219506 | A1 | | 8/2012 | Moore et al. |
| 2012/0282177 | A1 | | 11/2012 | Rohlff et al. |
| 2013/0122043 | A1 | * | 5/2013 | Guimaraes ......... G01N 33/5035 435/68.1 |

(Continued)

FOREIGN PATENT DOCUMENTS

| | | | |
|---|---|---|---|
| CN | 104662044 | A | 5/2015 |
| CN | 104817642 | A | 8/2015 |

(Continued)

OTHER PUBLICATIONS

Paul (Fundamental Immunology, 3rd Edition, 1993, pp. 292-295) (Year: 1993).*
Bendig M. M. (Methods: A Companion to Methods in Enzymology, 1995; 8:83-93) (Year: 1995).*
Rudikoff et al. (Proceedings of the National Academy of Sciences USA, vol. 79, p. 1979-1983, 1982) (Year: 1982).*
Cook et al. (Vaccine, vol. 13, No. 18, p. 1770-1778, 1995) (Year: 1995).*

(Continued)

*Primary Examiner* — Misook Yu
*Assistant Examiner* — Sarah A Alsomairy
(74) *Attorney, Agent, or Firm* — Morgan, Lewis & Bockius LLP

(57) ABSTRACT

The present invention relates to a human or humanized antibody, or an antibody-based binding protein, modified antibody format retaining target binding capacity, antibody derivative or fragment retaining target binding capacity, which targets Receptor tyrosine kinase-like orphan receptor-1 (ROR1). It further relates to bi- or multispecific antibodies, to Immunoligand-Drug Conjugates, to Chimeric Antigen Receptors and to T-cells comprising such Chimeric Antigen Receptors.

8 Claims, 20 Drawing Sheets

Figure 1:
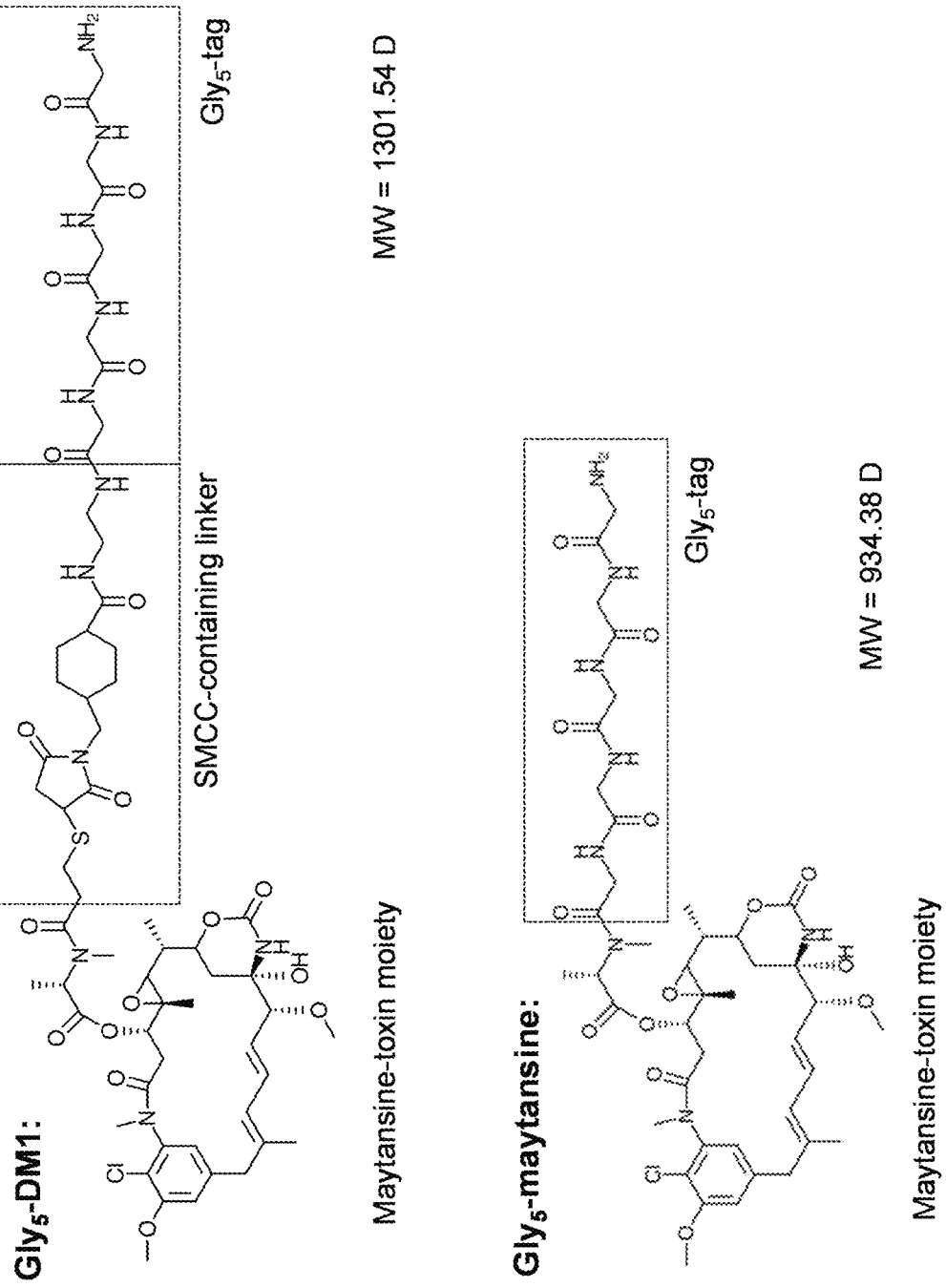

Specification includes a Sequence Listing.

(56) References Cited

U.S. PATENT DOCUMENTS

| | | | |
|---|---|---|---|
| 2013/0131139 A1 | 5/2013 | Tyner et al. | |
| 2013/0251723 A1* | 9/2013 | Rohlff | C07K 16/2803 |
| | | | 435/69.6 |
| 2013/0273073 A1 | 10/2013 | Kipps et al. | |
| 2013/0281922 A1 | 10/2013 | Teige | |
| 2014/0004156 A1 | 2/2014 | Mellstedt et al. | |
| 2015/0258143 A1 | 9/2015 | Malarkannan | |
| 2015/0306141 A1 | 10/2015 | Jensen et al. | |
| 2016/0122430 A1 | 5/2016 | Gish et al. | |
| 2016/0297881 A1 | 10/2016 | Vu et al. | |
| 2016/0362472 A1 | 12/2016 | Bitter et al. | |
| 2017/0015746 A1 | 1/2017 | Jensen | |
| 2017/0029774 A1 | 2/2017 | Jensen et al. | |
| 2017/0051252 A1 | 2/2017 | Morgan et al. | |
| 2017/0152297 A1 | 6/2017 | Jensen | |
| 2017/0198045 A1 | 7/2017 | Johnson et al. | |
| 2017/0204176 A1 | 7/2017 | Bonvini et al. | |
| 2017/0210799 A1 | 7/2017 | Anderson et al. | |
| 2017/0226183 A1 | 8/2017 | Schiffer-Mannioui | |
| 2017/0233472 A1 | 8/2017 | Barat et al. | |
| 2017/0246279 A1 | 8/2017 | Berger et al. | |
| 2017/0267742 A1 | 9/2017 | Jensen et al. | |
| 2017/0275374 A1 | 9/2017 | Schiffer-Mannioui | |
| 2017/0283497 A1 | 10/2017 | Schiffer-Mannioui | |
| 2017/0306018 A1 | 10/2017 | Vu et al. | |
| 2017/0306044 A1 | 10/2017 | Vu et al. | |
| 2017/0314055 A1* | 11/2017 | Heindl | C07K 16/468 |
| 2017/0335281 A1 | 11/2017 | Loew et al. | |
| 2017/0363630 A1 | 12/2017 | Petricoin et al. | |
| 2018/0009891 A1 | 1/2018 | Jensen | |
| 2018/0066063 A1 | 3/2018 | Kipps et al. | |
| 2018/0112002 A1 | 4/2018 | Kipps et al. | |
| 2018/0127503 A1 | 5/2018 | Liu et al. | |
| 2018/0142016 A1 | 5/2018 | Wong et al. | |
| 2018/0147271 A1 | 5/2018 | Morgan et al. | |
| 2018/0340026 A1 | 11/2018 | Rader et al. | |
| 2019/0040132 A1 | 2/2019 | Balakrishnan et al. | |
| 2019/0153092 A1 | 5/2019 | Waldmeier et al. | |

FOREIGN PATENT DOCUMENTS

| | | | | |
|---|---|---|---|---|
| EP | 2649098 | B2 | 11/2017 | |
| WO | WO2007146957 | A2 | 12/2007 | |
| WO | WO2008076868 | A2 | 6/2008 | |
| WO | WO2008103849 | A2 | 8/2008 | |
| WO | 2009099741 | A1 | 8/2009 | |
| WO | WO2009/099741 | * | 8/2009 | |
| WO | WO-2009099741 | A1 * | 8/2009 | A61K 31/5365 |
| WO | WO2010016634 | A2 | 2/2010 | |
| WO | 2010124188 | A1 | 10/2010 | |
| WO | 2012045085 | A1 | 4/2012 | |
| WO | 2012075158 | A1 | 6/2012 | |
| WO | WO2012/075158 | * | 6/2012 | |
| WO | WO2012073217 | A1 | 6/2012 | |
| WO | 2014013026 | A1 | 1/2014 | |
| WO | 2014031174 | A1 | 2/2014 | |
| WO | 2014140317 | A2 | 9/2014 | |
| WO | WO2015113110 | | 8/2015 | |
| WO | WO2016094873 | A2 | 6/2016 | |
| WO | WO-2016094873 | A2 * | 6/2016 | A61K 39/395 |
| WO | WO2016102679 | A1 | 6/2016 | |
| WO | WO2017053469 | A2 | 3/2017 | |
| WO | WO2017107541 | | 6/2017 | |

OTHER PUBLICATIONS

Johnson and Wu (Methods in Molecular Biology, Antibody Engineering: Methods and Protocols, vol. 248, p. 11-25, 2004) (Year: 2004).*

Harris (Biotechnology, vol. 11, p. 1293-1297, 1993) (Year: 1993).*

Balakrishnan et al. (Nov. 16, 2016) "Analysis of ROR1 Protein Expression in Human Cancer and Normal Tissues", Clinical Cancer Research 23:3061-3071 doi: 10.1158/1078-0432.

Beerli, R. et al. (Jul. 1, 2015) "Sortase Enzyme-Mediated Generation of Site-Specifically Conjugated Antibody Drug Conjugates with High In Vitro and In Vivo Potency," PLOS One e0131177.

Berger et al. (Feb. 2015) "Safety of Targeting ROR1 in Primates with Chimeric Antigen Receptor-Modified T Cells", Cancer Immunol. Res. 3(2):206-216 doi: 10.1158/2326-6066.CIR-14-0163.

Cui et al. (Dec. 22, 2016) "High-level ROR1 associates with accelerated disease progression in chronic lymphocytic leukemia", Blood 128(25):2931-2940.

Hudecek et al. (Apr. 25, 2013) "Receptor Affinity and Extracellular Domain Modifications Affect Tumor Recognition by ROR1-Specific Chimeric Antigen Receptor T Cells", Clinical Cancer Res; 19(12):3153-3164 doi: 10.1158/1078-0432.CCR-13-0330.

Quintieri et al. (Feb. 15, 2005) "Formation and Antitumor Activity of PNU-159682, A Major Metabolite of Nemorubicin in Human Liver Microsomes", Clinical Cancer Research, 11(4):1608-1617.

Rebagay et al. (Apr. 18, 2012) "ROR1 and ROR2 in human malignancies: potentials for targeted therapy", Frontiers in Oncology 2(34):1-8 doi: 10.3389/fonc.2012.00034.

Shabani et al. (2015) "Receptor tyrosine kinase-like orphan receptor 1: a novel target for cancer immunotherapy" Expert Opin. Ther. Targets 19(7):1-15.

Spirig et al. (Nov. 7, 2011) "Sortase enzymes in Gram-positive bacteria", Molecular Microbiology, 82(5), 1044-1059 doi: 10.1111/j.1365-2958.2011.07887.x.

Masiakowski and Carroll, J Biol Chem. (1992), 267 (36):26181-26190.

Mackeigan et al., Nat Cell Biol. (2005), DOI: 10.1038/ncb1258:1-10.

Basker et al., Clin Cancer Res. (2008), 14(2):396-404.

Fukuda et al., PNAS. (2008), 105(8):3047-3052.

Daneshmanesh et al. Int. J. Cancer (2008), 123: 1190-1195.

Choi et al., Clinical Lymphoma Myeloma and leukemia 15:S167, 2015.

Peng et al., J Mol Biol. 429, 2954-2973, 2017.

Tyner et al., PNAS (2009), 106(21):8695-8700.

Hudecek et al., Blood (2010), DOI 10.1182/blood-2010-05-283309.

Daneshmanesh et al., Leukemia. (2012), 26:1348-1355.

Baskar et al., mAbs. (2012), 4:3, 349-361.

Patterson et al., Bioconjugate Chemistry 25:1402, 2014.

Hudecek et al., Apr. 25, 2013, "Receptor Affinity and Extracellular Domain Modifications Affect Tumor Recognition by ROR1-Specific Chimeric Antigen Receptor T Cells", Clin Cancer Res; 19(12), 13 pages.

Ulf Grawunder, Feb. 2016, "Development of best-in-class, homogeneous Antibody Drug Conjugates (ADCs) for highly effective and safer cancer therapy", NBE-Therapeutics AG, 25 pages.

International Search Report with Written Opinion corresponding to International Patent Application No. PCT/EP2016/076244, dated Mar. 27, 2017.

Spirig et al., Nov. 7, 2011, "Sortase enzymes in Gram-positive bacteria", Molecular Microbiology, 82(5), 1044-1059.

Office Action dated Apr. 25, 2022, for counterpart Chinese Patent Application No. 201680077230.5.

Office Action dated Aug. 4, 2021, for counterpart Chinese Patent Application No. 201680077230.5.

Search Report for counterpart Chinese Patent Application No. 201680077230.5.

European Office Action dated Nov. 4, 2022, issued in the counterpart European Patent Application No. 16790571.0.

* cited by examiner

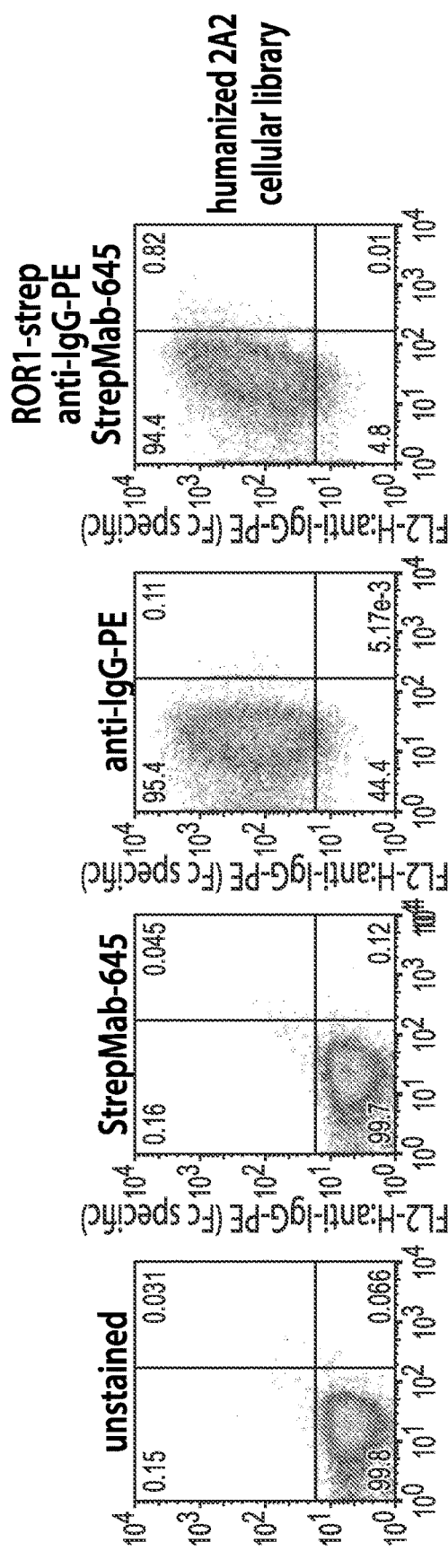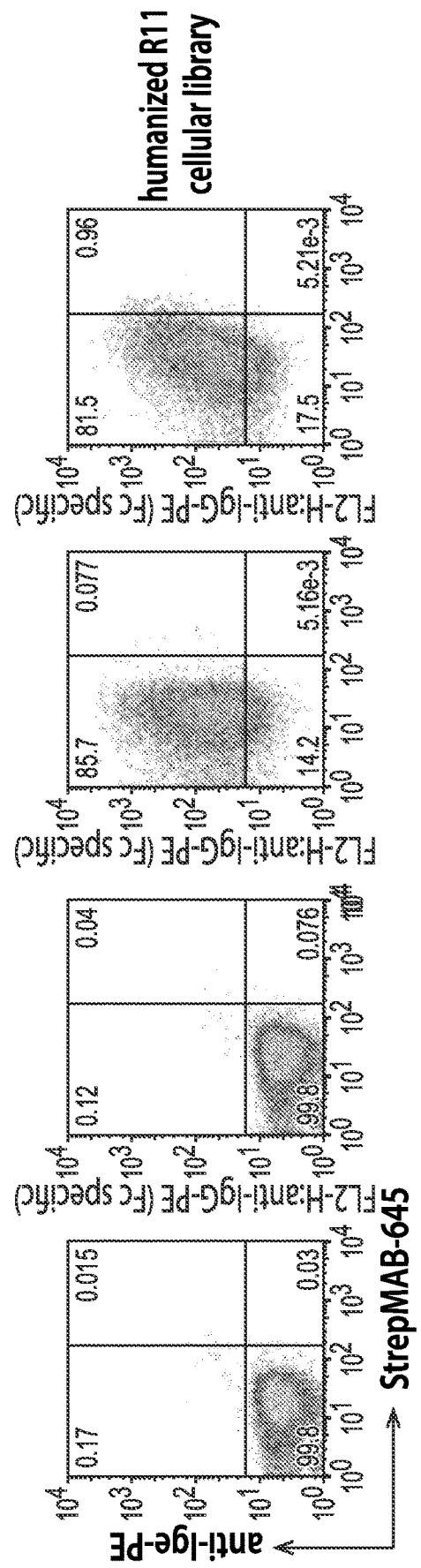
Fig. 9A

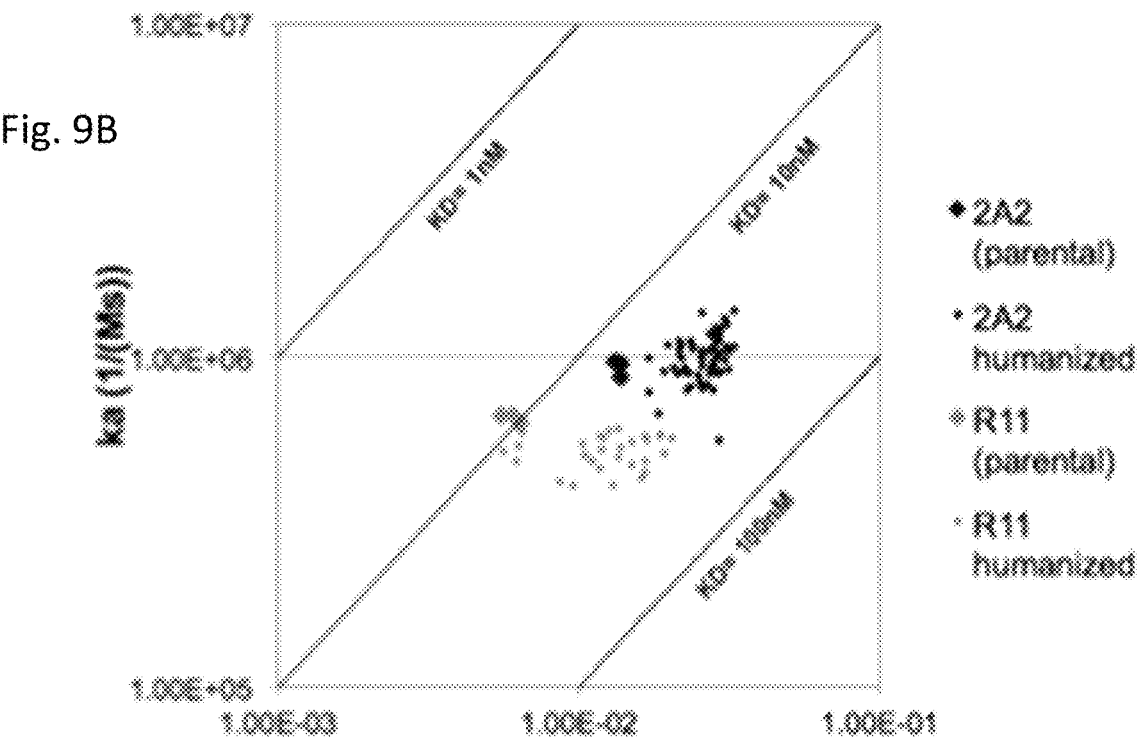
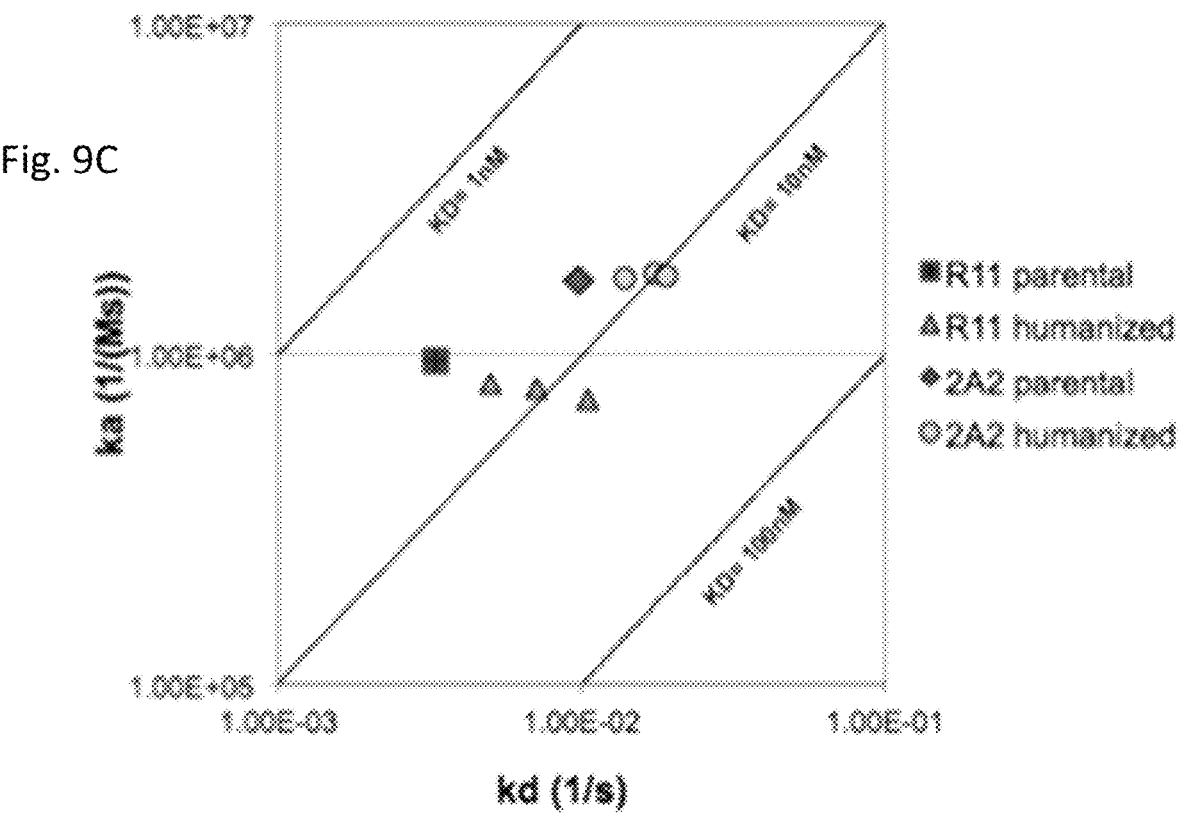

|  | mAb/library | VH FR1,2,3 % human | VL FR1,2,3 % human |
|---|---|---|---|
| FDA-approved humanized mAbs | daclizumab (ZENAPAX®) | 85 | 92 |
|  | palivizumab (MEDI-493, SYNAGIS®) | 89 | 89 |
|  | trastuzumab (HERCEPTIN®) | 89 | 92 |
|  | alemtuzumab (MABCAMPATH®) | 82 | 98 |
|  | omalizumab (XOLAIR®) | 85 | 95 |
|  | bevacizumab (AVASTIN®) | 74 | 92 |
|  | nimotuzumab (THERACIM®) | 77 | 91 |
|  | natalizumab (TYSABRI®) | 93 | 82 |
|  | ranibizumab (LUCENTIS®) | 74 | 91 |
|  | eculizumab (SOLIRIS®) | 89 | 96 |
|  | certolizumab pegol (CIMZIA®) | 87 | 90 |
|  | tocilizumab (ACTEMRA®) | 86 | 96 |
|  | pertuzumab (Perjeta®) | 87 | 90 |
|  | Obinutuzumab (Gazyva®) | 95 | 94 |
| Humanization NBE-Therapeutics | 2A2 (parental) | 64 | 70 |
|  | 2A2 humanization library (average) | 92 | 87 |
|  | hu2A2-D23 | 91 | 85 |
|  | hu2A2-Q11 | 90 | 87 |
|  | hu2A2-D16 | 91 | 86 |
|  | R11 (parental) | 64 | 68 |
|  | R11 humanization library (average) | 88 | 88 |
|  | huR11-Q11 | 88 | 94 |
|  | huR11-D4 | 93 | 86 |
|  | huR11-Q12 | 89 | 86 |
|  | R12 (parental) | 76 | 62 |
|  | R12 humanization library (average) | 79 | 79 |
|  | huR12-11 | 80 | 73 |
|  | huR12-4 | 80 | 73 |
|  | huR12-16 | 77 | 73 |
|  | huR12-7 | 79 | 73 |

Fig. 11

Human ROR1-Strep
according to NP_005003

```
  1         10         20         30         40         50         60         70         80
  MHRPRRRGTRPPLLALLAALLAARGAAAQETELSVSAELVPTSSWNISSELNKDSYLTLDEPMNITTSLGQTAELHCKVSG
  |————Signal peptide————|       |————————————————————huROR1-ECD-Strep————————————————————>

90        100        110        120        130        140        150        160
  NPPPTIRWFKNDAPVVQEPRRLSFRSTIYGSRLRIRNLDTTDTGYFQCVATNGKEVVSSTGVLFVKFGPPPTASPGYSDEYEE
  |————————————————————————————————————huROR1-ECD-Strep————————————————————————————————>

170        180        190        200        210        220        230        240
  DGFCQPYRGIACARFIGNRTVYMESLHMQGEIENQITAAFTMIGTSSHLSDKCSQFAIPSLCHYAFPYCDETSSVPKPRDLCR
  |————————————————————————————————————huROR1-ECD-Strep————————————————————————————————>

250        260        270        280        290        300        310        320        330
  DECEILENVLCQTEYIFARSNPMILMRLKLPNCEDLPQPESPEAANCIRIGIPMADPINKNHKCYNSTGVDYRGTVSVTKSGR
  |————————————————————————————————————huROR1-ECD-Strep————————————————————————————————>

340        350        360        370        380        390        400        410  415
  QCQPWNSQYPHTHTFTALRFPELNGGHSYCRNPGNQKEAPWCFTLDENFKSDLCDIPACDSKDSKEKNKMEILYGWSHPQFEK
  |————————————————huROR1-ECD-Strep————————————————|                              |_Strepe_|
```

Fig. 16

SEQUENCE LISTING

<160> NUMBER OF SEQ ID NOS: 75

<210> SEQ ID NO 1
<211> LENGTH: 8

```
<212> TYPE: PRT
<213> ORGANISM: Artificial Sequence
<220> FEATURE:
<223> OTHER INFORMATION: CDR1 HC 2A2

<400> SEQUENCE: 1

Gly Tyr Thr Phe Ser Asp Tyr Glu
1               5

<210> SEQ ID NO 2
<211> LENGTH: 8
<212> TYPE: PRT
<213> ORGANISM: Artificial Sequence
<220> FEATURE:
<223> OTHER INFORMATION: CDR2 HC 2A2

<400> SEQUENCE: 2

Ile Asp Pro Glu Thr Gly Gly Thr
1               5

<210> SEQ ID NO 3
<211> LENGTH: 11
<212> TYPE: PRT
<213> ORGANISM: Artificial Sequence
<220> FEATURE:
<223> OTHER INFORMATION: CDR3 HC 2A2

<400> SEQUENCE: 3

Thr Gly Tyr Tyr Asp Tyr Asp Ser Phe Thr Tyr
1               5                   10

<210> SEQ ID NO 4
<211> LENGTH: 6
<212> TYPE: PRT
<213> ORGANISM: Artificial Sequence
<220> FEATURE:
<223> OTHER INFORMATION: CDR1 LC 2A2

<400> SEQUENCE: 4

Gln Asn Val Asp Ala Ala
1               5

<210> SEQ ID NO 5
<211> LENGTH: 3
<212> TYPE: PRT
<213> ORGANISM: Artificial Sequence
<220> FEATURE:
<223> OTHER INFORMATION: CDR2 LC 2A2

<400> SEQUENCE: 5

Ser Ala Ser
1

<210> SEQ ID NO 6
<211> LENGTH: 9
<212> TYPE: PRT
<213> ORGANISM: Artificial Sequence
<220> FEATURE:
<223> OTHER INFORMATION: CDR3 LC 2A2

<400> SEQUENCE: 6

Gln Gln Tyr Asp Ile Tyr Pro Tyr Thr
1               5

<210> SEQ ID NO 7
<211> LENGTH: 118
<212> TYPE: PRT
```

```
<213> ORGANISM: Artificial Sequence
<220> FEATURE:
<223> OTHER INFORMATION: VR HC chimeric mAb 2A2

<400> SEQUENCE: 7

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Ser Asp Tyr
            20                  25                  30

Glu Met His Trp Val Ile Gln Thr Pro Val His Gly Leu Glu Trp Ile
        35                  40                  45

Gly Ala Ile Asp Pro Glu Thr Gly Gly Thr Ala Tyr Asn Gln Lys Phe
    50                  55                  60

Lys Gly Lys Ala Ile Leu Thr Ala Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Gly Tyr Tyr Asp Tyr Asp Ser Phe Thr Tyr Trp Gly Gln Gly Thr
            100                 105                 110

Leu Val Thr Val Ser Ala
        115

<210> SEQ ID NO 8
<211> LENGTH: 107
<212> TYPE: PRT
<213> ORGANISM: Artificial Sequence
<220> FEATURE:
<223> OTHER INFORMATION: VR LC chimeric mAb 2A2

<400> SEQUENCE: 8

Asp Ile Val Met Thr Gln Ser Gln Lys Ile Met Ser Thr Thr Val Gly
1               5                   10                  15

Asp Arg Val Ser Ile Thr Cys Lys Ala Ser Gln Asn Val Asp Ala Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
    50                  55                  60

Ser Gly Ser Gly Thr Asp Phe Thr Leu Thr Ile Ser Asn Met Gln Ser
65                  70                  75                  80

Glu Asp Leu Ala Asp Tyr Phe Cys Gln Gln Tyr Asp Ile Tyr Pro Tyr
                85                  90                  95

Thr Phe Gly Gly Gly Thr Lys Leu Glu Ile Lys
            100                 105

<210> SEQ ID NO 9
<211> LENGTH: 118
<212> TYPE: PRT
<213> ORGANISM: Artificial Sequence
<220> FEATURE:
<223> OTHER INFORMATION: VR HC hu2A2bQ11, humanized from 2A2

<400> SEQUENCE: 9

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
            20                  25                  30

Glu Met His Trp Val Arg Gln Ala Pro Gly Gln Gly Leu Glu Trp Leu
        35                  40                  45
```

```
Gly Ala Ile Asp Pro Glu Thr Gly Gly Thr Ala Tyr Asn Gln Lys Phe
            50                  55                  60

Lys Gly Arg Val Thr Met Thr Gly Asp Thr Ser Ile Ser Thr Ala Tyr
 65                  70                  75                  80

Met Glu Leu Ser Arg Leu Thr Ser Asp Asp Thr Ala Val Tyr Tyr Cys
                85                  90                  95

Thr Gly Tyr Tyr Asp Tyr Asp Ser Phe Thr Tyr Trp Gly Gln Gly Thr
                100                 105                 110

Leu Val Ser Val Ser Ser
            115

<210> SEQ ID NO 10
<211> LENGTH: 107
<212> TYPE: PRT
<213> ORGANISM: Artificial Sequence
<220> FEATURE:
<223> OTHER INFORMATION: VR LC hu2A2bQ11, humanized from 2A2

<400> SEQUENCE: 10

Asp Ile Gln Met Thr Gln Ser Pro Ser Ser Leu Ser Thr Ser Val Gly
 1               5                  10                  15

Asp Arg Val Thr Ile Thr Cys Lys Ala Ser Gln Asn Val Asp Ala Ala
                20                  25                  30

Val Ala Trp Tyr Gln Gln Lys Pro Gly Lys Ala Pro Lys Leu Leu Ile
            35                  40                  45

Tyr Ser Ala Ser Asn Arg Tyr Thr Gly Val Ala Ser Arg Phe Ser Gly
    50                  55                  60

Ser Gly Ser Gly Thr Asp Phe Thr Phe Thr Ile Ser Ser Leu Gln Ser
 65                  70                  75                  80

Glu Asp Leu Ala Asp Tyr Phe Cys Gln Gln Tyr Asp Ile Tyr Pro Tyr
                85                  90                  95

Thr Phe Gly Gln Gly Thr Lys Leu Glu Ile Lys
            100                 105

<210> SEQ ID NO 11
<211> LENGTH: 118
<212> TYPE: PRT
<213> ORGANISM: Artificial Sequence
<220> FEATURE:
<223> OTHER INFORMATION: VR HC hu2A2D23, humanized from 2A2

<400> SEQUENCE: 11

Gln Val Gln Leu Val Glu Ser Gly Ala Glu Val Lys Lys Pro Gly Ala
 1               5                  10                  15

Ser Val Lys Leu Ser Cys Lys Ala Ser Gly Tyr Thr Phe Ser Asp Tyr
                20                  25                  30

Glu Met His Trp Val Arg Gln Ala Pro Gly Gln Arg Leu Glu Trp Met
            35                  40                  45

Gly Ala Ile Asp Pro Glu Thr Gly Gly Thr Ala Tyr Asn Gln Lys Phe
    50                  55                  60

Lys Gly Arg Val Thr Ile Thr Val Asp Lys Ser Ala Ser Thr Ala Tyr
 65                  70                  75                  80

Met Glu Leu Ser Ser Leu Arg Ser Glu Asp Thr Ala Val Tyr Tyr Cys
                85                  90                  95

Thr Gly Tyr Tyr Asp Tyr Asp Ser Phe Thr Tyr Trp Gly Pro Gly Thr
                100                 105                 110

Thr Val Thr Val Ser Ser
```

-continued

```
<210> SEQ ID NO 12
<211> LENGTH: 107
<212> TYPE: PRT
<213> ORGANISM: Artificial Sequence
<220> FEATURE:
<223> OTHER INFORMATION: VR LC hu2A2D23, humanized from 2A2

<400> SEQUENCE: 12

Asp Ile Val Met Thr Gln Ser Pro Ser Thr Leu Ser Ala Ser Val Gly
1               5                   10                  15

Asp Arg Val Thr Ile Thr Cys Lys Ala Ser Gln Asn Val Asp Ala Ala
            20                  25                  30

Val Ala Trp Tyr Gln Gln Lys Pro Gly Thr Ala Pro Lys Leu Leu Ile
        35                  40                  45

Tyr Ser Ala Ser Asn Arg Tyr Thr Gly Val Pro Ser Arg Phe Ser Gly
    50                  55                  60

Ser Gly Ser Gly Thr Glu Phe Thr Leu Thr Ile Ser Ser Leu Gln Ser
65                  70                  75                  80

Glu Asp Leu Ala Asp Tyr Phe Cys Gln Gln Tyr Asp Ile Tyr Pro Tyr
                85                  90                  95

Thr Phe Gly Gln Gly Thr Lys Leu Glu Ile Lys
            100                 105

<210> SEQ ID NO 13
<211> LENGTH: 118
<212> TYPE: PRT
<213> ORGANISM: Artificial Sequence
<220> FEATURE:
<223> OTHER INFORMATION: VR HC hu2A2D16, humanized from 2A2

<400> SEQUENCE: 13

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Ser Asp Tyr
            20                  25                  30

Glu Met His Trp Val Arg Gln Ala Pro Gly Gln Gly Leu Glu Trp Val
        35                  40                  45

Gly Ala Ile Asp Pro Glu Thr Gly Gly Thr Ala Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Gly Tyr Tyr Asp Tyr Asp Ser Phe Thr Tyr Trp Gly Gln Gly Thr
            100                 105                 110

Leu Val Thr Val Ser Ser
        115

<210> SEQ ID NO 14
<211> LENGTH: 107
<212> TYPE: PRT
<213> ORGANISM: Artificial Sequence
<220> FEATURE:
<223> OTHER INFORMATION: VR LC hu2A2D16, humanized from 2A2

<400> SEQUENCE: 14

Asp Ile Gln Met Thr Gln Ser Pro Ser Ser Leu Ser Ala Ser Val Gly
1               5                   10                  15
```

```
Asp Arg Val Thr Ile Thr Cys Lys Ala Ser Gln Asn Val Asp Ala Ala
            20                  25                  30

Val Ala Trp Tyr Gln Gln Lys Pro Gly Lys Ala Pro Lys Leu Leu Ile
        35                  40                  45

Tyr Ser Ala Ser Asn Arg Tyr Thr Gly Ile Pro Thr Arg Phe Ser Gly
    50                  55                  60

Ser Gly Ser Gly Thr Asp Phe Thr Leu Thr Ile Ser Ser Leu Gln Ser
65                  70                  75                  80

Glu Asp Leu Ala Asp Tyr Phe Cys Gln Gln Tyr Asp Ile Tyr Pro Tyr
                85                  90                  95

Thr Phe Gly Gln Gly Thr Lys Val Glu Ile Lys
            100                 105

<210> SEQ ID NO 15
<211> LENGTH: 8
<212> TYPE: PRT
<213> ORGANISM: Artificial Sequence
<220> FEATURE:
<223> OTHER INFORMATION: CDR1 HC R11

<400> SEQUENCE: 15

Gly Ser Asp Ile Asn Asp Tyr Pro
1               5

<210> SEQ ID NO 16
<211> LENGTH: 7
<212> TYPE: PRT
<213> ORGANISM: Artificial Sequence
<220> FEATURE:
<223> OTHER INFORMATION: CDR2 HC R11

<400> SEQUENCE: 16

Ile Asn Ser Gly Gly Ser Thr
1               5

<210> SEQ ID NO 17
<211> LENGTH: 11
<212> TYPE: PRT
<213> ORGANISM: Artificial Sequence
<220> FEATURE:
<223> OTHER INFORMATION: CDR3 HC R11

<400> SEQUENCE: 17

Gly Tyr Ser Thr Tyr Tyr Gly Asp Phe Asn Ile
1               5                   10

<210> SEQ ID NO 18
<211> LENGTH: 6
<212> TYPE: PRT
<213> ORGANISM: Artificial Sequence
<220> FEATURE:
<223> OTHER INFORMATION: CDR1 LC R11

<400> SEQUENCE: 18

Gln Ser Ile Asp Ser Asn
1               5

<210> SEQ ID NO 19
<211> LENGTH: 3
<212> TYPE: PRT
<213> ORGANISM: Artificial Sequence
<220> FEATURE:
<223> OTHER INFORMATION: CDR2 LC R11
```

<400> SEQUENCE: 19

Arg Ala Ser
1

<210> SEQ ID NO 20
<211> LENGTH: 12
<212> TYPE: PRT
<213> ORGANISM: Artificial Sequence
<220> FEATURE:
<223> OTHER INFORMATION: CDR3 LC R11

<400> SEQUENCE: 20

Leu Gly Gly Val Gly Asn Val Ser Tyr Arg Thr Ser
1               5                   10

<210> SEQ ID NO 21
<211> LENGTH: 116
<212> TYPE: PRT
<213> ORGANISM: Artificial Sequence
<220> FEATURE:
<223> OTHER INFORMATION: VR HC chimeric mAb R11

<400> SEQUENCE: 21

Gln Ser Val Lys Glu Ser Glu Gly Asp Leu Val Thr Pro Ala Gly Asn
1               5                   10                  15

Leu Thr Leu Thr Cys Thr Ala Ser Gly Ser Asp Ile Asn Asp Tyr Pro
            20                  25                  30

Ile Ser Trp Val Arg Gln Ala Pro Gly Lys Gly Leu Glu Trp Ile Gly
        35                  40                  45

Phe Ile Asn Ser Gly Gly Ser Thr Trp Tyr Ala Ser Trp Val Lys Gly
    50                  55                  60

Arg Phe Thr Ile Ser Arg Thr Ser Thr Val Asp Leu Lys Met Thr
65                  70                  75                  80

Ser Leu Thr Thr Asp Asp Thr Ala Thr Tyr Phe Cys Ala Arg Gly Tyr
                85                  90                  95

Ser Thr Tyr Tyr Gly Asp Phe Asn Ile Trp Gly Pro Gly Thr Leu Val
            100                 105                 110

Thr Ile Ser Ser
        115

<210> SEQ ID NO 22
<211> LENGTH: 110
<212> TYPE: PRT
<213> ORGANISM: Artificial Sequence
<220> FEATURE:
<223> OTHER INFORMATION: VR LC chimeric mAb R11

<400> SEQUENCE: 22

Glu Leu Val Met Thr Gln Thr Pro Ser Ser Thr Ser Gly Ala Val Gly
1               5                   10                  15

Gly Thr Val Thr Ile Asn Cys Gln Ala Ser Gln Ser Ile Asp Ser Asn
            20                  25                  30

Leu Ala Trp Phe Gln Gln Lys Pro Gly Gln Pro Pro Thr Leu Leu Ile
        35                  40                  45

Tyr Arg Ala Ser Asn Leu Ala Ser Gly Val Pro Ser Arg Phe Ser Gly
    50                  55                  60

Ser Arg Ser Gly Thr Glu Tyr Thr Leu Thr Ile Ser Gly Val Gln Arg
65                  70                  75                  80

Glu Asp Ala Ala Thr Tyr Tyr Cys Leu Gly Gly Val Gly Asn Val Ser
                85                  90                  95

```
Tyr Arg Thr Ser Phe Gly Gly Gly Thr Glu Val Val Val Lys
            100                 105                 110
```

<210> SEQ ID NO 23
<211> LENGTH: 138
<212> TYPE: PRT
<213> ORGANISM: Artificial Sequence
<220> FEATURE:
<223> OTHER INFORMATION: VR HC rbQ11, humanized from R11

<400> SEQUENCE: 23

```
Met Asn Phe Gly Leu Arg Leu Ile Phe Leu Val Leu Thr Leu Lys Gly
1               5                   10                  15

Val Gln Cys Glu Val Gln Leu Val Gln Ser Gly Gly Leu Val Gln
            20                  25                  30

Pro Gly Gly Ser Leu Arg Leu Ser Cys Ala Ala Ser Gly Ser Asp Ile
            35                  40                  45

Asn Asp Tyr Pro Ile Ser Trp Val Arg Gln Ala Pro Gly Lys Gly Leu
        50                  55                  60

Glu Trp Val Ser Phe Ile Asn Ser Gly Gly Ser Thr Trp Tyr Ala Ser
65                  70                  75                  80

Trp Val Lys Gly Arg Phe Thr Ile Ser Arg Asp Asn Ala Lys Asn Ser
                85                  90                  95

Leu Tyr Leu Gln Met Asn Ser Leu Arg Asp Asp Asp Thr Ala Thr Tyr
            100                 105                 110

Phe Cys Ala Arg Gly Tyr Ser Thr Tyr Tyr Gly Asp Phe Asn Ile Trp
        115                 120                 125

Gly Gln Gly Thr Leu Val Thr Val Ser Ser
        130                 135
```

<210> SEQ ID NO 24
<211> LENGTH: 129
<212> TYPE: PRT
<213> ORGANISM: Artificial Sequence
<220> FEATURE:
<223> OTHER INFORMATION: VR LC rbQ11, humanized from R11

<400> SEQUENCE: 24

```
Met Asn Phe Gly Leu Arg Leu Ile Phe Leu Val Leu Thr Leu Lys Gly
1               5                   10                  15

Val Gln Cys Asp Ile Val Met Thr Gln Ser Pro Ser Ser Leu Ser Ala
            20                  25                  30

Ser Val Gly Asp Arg Val Thr Ile Thr Cys Gln Ala Ser Gln Ser Ile
            35                  40                  45

Asp Ser Asn Leu Ala Trp Phe Gln Gln Lys Pro Gly Lys Ala Pro Lys
        50                  55                  60

Ser Leu Ile Tyr Arg Ala Ser Asn Leu Ala Ser Gly Val Pro Ser Lys
65                  70                  75                  80

Phe Ser Gly Ser Gly Ser Gly Thr Asp Phe Thr Leu Thr Ile Ser Ser
                85                  90                  95

Leu Gln Arg Glu Asp Ala Ala Thr Tyr Tyr Cys Leu Gly Gly Val Gly
            100                 105                 110

Asn Val Ser Tyr Arg Thr Ser Phe Gly Gly Gly Thr Lys Val Glu Ile
        115                 120                 125

Lys
```

<210> SEQ ID NO 25

```
<211> LENGTH: 119
<212> TYPE: PRT
<213> ORGANISM: Artificial Sequence
<220> FEATURE:
<223> OTHER INFORMATION: VR HC rbD4, humanized from R11

<400> SEQUENCE: 25
```

Glu Val Gln Leu Val Glu Ser Gly Gly Gly Leu Val Gln Pro Gly Arg
1               5                   10                  15

Ser Leu Arg Leu Ser Cys Thr Ala Ser Gly Ser Asp Ile Asn Asp Tyr
            20                  25                  30

Pro Ile Ser Trp Phe Arg Gln Ala Pro Gly Lys Gly Leu Glu Trp Val
        35                  40                  45

Gly Phe Ile Asn Ser Gly Gly Ser Thr Trp Tyr Ala Ser Trp Val Lys
50                  55                  60

Gly Arg Phe Thr Ile Ser Arg Asp Asp Ser Lys Ser Ile Ala Tyr Leu
65                  70                  75                  80

Gln Met Asn Ser Leu Lys Thr Asp Asp Thr Ala Thr Tyr Phe Cys Ala
                85                  90                  95

Arg Gly Tyr Ser Thr Tyr Tyr Gly Asp Phe Asn Ile Trp Gly Gln Gly
            100                 105                 110

Thr Thr Val Thr Val Ser Ser
        115

```
<210> SEQ ID NO 26
<211> LENGTH: 110
<212> TYPE: PRT
<213> ORGANISM: Artificial Sequence
<220> FEATURE:
<223> OTHER INFORMATION: VR LC rbD4, humanized from R11

<400> SEQUENCE: 26
```

Asp Val Val Met Thr Gln Ser Pro Ser Ser Leu Ser Ala Ser Val Gly
1               5                   10                  15

Asp Arg Val Thr Ile Thr Cys Gln Ala Ser Gln Ser Ile Asp Ser Asn
            20                  25                  30

Leu Ala Trp Phe Gln Gln Lys Pro Gly Lys Ala Pro Asn Leu Leu Ile
        35                  40                  45

Tyr Arg Ala Ser Asn Leu Ala Ser Gly Val Pro Ser Arg Phe Ser Gly
50                  55                  60

Ser Gly Ser Gly Thr Glu Phe Thr Leu Thr Ile Ser Ser Leu Gln Arg
65                  70                  75                  80

Glu Asp Ala Ala Thr Tyr Tyr Cys Leu Gly Val Gly Asn Val Ser
                85                  90                  95

Tyr Arg Thr Ser Phe Gly Gln Gly Thr Lys Val Glu Ile Lys
            100                 105                 110

```
<210> SEQ ID NO 27
<211> LENGTH: 119
<212> TYPE: PRT
<213> ORGANISM: Artificial Sequence
<220> FEATURE:
<223> OTHER INFORMATION: VR HC rbQ12, humanized from R11

<400> SEQUENCE: 27
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Asp Ile Asn Asp Tyr
            20                  25                  30

```
Pro Ile Ser Trp Val Arg Gln Ala Pro Gly Lys Gly Leu Glu Trp Val
            35                  40                  45

Ser Phe Ile Asn Ser Gly Gly Ser Thr Trp Tyr Ala Ser Trp Val Lys
 50                  55                  60

Gly Arg Phe Thr Ile Ser Arg Asp Asn Ala Lys Asn Ser Leu Tyr Leu
 65                  70                  75                  80

Gln Met Asn Ser Leu Arg Ala Asp Asp Thr Ala Thr Tyr Phe Cys Ala
                 85                  90                  95

Arg Gly Tyr Ser Thr Tyr Tyr Gly Asp Phe Asn Ile Trp Gly Gln Gly
            100                 105                 110

Thr Met Val Thr Val Ser Ser
        115
```

<210> SEQ ID NO 28
<211> LENGTH: 110
<212> TYPE: PRT
<213> ORGANISM: Artificial Sequence
<220> FEATURE:
<223> OTHER INFORMATION: VR LC rbQ12, humanized from R11

<400> SEQUENCE: 28

```
Glu Ile Val Met Thr Gln Ser Pro Ser Ser Leu Ser Ala Ser Val Gly
 1               5                  10                  15

Asp Arg Val Thr Ile Thr Cys Gln Ala Ser Gln Ser Ile Asp Ser Asn
            20                  25                  30

Leu Ala Trp Phe Gln Gln Lys Pro Gly Lys Ala Pro Asn Leu Leu Ile
            35                  40                  45

Tyr Arg Ala Ser Asn Leu Ala Ser Gly Val Pro Ser Arg Phe Ser Gly
 50                  55                  60

Ser Gly Ser Gly Thr Glu Phe Thr Leu Thr Ile Ser Ser Leu Gln Arg
 65                  70                  75                  80

Glu Asp Ala Ala Thr Tyr Tyr Cys Leu Gly Gly Val Gly Asn Val Ser
                 85                  90                  95

Tyr Arg Thr Ser Phe Gly Gln Gly Thr Lys Val Glu Ile Lys
            100                 105                 110
```

<210> SEQ ID NO 29
<211> LENGTH: 8
<212> TYPE: PRT
<213> ORGANISM: Artificial Sequence
<220> FEATURE:
<223> OTHER INFORMATION: CDR1 HC R12

<400> SEQUENCE: 29

```
Gly Phe Asp Phe Ser Ala Tyr Tyr
 1               5
```

<210> SEQ ID NO 30
<211> LENGTH: 8
<212> TYPE: PRT
<213> ORGANISM: Artificial Sequence
<220> FEATURE:
<223> OTHER INFORMATION: CDR2 HC R12

<400> SEQUENCE: 30

```
Ile Tyr Pro Ser Ser Gly Lys Thr
 1               5
```

<210> SEQ ID NO 31
<211> LENGTH: 14
<212> TYPE: PRT

-continued

<213> ORGANISM: Artificial Sequence
<220> FEATURE:
<223> OTHER INFORMATION: CDR3 HC R12

<400> SEQUENCE: 31

Ala Arg Asp Ser Tyr Ala Asp Asp Gly Ala Leu Phe Asn Ile
1               5                   10

<210> SEQ ID NO 32
<211> LENGTH: 7
<212> TYPE: PRT
<213> ORGANISM: Artificial Sequence
<220> FEATURE:
<223> OTHER INFORMATION: CDR1 LC R12

<400> SEQUENCE: 32

Ser Ala His Lys Thr Asp Thr
1               5

<210> SEQ ID NO 33
<211> LENGTH: 7
<212> TYPE: PRT
<213> ORGANISM: Artificial Sequence
<220> FEATURE:
<223> OTHER INFORMATION: CDR2 LC R12

<400> SEQUENCE: 33

Val Gln Ser Asp Gly Ser Tyr
1               5

<210> SEQ ID NO 34
<211> LENGTH: 9
<212> TYPE: PRT
<213> ORGANISM: Artificial Sequence
<220> FEATURE:
<223> OTHER INFORMATION: CDR3 LC R12

<400> SEQUENCE: 34

Gly Ala Asp Tyr Ile Gly Gly Tyr Val
1               5

<210> SEQ ID NO 35
<211> LENGTH: 121
<212> TYPE: PRT
<213> ORGANISM: Artificial Sequence
<220> FEATURE:
<223> OTHER INFORMATION: VR HC Chimeric mAb R12

<400> SEQUENCE: 35

Gln Glu Gln Leu Val Glu Ser Gly Gly Arg Leu Val Thr Pro Gly Gly
1               5                   10                  15

Ser Leu Thr Leu Ser Cys Lys Ala Ser Gly Phe Asp Phe Ser Ala Tyr
                20                  25                  30

Tyr Met Ser Trp Val Arg Gln Ala Pro Gly Lys Gly Leu Glu Trp Ile
            35                  40                  45

Ala Thr Ile Tyr Pro Ser Ser Gly Lys Thr Tyr Tyr Ala Thr Trp Val
        50                  55                  60

Asn Gly Arg Phe Thr Ile Ser Ser Asp Asn Ala Gln Asn Thr Val Asp
65                  70                  75                  80

Leu Gln Met Asn Ser Leu Thr Ala Ala Asp Arg Ala Thr Tyr Phe Cys
                85                  90                  95

Ala Arg Asp Ser Tyr Ala Asp Asp Gly Ala Leu Phe Asn Ile Trp Gly
                100                 105                 110

```
Pro Gly Thr Leu Val Thr Ile Ser Ser
        115                 120

<210> SEQ ID NO 36
<211> LENGTH: 111
<212> TYPE: PRT
<213> ORGANISM: Artificial Sequence
<220> FEATURE:
<223> OTHER INFORMATION: VR LC Chimeric mAb R12

<400> SEQUENCE: 36

Glu Leu Val Leu Thr Gln Ser Pro Ser Val Ser Ala Ala Leu Gly Ser
1               5                   10                  15

Pro Ala Lys Ile Thr Cys Thr Leu Ser Ser Ala His Lys Thr Asp Thr
            20                  25                  30

Ile Asp Trp Tyr Gln Gln Leu Gln Gly Glu Ala Pro Arg Tyr Leu Met
        35                  40                  45

Gln Val Gln Ser Asp Gly Ser Tyr Thr Lys Arg Pro Gly Val Pro Asp
    50                  55                  60

Arg Phe Ser Gly Ser Ser Ser Gly Ala Asp Arg Tyr Leu Ile Ile Pro
65                  70                  75                  80

Ser Val Gln Ala Asp Asp Glu Ala Asp Tyr Tyr Cys Gly Ala Asp Tyr
                85                  90                  95

Ile Gly Gly Tyr Val Phe Gly Gly Gly Thr Gln Leu Thr Val Thr
            100                 105                 110

<210> SEQ ID NO 37
<211> LENGTH: 121
<212> TYPE: PRT
<213> ORGANISM: Artificial Sequence
<220> FEATURE:
<223> OTHER INFORMATION: VR HC huR12_4, humanized from R12

<400> SEQUENCE: 37

Gln Val Gln Leu Val Glu Ser Gly Gly Glu Leu Val Gln Pro Gly Gly
1               5                   10                  15

Ser Leu Thr Leu Ser Cys Lys Ala Ser Gly Phe Asp Phe Ser Ala Tyr
            20                  25                  30

Tyr Met Ser Trp Val Arg Gln Ala Pro Gly Lys Gly Leu Glu Trp Ile
        35                  40                  45

Ala Thr Ile Tyr Pro Ser Ser Gly Lys Thr Tyr Tyr Ala Ala Ser Val
    50                  55                  60

Gln Gly Arg Phe Thr Ile Ser Ala Asp Asn Ala Lys Asn Thr Val Tyr
65                  70                  75                  80

Leu Gln Met Asn Ser Leu Thr Ala Ala Asp Thr Ala Thr Tyr Phe Cys
                85                  90                  95

Ala Arg Asp Ser Tyr Ala Asp Asp Gly Ala Leu Phe Asn Ile Trp Gly
            100                 105                 110

Lys Gly Thr Leu Val Thr Val Ser Ser
        115                 120

<210> SEQ ID NO 38
<211> LENGTH: 112
<212> TYPE: PRT
<213> ORGANISM: Artificial Sequence
<220> FEATURE:
<223> OTHER INFORMATION: VR LC huR12_4, humanized from R12

<400> SEQUENCE: 38

Gln Leu Val Leu Thr Gln Ser Pro Ser Val Ser Ala Ala Leu Gly Ser
```

```
                1               5                   10                  15
Ser Ala Lys Ile Thr Cys Thr Leu Ser Ser Ala His Lys Thr Asp Thr
                20                  25                  30

Ile Asp Trp Tyr Gln Gln Leu Ala Gly Gln Ala Pro Arg Tyr Leu Met
            35                  40                  45

Tyr Val Gln Ser Asp Gly Ser Tyr Glu Lys Arg Ser Gly Val Pro Asp
        50                  55                  60

Arg Phe Ser Gly Ser Ala Ser Gly Ala Asp Arg Tyr Leu Ala Ile Ser
65                  70                  75                  80

Arg Val Gln Ala Asp Asp Glu Ala Asp Tyr Tyr Cys Gly Ala Asp Tyr
                85                  90                  95

Ile Gly Gly Tyr Val Phe Gly Gly Gly Thr Gln Leu Thr Val Leu Gly
                100                 105                 110
```

<210> SEQ ID NO 39
<211> LENGTH: 121
<212> TYPE: PRT
<213> ORGANISM: Artificial Sequence
<220> FEATURE:
<223> OTHER INFORMATION: VR HC huR12_7, humanized from R12

<400> SEQUENCE: 39

```
Gln Val Gln Leu Val Glu Ser Gly Gly Glu Leu Val Gln Pro Gly Gly
1               5                   10                  15

Ser Leu Thr Leu Ser Cys Lys Ala Ser Gly Phe Asp Phe Ser Ala Tyr
                20                  25                  30

Tyr Met Ser Trp Val Arg Gln Ala Pro Gly Lys Gly Leu Glu Trp Ile
            35                  40                  45

Ala Thr Ile Tyr Pro Ser Ser Gly Lys Thr Tyr Tyr Ala Ala Ser Val
        50                  55                  60

Gln Gly Arg Phe Thr Ile Ser Ala Asp Asn Ala Lys Asn Thr Val Ser
65                  70                  75                  80

Leu Gln Met Asn Ser Leu Thr Ala Ala Asp Thr Ala Thr Tyr Phe Cys
                85                  90                  95

Ala Arg Asp Ser Tyr Ala Asp Asp Gly Ala Leu Phe Asn Ile Trp Gly
                100                 105                 110

Lys Gly Thr Leu Val Thr Val Ser Ser
            115                 120
```

<210> SEQ ID NO 40
<211> LENGTH: 112
<212> TYPE: PRT
<213> ORGANISM: Artificial Sequence
<220> FEATURE:
<223> OTHER INFORMATION: VR LC huR12_7, humanized from R12

<400> SEQUENCE: 40

```
Gln Leu Val Leu Thr Gln Ser Pro Ser Val Ser Ala Ala Leu Gly Ser
1               5                   10                  15

Ser Ala Lys Ile Thr Cys Thr Leu Ser Ser Ala His Lys Thr Asp Thr
                20                  25                  30

Ile Asp Trp Tyr Gln Gln Leu Ala Gly Gln Ala Pro Arg Tyr Leu Met
            35                  40                  45

Tyr Val Gln Ser Asp Gly Ser Tyr Glu Lys Arg Ser Gly Val Pro Asp
        50                  55                  60

Arg Phe Ser Gly Ser Ser Gly Ala Asp Arg Tyr Leu Ile Ile Ser
65                  70                  75                  80
```

Ser Val Gln Ala Asp Asp Glu Ala Asp Tyr Tyr Cys Gly Ala Asp Tyr
                85                  90                  95

Ile Gly Gly Tyr Val Phe Gly Gly Gly Thr Gln Leu Thr Val Leu Gly
            100                 105                 110

<210> SEQ ID NO 41
<211> LENGTH: 121
<212> TYPE: PRT
<213> ORGANISM: Artificial Sequence
<220> FEATURE:
<223> OTHER INFORMATION: VR HC huR12_11, humanized from R12

<400> SEQUENCE: 41

Gln Val Gln Leu Val Glu Ser Gly Gly Ala Leu Val Gln Pro Gly Gly
1               5                   10                  15

Ser Leu Thr Leu Ser Cys Lys Ala Ser Gly Phe Asp Phe Ser Ala Tyr
            20                  25                  30

Tyr Met Ser Trp Val Arg Gln Ala Pro Gly Lys Gly Leu Glu Trp Ile
        35                  40                  45

Ala Thr Ile Tyr Pro Ser Ser Gly Lys Thr Tyr Tyr Ala Ala Ser Val
    50                  55                  60

Gln Gly Arg Phe Thr Ile Ser Ala Asp Asn Ala Lys Asn Thr Val Tyr
65                  70                  75                  80

Leu Gln Met Asn Ser Leu Thr Ala Ala Asp Thr Ala Thr Tyr Phe Cys
                85                  90                  95

Ala Arg Asp Ser Tyr Ala Asp Asp Gly Ala Leu Phe Asn Ile Trp Gly
            100                 105                 110

Gln Gly Thr Leu Val Thr Val Ser Ser
        115                 120

<210> SEQ ID NO 42
<211> LENGTH: 111
<212> TYPE: PRT
<213> ORGANISM: Artificial Sequence
<220> FEATURE:
<223> OTHER INFORMATION: VR LC huR12_11, humanized from R12

<400> SEQUENCE: 42

Gln Leu Val Leu Thr Gln Ser Pro Ser Val Ser Ala Ala Leu Gly Ser
1               5                   10                  15

Ser Ala Lys Ile Thr Cys Thr Leu Ser Ser Ala His Lys Thr Asp Thr
            20                  25                  30

Ile Asp Trp Tyr Gln Gln Leu Ala Gly Gln Ala Pro Arg Tyr Leu Met
        35                  40                  45

Tyr Val Gln Ser Asp Gly Ser Tyr Glu Lys Arg Ser Gly Val Pro Asp
    50                  55                  60

Arg Phe Ser Gly Ser Ser Gly Ala Asp Arg Tyr Leu Ile Ile Ser
65                  70                  75                  80

Ser Val Gln Ala Asp Asp Glu Ala Asp Tyr Tyr Cys Gly Ala Asp Tyr
                85                  90                  95

Ile Gly Gly Tyr Val Phe Gly Gly Gly Thr Gln Leu Thr Val Leu Gly
            100                 105                 110

<210> SEQ ID NO 43
<211> LENGTH: 121
<212> TYPE: PRT
<213> ORGANISM: Artificial Sequence
<220> FEATURE:
<223> OTHER INFORMATION: VR HC huR12_16, humanized from R12

<400> SEQUENCE: 43

```
Gln Val Gln Leu Val Glu Ser Gly Gly Glu Leu Val Thr Pro Gly Gly
1               5                   10                  15

Ser Leu Thr Leu Ser Cys Lys Ala Ser Gly Phe Asp Phe Ser Ala Tyr
            20                  25                  30

Tyr Met Ser Trp Val Arg Gln Ala Pro Gly Lys Gly Leu Glu Trp Ile
        35                  40                  45

Ala Ser Ile Tyr Pro Ser Ser Gly Lys Thr Tyr Tyr Ala Ala Ala Val
    50                  55                  60

Gln Gly Arg Phe Thr Ile Ser Ala Asp Asn Ala Lys Asn Thr Val Tyr
65                  70                  75                  80

Leu Gln Met Asn Ser Leu Thr Ala Ala Asp Thr Ala Thr Tyr Phe Cys
                85                  90                  95

Ala Arg Asp Ser Tyr Ala Asp Asp Gly Ala Leu Phe Asn Ile Trp Gly
            100                 105                 110

Gln Gly Thr Leu Val Thr Val Ser Ser
        115                 120
```

<210> SEQ ID NO 44
<211> LENGTH: 111
<212> TYPE: PRT
<213> ORGANISM: Artificial Sequence
<220> FEATURE:
<223> OTHER INFORMATION: VR LC huR12_16, humanized from R12

<400> SEQUENCE: 44

```
Gln Leu Val Leu Thr Gln Ser Pro Ser Val Ser Ala Ala Leu Gly Ser
1               5                   10                  15

Ser Ala Lys Ile Thr Cys Thr Leu Ser Ser Ala His Lys Thr Asp Thr
            20                  25                  30

Ile Asp Trp Tyr Gln Gln Leu Ala Gly Gln Ala Pro Arg Tyr Leu Met
        35                  40                  45

Tyr Val Gln Ser Asp Gly Ser Tyr Glu Lys Arg Ser Gly Val Pro Asp
    50                  55                  60

Arg Phe Ser Gly Ser Ser Ser Gly Ala Asp Arg Tyr Leu Ile Ile Ser
65                  70                  75                  80

Ser Val Gln Ala Asp Asp Glu Ala Asp Tyr Tyr Cys Gly Ala Asp Tyr
                85                  90                  95

Ile Gly Gly Tyr Val Phe Gly Gly Gly Thr Gln Leu Thr Val Gly
            100                 105                 110
```

<210> SEQ ID NO 45
<211> LENGTH: 27
<212> TYPE: DNA
<213> ORGANISM: Artificial Sequence
<220> FEATURE:
<223> OTHER INFORMATION: forward primer univNotISPF

<400> SEQUENCE: 45
gaggaggcgg ccgccatgaa ctttggg                                        27

<210> SEQ ID NO 46
<211> LENGTH: 21
<212> TYPE: DNA
<213> ORGANISM: Artificial Sequence
<220> FEATURE:
<223> OTHER INFORMATION: reverse primer huCG1B

<400> SEQUENCE: 46
aagaccgatg ggcccttggt g                                          21

<210> SEQ ID NO 47
<211> LENGTH: 21
<212> TYPE: DNA
<213> ORGANISM: Artificial Sequence
<220> FEATURE:
<223> OTHER INFORMATION: reverse primer huCKB

<400> SEQUENCE: 47
gaagacagat ggtgcagcca c                                          21

<210> SEQ ID NO 48
<211> LENGTH: 20
<212> TYPE: DNA
<213> ORGANISM: Artificial Sequence
<220> FEATURE:
<223> OTHER INFORMATION: reverse primer huCLB

<400> SEQUENCE: 48
ggaaacagag tcacgcttgg                                            20

<210> SEQ ID NO 49
<211> LENGTH: 20
<212> TYPE: DNA
<213> ORGANISM: Artificial Sequence
<220> FEATURE:
<223> OTHER INFORMATION: primer pPBseq13

<400> SEQUENCE: 49
ggccagcttg gcacttgatg                                            20

<210> SEQ ID NO 50
<211> LENGTH: 20
<212> TYPE: DNA
<213> ORGANISM: Artificial Sequence
<220> FEATURE:
<223> OTHER INFORMATION: forward primer EF1aNotI_F

<400> SEQUENCE: 50
ccatttcagg tgtcgtgagc                                            20

<210> SEQ ID NO 51
<211> LENGTH: 20
<212> TYPE: DNA
<213> ORGANISM: Artificial Sequence
<220> FEATURE:
<223> OTHER INFORMATION: reverse primer CGrevseq1

<400> SEQUENCE: 51
gttcggggaa gtagtccttg                                            20

<210> SEQ ID NO 52
<211> LENGTH: 28
<212> TYPE: DNA
<213> ORGANISM: Artificial Sequence
<220> FEATURE:
<223> OTHER INFORMATION: Intronrev1

<400> SEQUENCE: 52
gtggatgtca gtaagaccaa taggtgcc                                   28

<210> SEQ ID NO 53
<211> LENGTH: 21
<212> TYPE: DNA
<213> ORGANISM: Artificial Sequence

```
<220> FEATURE:
<223> OTHER INFORMATION: sequencing primer CMVseq2

<400> SEQUENCE: 53
gcagtgtagt ctgagcagta c                                              21

<210> SEQ ID NO 54
<211> LENGTH: 19
<212> TYPE: PRT
<213> ORGANISM: Artificial Sequence
<220> FEATURE:
<223> OTHER INFORMATION: leader sequence

<400> SEQUENCE: 54

Met Asn Phe Gly Leu Arg Leu Ile Phe Leu Val Leu Thr Leu Lys Gly
1               5                   10                  15

Val Gln Cys

<210> SEQ ID NO 55
<211> LENGTH: 9
<212> TYPE: PRT
<213> ORGANISM: Artificial Sequence
<220> FEATURE:
<223> OTHER INFORMATION: strep tag

<400> SEQUENCE: 55

Gly Trp Ser His Pro Gln Phe Glu Lys
1               5

<210> SEQ ID NO 56
<211> LENGTH: 14
<212> TYPE: PRT
<213> ORGANISM: Artificial Sequence
<220> FEATURE:
<223> OTHER INFORMATION: IgH-chain tag

<400> SEQUENCE: 56

Leu Pro Glu Thr Gly Gly Trp Ser His Pro Gln Phe Glu Lys
1               5                   10

<210> SEQ ID NO 57
<211> LENGTH: 21
<212> TYPE: PRT
<213> ORGANISM: Artificial Sequence
<220> FEATURE:
<223> OTHER INFORMATION: IgL-chain tag

<400> SEQUENCE: 57

Gly Gly Gly Gly Ser Leu Pro Glu Thr Gly Gly Trp Ser His Pro Gln
1               5                   10                  15

Phe Gln Phe Glu Lys
            20

<210> SEQ ID NO 58
<211> LENGTH: 5
<212> TYPE: PRT
<213> ORGANISM: Artificial Sequence
<220> FEATURE:
<223> OTHER INFORMATION: Sortase recognition tag
<220> FEATURE:
<221> NAME/KEY: misc_feature
<222> LOCATION: (3)..(3)
<223> OTHER INFORMATION: Xaa can be any naturally occurring amino acid

<400> SEQUENCE: 58

Leu Pro Xaa Thr Gly
```

```
<210> SEQ ID NO 59
<211> LENGTH: 5
<212> TYPE: PRT
<213> ORGANISM: Artificial Sequence
<220> FEATURE:
<223> OTHER INFORMATION: Sortase recognition tag
<220> FEATURE:
<221> NAME/KEY: misc_feature
<222> LOCATION: (3)..(3)
<223> OTHER INFORMATION: Xaa can be any naturally occurring amino acid

<400> SEQUENCE: 59

Leu Pro Xaa Ala Gly
1               5

<210> SEQ ID NO 60
<211> LENGTH: 5
<212> TYPE: PRT
<213> ORGANISM: Artificial Sequence
<220> FEATURE:
<223> OTHER INFORMATION: Sortase recognition tag
<220> FEATURE:
<221> NAME/KEY: misc_feature
<222> LOCATION: (3)..(3)
<223> OTHER INFORMATION: Xaa can be any naturally occurring amino acid

<400> SEQUENCE: 60

Leu Pro Xaa Ser Gly
1               5

<210> SEQ ID NO 61
<211> LENGTH: 5
<212> TYPE: PRT
<213> ORGANISM: Artificial Sequence
<220> FEATURE:
<223> OTHER INFORMATION: Sortase recognition tag
<220> FEATURE:
<221> NAME/KEY: misc_feature
<222> LOCATION: (3)..(3)
<223> OTHER INFORMATION: Xaa can be any naturally occurring amino acid

<400> SEQUENCE: 61

Leu Ala Xaa Thr Gly
1               5

<210> SEQ ID NO 62
<211> LENGTH: 5
<212> TYPE: PRT
<213> ORGANISM: Artificial Sequence
<220> FEATURE:
<223> OTHER INFORMATION: Sortase recognition tag

<400> SEQUENCE: 62

Leu Ala Glu Thr Gly
1               5

<210> SEQ ID NO 63
<211> LENGTH: 5
<212> TYPE: PRT
<213> ORGANISM: Artificial Sequence
<220> FEATURE:
<223> OTHER INFORMATION: Sortase recognition tag
<220> FEATURE:
<221> NAME/KEY: misc_feature
<222> LOCATION: (3)..(3)
<223> OTHER INFORMATION: Xaa can be any naturally occurring amino acid

<400> SEQUENCE: 63
```

```
Leu Pro Xaa Thr Ala
1               5

<210> SEQ ID NO 64
<211> LENGTH: 5
<212> TYPE: PRT
<213> ORGANISM: Artificial Sequence
<220> FEATURE:
<223> OTHER INFORMATION: Sortase recognition tag

<400> SEQUENCE: 64

Asn Pro Gln Thr Asn
1               5

<210> SEQ ID NO 65
<211> LENGTH: 105
<212> TYPE: PRT
<213> ORGANISM: artificial sequence
<220> FEATURE:
<223> OTHER INFORMATION: Sortase recognition tag
<220> FEATURE:
<221> NAME/KEY: misc_feature
<222> LOCATION: (3)..(103)
<223> OTHER INFORMATION: Xaa can be any naturally occurring amino acid
<220> FEATURE:
<221> NAME/KEY: MISC_FEATURE
<222> LOCATION: (6)..(105)
<223> OTHER INFORMATION: Each sequence of LPXSG may be present or absent

<400> SEQUENCE: 65

Leu Pro Xaa Ser Gly Leu Pro Xaa Ser Gly Leu Pro Xaa Ser Gly Leu
1               5                   10                  15

Pro Xaa Ser Gly Leu Pro Xaa Ser Gly Leu Pro Xaa Ser Gly Leu Pro
            20                  25                  30

Xaa Ser Gly Leu Pro Xaa Ser Gly Leu Pro Xaa Ser Gly Leu Pro Xaa
        35                  40                  45

Ser Gly Leu Pro Xaa Ser Gly Leu Pro Xaa Ser Gly Leu Pro Xaa Ser
    50                  55                  60

Gly Leu Pro Xaa Ser Gly Leu Pro Xaa Ser Gly Leu Pro Xaa Ser Gly
65                  70                  75                  80

Leu Pro Xaa Ser Gly Leu Pro Xaa Ser Gly Leu Pro Xaa Ser Gly Leu
                85                  90                  95

Pro Xaa Ser Gly Leu Pro Xaa Ser Gly
            100                 105

<210> SEQ ID NO 66
<211> LENGTH: 105
<212> TYPE: PRT
<213> ORGANISM: artificial sequence
<220> FEATURE:
<223> OTHER INFORMATION: Sortase recognition tag
<220> FEATURE:
<221> NAME/KEY: MISC_FEATURE
<222> LOCATION: (3)..(103)
<223> OTHER INFORMATION: Xaa can be any amino acid
<220> FEATURE:
<221> NAME/KEY: MISC_FEATURE
<222> LOCATION: (6)..(105)
<223> OTHER INFORMATION: Each sequence of LPXAG may be present or absent

<400> SEQUENCE: 66

Leu Pro Xaa Ala Gly Leu Pro Xaa Ala Gly Leu Pro Xaa Ala Gly Leu
1               5                   10                  15

Pro Xaa Ala Gly Leu Pro Xaa Ala Gly Leu Pro Xaa Ala Gly Leu Pro
            20                  25                  30
```

-continued

```
Xaa Ala Gly Leu Pro Xaa Ala Gly Leu Pro Xaa Ala Gly Leu Pro Xaa
        35                  40                  45

Ala Gly Leu Pro Xaa Ala Gly Leu Pro Xaa Ala Gly Leu Pro Xaa Ala
 50                  55                  60

Gly Leu Pro Xaa Ala Gly Leu Pro Xaa Ala Gly Leu Pro Xaa Ala Gly
 65                  70                  75                  80

Leu Pro Xaa Ala Gly Leu Pro Xaa Ala Gly Leu Pro Xaa Ala Gly Leu
            85                  90                  95

Pro Xaa Ala Gly Leu Pro Xaa Ala Gly
        100                 105

<210> SEQ ID NO 67
<211> LENGTH: 105
<212> TYPE: PRT
<213> ORGANISM: artificial sequence
<220> FEATURE:
<223> OTHER INFORMATION: Sortase recognition tag
<220> FEATURE:
<221> NAME/KEY: MISC_FEATURE
<222> LOCATION: (3)..(103)
<223> OTHER INFORMATION: Xaa can be any amino acid
<220> FEATURE:
<221> NAME/KEY: MISC_FEATURE
<222> LOCATION: (6)..(105)
<223> OTHER INFORMATION: Each sequence of LPXTG may be present or absent

<400> SEQUENCE: 67

Leu Pro Xaa Thr Gly Leu Pro Xaa Thr Gly Leu Pro Xaa Thr Gly Leu
 1               5                  10                  15

Pro Xaa Thr Gly Leu Pro Xaa Thr Gly Leu Pro Xaa Thr Gly Leu Pro
            20                  25                  30

Xaa Thr Gly Leu Pro Xaa Thr Gly Leu Pro Xaa Thr Gly Leu Pro Xaa
        35                  40                  45

Thr Gly Leu Pro Xaa Thr Gly Leu Pro Xaa Thr Gly Leu Pro Xaa Thr
 50                  55                  60

Gly Leu Pro Xaa Thr Gly Leu Pro Xaa Thr Gly Leu Pro Xaa Thr Gly
 65                  70                  75                  80

Leu Pro Xaa Thr Gly Leu Pro Xaa Thr Gly Leu Pro Xaa Thr Gly Leu
            85                  90                  95

Pro Xaa Thr Gly Leu Pro Xaa Thr Gly
        100                 105

<210> SEQ ID NO 68
<211> LENGTH: 105
<212> TYPE: PRT
<213> ORGANISM: artificial sequence
<220> FEATURE:
<223> OTHER INFORMATION: Sortase recognition tag
<220> FEATURE:
<221> NAME/KEY: MISC_FEATURE
<222> LOCATION: (3)..(103)
<223> OTHER INFORMATION: Xaa can be any amino acid
<220> FEATURE:
<221> NAME/KEY: MISC_FEATURE
<222> LOCATION: (6)..(105)
<223> OTHER INFORMATION: Each sequence of LAXTG may be present or absent

<400> SEQUENCE: 68

Leu Ala Xaa Thr Gly Leu Ala Xaa Thr Gly Leu Ala Xaa Thr Gly Leu
 1               5                  10                  15

Ala Xaa Thr Gly Leu Ala Xaa Thr Gly Leu Ala Xaa Thr Gly Leu Ala
            20                  25                  30
```

-continued

```
Xaa Thr Gly Leu Ala Xaa Thr Gly Leu Ala Xaa Thr Gly Leu Ala Xaa
            35                  40                  45

Thr Gly Leu Ala Xaa Thr Gly Leu Ala Xaa Thr Gly Leu Ala Xaa Thr
 50                  55                  60

Gly Leu Ala Xaa Thr Gly Leu Ala Xaa Thr Gly Leu Ala Xaa Thr Gly
 65                  70                  75                  80

Leu Ala Xaa Thr Gly Leu Ala Xaa Thr Gly Leu Ala Xaa Thr Gly Leu
                85                  90                  95

Ala Xaa Thr Gly Leu Ala Xaa Thr Gly
            100                 105

<210> SEQ ID NO 69
<211> LENGTH: 105
<212> TYPE: PRT
<213> ORGANISM: artificial sequence
<220> FEATURE:
<223> OTHER INFORMATION: Sortase recognition tag
<220> FEATURE:
<221> NAME/KEY: MISC_FEATURE
<222> LOCATION: (6)..(105)
<223> OTHER INFORMATION: Each sequence of LAETG may be present or absent

<400> SEQUENCE: 69

Leu Ala Glu Thr Gly Leu Ala Glu Thr Gly Leu Ala Glu Thr Gly Leu
 1               5                  10                  15

Ala Glu Thr Gly Leu Ala Glu Thr Gly Leu Ala Glu Thr Gly Leu Ala
                20                  25                  30

Glu Thr Gly Leu Ala Glu Thr Gly Leu Ala Glu Thr Gly Leu Ala Glu
            35                  40                  45

Thr Gly Leu Ala Glu Thr Gly Leu Ala Glu Thr Gly Leu Ala Glu Thr
 50                  55                  60

Gly Leu Ala Glu Thr Gly Leu Ala Glu Thr Gly Leu Ala Glu Thr Gly
 65                  70                  75                  80

Leu Ala Glu Thr Gly Leu Ala Glu Thr Gly Leu Ala Glu Thr Gly Leu
                85                  90                  95

Ala Glu Thr Gly Leu Ala Glu Thr Gly
            100                 105

<210> SEQ ID NO 70
<211> LENGTH: 105
<212> TYPE: PRT
<213> ORGANISM: artificial sequence
<220> FEATURE:
<223> OTHER INFORMATION: Sortase recognition tag
<220> FEATURE:
<221> NAME/KEY: MISC_FEATURE
<222> LOCATION: (3)..(103)
<223> OTHER INFORMATION: Xaa can be any amino acid
<220> FEATURE:
<221> NAME/KEY: MISC_FEATURE
<222> LOCATION: (6)..(105)
<223> OTHER INFORMATION: Each sequence of LPXTA may be present or absent

<400> SEQUENCE: 70

Leu Pro Xaa Thr Ala Leu Pro Xaa Thr Ala Leu Pro Xaa Thr Ala Leu
 1               5                  10                  15

Pro Xaa Thr Ala Leu Pro Xaa Thr Ala Leu Pro Xaa Thr Ala Leu Pro
                20                  25                  30

Xaa Thr Ala Leu Pro Xaa Thr Ala Leu Pro Xaa Thr Ala Leu Pro Xaa
            35                  40                  45

Thr Ala Leu Pro Xaa Thr Ala Leu Pro Xaa Thr Ala Leu Pro Xaa Thr
 50                  55                  60
```

```
Ala Leu Pro Xaa Thr Ala Leu Pro Xaa Thr Ala Leu Pro Xaa Thr Ala
 65                  70                  75                  80

Leu Pro Xaa Thr Ala Leu Pro Xaa Thr Ala Leu Pro Xaa Thr Ala Leu
                 85                  90                  95

Pro Xaa Thr Ala Leu Pro Xaa Thr Ala
            100                 105

<210> SEQ ID NO 71
<211> LENGTH: 105
<212> TYPE: PRT
<213> ORGANISM: artificial sequence
<220> FEATURE:
<223> OTHER INFORMATION: Sortase recognition tag
<220> FEATURE:
<221> NAME/KEY: MISC_FEATURE
<222> LOCATION: (6)..(105)
<223> OTHER INFORMATION: Each sequence of NPQTG may be present or absent

<400> SEQUENCE: 71

Asn Pro Gln Thr Gly Asn Pro Gln Thr Gly Asn Pro Gln Thr Gly Asn
  1               5                  10                  15

Pro Gln Thr Gly Asn Pro Gln Thr Gly Asn Pro Gln Thr Gly Asn Pro
                 20                  25                  30

Gln Thr Gly Asn Pro Gln Thr Gly Asn Pro Gln Thr Gly Asn Pro Gln
             35                  40                  45

Thr Gly Asn Pro Gln Thr Gly Asn Pro Gln Thr Gly Asn Pro Gln Thr
 50                  55                  60

Gly Asn Pro Gln Thr Gly Asn Pro Gln Thr Gly Asn Pro Gln Thr Gly
 65                  70                  75                  80

Asn Pro Gln Thr Gly Asn Pro Gln Thr Gly Asn Pro Gln Thr Gly Asn
                 85                  90                  95

Pro Gln Thr Gly Asn Pro Gln Thr Gly
            100                 105

<210> SEQ ID NO 72
<211> LENGTH: 21
<212> TYPE: PRT
<213> ORGANISM: artificial sequence
<220> FEATURE:
<223> OTHER INFORMATION: oligo-glycine peptide
<220> FEATURE:
<221> NAME/KEY: MISC_FEATURE
<222> LOCATION: (2)..(21)
<223> OTHER INFORMATION: each G may be present or absent

<400> SEQUENCE: 72

Gly Gly Gly Gly Gly Gly Gly Gly Gly Gly Gly Gly Gly Gly Gly Gly
  1               5                  10                  15

Gly Gly Gly Gly Gly
             20

<210> SEQ ID NO 73
<211> LENGTH: 5
<212> TYPE: PRT
<213> ORGANISM: artificial sequence
<220> FEATURE:
<223> OTHER INFORMATION: Sortase recognition tag

<400> SEQUENCE: 73

Leu Pro Glu Thr Gly
  1               5
```

-continued

```
<210> SEQ ID NO 74
<211> LENGTH: 8
<212> TYPE: PRT
<213> ORGANISM: Artificial Sequence
<220> FEATURE:
<223> OTHER INFORMATION: Strep tag

<400> SEQUENCE: 74

Trp Ser His Pro Gln Phe Glu Lys
1               5

<210> SEQ ID NO 75
<211> LENGTH: 415
<212> TYPE: PRT
<213> ORGANISM: artificial sequence
<220> FEATURE:
<223> OTHER INFORMATION: Strep-tagged human ROR1

<400> SEQUENCE: 75

Met His Arg Pro Arg Arg Arg Gly Thr Arg Pro Pro Leu Leu Ala Leu
1               5                   10                  15

Leu Ala Ala Leu Leu Leu Ala Ala Arg Gly Ala Ala Ala Gln Glu Thr
            20                  25                  30

Glu Leu Ser Val Ser Ala Glu Leu Val Pro Thr Ser Ser Trp Asn Ile
        35                  40                  45

Ser Ser Glu Leu Asn Lys Asp Ser Tyr Leu Thr Leu Asp Glu Pro Met
    50                  55                  60

Asn Asn Ile Thr Thr Ser Leu Gly Gln Thr Ala Glu Leu His Cys Lys
65                  70                  75                  80

Val Ser Gly Asn Pro Pro Pro Thr Ile Arg Trp Phe Lys Asn Asp Ala
                85                  90                  95

Pro Val Val Gln Glu Pro Arg Arg Leu Ser Phe Arg Ser Thr Ile Tyr
            100                 105                 110

Gly Ser Arg Leu Arg Ile Arg Asn Leu Asp Thr Thr Asp Thr Gly Tyr
        115                 120                 125

Phe Gln Cys Val Ala Thr Asn Gly Lys Glu Val Val Ser Ser Thr Gly
    130                 135                 140

Val Leu Phe Val Lys Phe Gly Pro Pro Thr Ala Ser Pro Gly Tyr
145                 150                 155                 160

Ser Asp Glu Tyr Glu Glu Asp Gly Phe Cys Gln Pro Tyr Arg Gly Ile
                165                 170                 175

Ala Cys Ala Arg Phe Ile Gly Asn Arg Thr Val Tyr Met Glu Ser Leu
            180                 185                 190

His Met Gln Gly Glu Ile Glu Asn Gln Ile Thr Ala Ala Phe Thr Met
        195                 200                 205

Ile Gly Thr Ser Ser His Leu Ser Asp Lys Cys Ser Gln Phe Ala Ile
    210                 215                 220

Pro Ser Leu Cys His Tyr Ala Phe Pro Tyr Cys Asp Glu Thr Ser Ser
225                 230                 235                 240

Val Pro Lys Pro Arg Asp Leu Cys Arg Asp Glu Cys Glu Ile Leu Glu
                245                 250                 255

Asn Val Leu Cys Gln Thr Glu Tyr Ile Phe Ala Arg Ser Asn Pro Met
            260                 265                 270

Ile Leu Met Arg Leu Lys Leu Pro Asn Cys Glu Asp Leu Pro Gln Pro
        275                 280                 285

Glu Ser Pro Glu Ala Ala Asn Cys Ile Arg Ile Gly Ile Pro Met Ala
    290                 295                 300
```

-continued

```
Asp Pro Ile Asn Lys Asn His Lys Cys Tyr Asn Ser Thr Gly Val Asp
305             310             315             320

Tyr Arg Gly Thr Val Ser Val Thr Lys Ser Gly Arg Gln Cys Gln Pro
            325             330             335

Trp Asn Ser Gln Tyr Pro His Thr His Thr Phe Thr Ala Leu Arg Phe
            340             345             350

Pro Glu Leu Asn Gly Gly His Ser Tyr Cys Arg Asn Pro Gly Asn Gln
        355             360             365

Lys Glu Ala Pro Trp Cys Phe Thr Leu Asp Glu Asn Phe Lys Ser Asp
    370             375             380

Leu Cys Asp Ile Pro Ala Cys Asp Ser Lys Asp Ser Lys Glu Lys Asn
385             390             395             400

Lys Met Glu Ile Leu Tyr Gly Trp Ser His Pro Gln Phe Glu Lys
            405             410             415
```

ANTI-ROR1 ANTIBODIES

CROSS-REFERENCE TO RELATED APPLICATIONS

This application is a 35 U.S.C. § 371 filing of International Patent Application No. PCT/EP2016/076244, filed Oct. 31, 2016, which claims priority to European Patent Application No. 15192446.1, filed Oct. 30, 2015, the entire contents of which are incorporated herein by reference.

SEQUENCE LISTING SUBMISSION VIA EFS-WEB

A computer readable text file, entitled "SequenceListing.txt," created on or about Dec. 23, 2020 with a file size of about 49 kb contains the sequence listing for this application and is hereby incorporated by reference in its entirety.

The present invention relates to anti-ROR1 antibodies, including bispecific and multispecific antibodies, Immunoligand-Toxin Conjugates targeting ROR1, and anti ROR1 CARs and CAR cells.

INTRODUCTION

For several neoplastic diseases, no efficacious therapeutic approaches exist. This applies, inter alia, to chronic lymphocytic leukemia (CLL), acute lymphocytic leukemia (ALL), non-Hodgkin lymphomas (NHL), and myeloid malignancies, as well as to solid cancers including colon, lung, breast, ovarian and pancreatic cancers.

It is an object of the present invention to provide new therapeutic approaches to address these diseases.

PREFERRED EMBODIMENTS

It is to be understood that embodiments disclosed herein are not meant to be understood as individual embodiments which would not relate to one another. Features discussed with one embodiment are meant to be disclosed also in connection with other embodiments shown herein. If, in one case, a specific feature is not disclosed with one embodiment, but with another, the skilled person would understand that does not necessary mean that said feature is not meant to be disclosed with said other embodiment. The skilled person would understand that it is the gist of this application to disclose said feature also for the other embodiment, but that just for purposes of clarity and to keep the specification in a manageable volume this has not been done.

According to a first embodiment of the invention, a human or humanized antibody, or an antibody-based binding protein, or a modified antibody format retaining target binding capacity, or an antibody derivative or fragment retaining target binding capacity is provided, which targets Receptor tyrosine kinase-like orphan receptor-1 (ROR1).

In a second embodiment also an Immunoligand-Drug conjugate of said first embodiment with a functional moiety covalently coupled to a human or humanized antibody, or an antibody-based binding protein, or a modified antibody format retaining target binding capacity, or an antibody derivative or fragment retaining target binding capacity is provided, which targets Receptor tyrosine kinase-like orphan receptor-1 (ROR1). This conjugate is preferably an antibody drug conjugate (ADC), to which preferably a small molecular weight cellular toxin is conjugated, preferably site-specifically, and preferably by, but not limited to sortase-enzyme mediated conjugation technology (SMAC-technology) disclosed in WO2014140317.

In a third embodiment, also mammalian cells carrying receptors comprising a human or humanized antibody, or an antibody-based binding protein, or a modified antibody format retaining target binding capacity, or an antibody derivative or fragment retaining target binding capacity for Receptor tyrosine kinase-like orphan receptor-1 (ROR1) is provided. Such mammalian cells are preferably T cells of the immune system, carrying preferably chimeric antigen receptors (CARs) comprising said human or humanized antibody, or an antibody-based binding protein, or a modified antibody format retaining target binding capacity, or an antibody derivative or fragment retaining target binding capacity for Receptor tyrosine kinase-like orphan receptor-1 (ROR1). In a further preferred embodiment, these mammalian cells are therefore CAR T cells comprising said human or humanized antibody, or an antibody-based binding protein, or a modified antibody format retaining target binding capacity, or an antibody derivative or fragment retaining target binding capacity for Receptor tyrosine kinase-like orphan receptor-1 (ROR1).

Receptor tyrosine kinase-like orphan receptor-1 (ROR1), is a member of the receptor tyrosine kinase (RTK) family of cell surface molecules, that is highly expressed during embryonic and fetal development and which is important for embryonic and fetal development, because ROR-1 knockout mice die neonatally (Nomi M et al. (2001) Mol Cell Biol. 21, 8329-35). In postpartum human tissue, ROR1 expression was found to be mostly absent. Low expression has been observed in adipose tissue, and to a minor extent in pancreas, lung, and a subset of intermediate B cells. However, importantly, elevated ROR1 expression has been found in several cancers, including hematological malignancies as chronic lymphocytic leukemia (CLL), acute lymphocytic leukemia (ALL), mantle cell lymphoma, non-Hodgkin lymphomas (NHL), and myeloid malignancies, as well as in solid cancers, including neuroblastoma, sarcoma, renal cell carcinoma, melanoma, colon cancer, lung cancer, breast cancer, ovarian cancer, head and neck cancer, and pancreatic cancer. Therefore, the expression patter of ROR1 is referred to as onco-fetal expression pattern and therefore is of high medical interest as a target for particular cancers and tumors (Borcherding N et al (2014) Protein Cell 5, 496-502; Hojjat-Farsangi et al (2014) Seminars in Cancer Biology, 29, 21-31).

In line with the virtual absence of ROR1 expression in postpartum tissue, no toxicity was observed when non-human primates that were treated with ROR1-specific cytotoxic T cells suggesting that specific targeting of ROR1 in humans for cancer therapy is safe (Berger C et al. (2015) Cancer Immunol Res. 3, 206-16). Thus far, no ROR1-specific antibodies have clinically been approved for cancer therapy.

To be applicable for the therapy of human disease, antibodies targeting ROR-1, and Immunoligand-Toxin-Conjugates targeting ROR-1, should show minimal immunogenicity, thus minimizing the possibility to be cleared from the system by the immune-system of patients and thus resulting in prolonged serum half-life and, consequently, higher efficiency. Further, reduced immunogenicity avoids unwanted and sometimes even life threatening side effects, like immunogenic reactions.

Therefore the present invention provides human and humanized anti-ROR-1 antibodies, which are expected to result in minimal immunogenicity and with efficacy in the treatment of neoplastic conditions.

In one specific embodiment, humanized anti-ROR-1 antibodies, or antibody-based binding proteins, modified antibody formats retaining target binding capacity, antibody derivatives or fragments retaining target binding capacity are provided.

The term "humanized antibody" refers to a chimeric antibody that contains sequences derived from human and non-human (e.g., rabbit) immunoglobulins such that substantially all of the CDR regions are of non-human origin, while substantially all of the FR regions correspond to those of a human immunoglobulin sequence. In one embodiment, the antibody has been humanized from a rodent or rabbit parent antibody, i.e., comprises CDR regions that are of rodent or rabbit origin.

The humanized antibodies have been developed on the basis of functionally characterized anti-ROR1 rodent antibodies from mouse and rabbit origin, named R11, R12 (both rabbit) (WO 2012/075158 A1) and 2A2 (mouse) (WO 2010/124188 A1), which all bind different extracellular domains of the ROR1 molecule, namely the Ig, the frizzled and the Kringle domains of ROR1 (Yang J et al. (2011) PLoS ONE 6, e21018; Baskar S et al. (2012) mAbs 4, 1-13).

These antibodies have been humanized by proprietary algorithms, on the basis of sequence alignments to large next-generation sequencing data from human antibody repertoires and selecting human frameworks with maximal similarity to human IgG heavy and light chain sequences. Collections of identified human framework regions with desired sequence homology to the parental antibody clones have been selected and combined with the CDRs of high affinity rodent mAbs R11, R12 and 2A2.

Collections of up to 183 predicted humanized antibodies have been gene synthesized and libraries of individual IgG heavy and light chains have stably been expressed and displayed on the surface of mammalian cells using transposition-mediated antibody Display (Transpo-mAb) as described (Waldmeier et al. (2016) MAbs 8(4): 726-740, WO2014013026).

Individual combinations of humanized antibody heavy and light chains have been selected based on ROR1 target binding efficiency and best clones were analyzed for sequence recovery. Based on the screening of larger repertoires of humanized IgG heavy and light chains, high-affinity humanized mAbs could be identifies without further affinity maturation.

The provided humanized anti-ROR-1 antibodies show, in some cases, unexpectedly significant improvements in the binding affinity towards ROR1 relative to the parental antibodies from which they were derived. This is unexpected because humanization of antibodies usually leads to a reduction or loss in affinity, that tediously needs to be compensated by additional affinity maturation (Baca et al. (1997) J. Biol. Chem. 271: 10678-84).

In a preferred embodiment, the antibody comprises at least the 3 CDR sequences:

| SEQ ID No 1 | CDR1 HC |
| SEQ ID No 2 | CDR2 HC |
| SEQ ID No 3 | CDR3 HC | or

| SEQ ID NO 15 | CDR1 HC |
| SEQ ID NO 16 | CDR2 HC |
| SEQ ID NO 17 | CDR3 HC | or

| SEQ ID NO 29 | CDR1 HC |
| SEQ ID NO 30 | CDR2 HC |
| SEQ ID NO 31 | CDR3 HC |

In another preferred embodiment, the antibody comprises at least the 3 CDR sequences:

| SEQ ID NO 4 | CDR1 LC |
| SEQ ID NO 5 | CDR2 LC |
| SEQ ID NO 6 | CDR3 LC | or

| SEQ ID NO 18 | CDR1 LC |
| SEQ ID NO 19 | CDR2 LC |
| SEQ ID NO 20 | CDR3 LC | or

| SEQ ID NO 32 | CDR1 LC |
| SEQ ID NO 33 | CDR2 LC |
| SEQ ID NO 34 | CDR3 LC |

In both cases, it is to be understood that the definition of the CDR ("Complementarity Determining Region") is based on the "IMGT unique numbering for all IG and TR V-REGIONs of all species: interest for structure and evolution". Further, "CDR LC" means Light Chain CDR, while "CDR HC" means Heavy Chain CDR.

In a preferred embodiment, the antibody comprises at least one heavy chain or light chain variable region sequence that is 95% identical, preferably 96 or even 97% identical, more preferably 98% or even 99% identical, and most preferably 100% to a sequence selected from the group consisting of:

| SEQ ID NO 9 | VR HC |
| SEQ ID NO 10 | VR LC |
| SEQ ID NO 11 | VR HC |
| SEQ ID NO 12 | VR LC |
| SEQ ID NO 13 | VR HC |
| SEQ ID NO 14 | VR LC |
| SEQ ID NO 23 | VR HC |
| SEQ ID NO 24 | VR LC |
| SEQ ID NO 25 | VR HC |
| SEQ ID NO 26 | VR LC |
| SEQ ID NO 27 | VR HC |
| SEQ ID NO 28 | VR LC |
| SEQ ID NO 37 | VR HC |
| SEQ ID NO 38 | VR LC |
| SEQ ID NO 39 | VR HC |
| SEQ ID NO 40 | VR LC |
| SEQ ID NO 41 | VR HC |
| SEQ ID NO 42 | VR LC |
| SEQ ID NO 43 | VR HC |
| SEQ ID NO 44 | VR LC |

"VR HC" means Heavy Chain Variable Sequence, while "VR LC" means Light Chain Variable Sequence.

In a preferred embodiment, the antibody is humanized from
mouse anti ROR antibody mAb 2A2,
rabbit anti ROR antibody mAb R11, and/or
rabbit anti ROR antibody mAb R12,
and/or is selected from the group consisting of
hu2A2b-Q11 (also called msQ11-3)
hu2A2-D23 (also called msD23-19)
hu2A2-D16 (also called msD16-7)
preferably, but not limited to having better than 11 nM affinity
rbQ11 (also called rbQ11-32)
rbD4 (also called rbD4-32)
rbQ12 (also called rbQ12-40)
preferably, but not limited to having better than 15 nM affinity
huR12-4
huR12-7
huR12-11, and/or
huR12-16
and/or antibodies sharing at least 95%, preferably 96 or even 97% identical, more preferably 98% or even 99% identical, and most preferably 100% amino acid sequence identify with any of the antibodies mentioned above.

In one embodiment, the antibody has an affinity of better than 1.0 nM to human ROR1.

In one other embodiment, the antibody humanized from rabbit anti ROR antibody mAb R12 has a better affinity than its parent, i.e., rabbit monoclonal antibody R12.

In a preferred embodiment, the antibody has at least one of the characteristics set forth in Table 1 or Table 2.

According to yet another embodiment of the invention, a human or humanized antibody is provided, or an antibody-based binding protein, modified antibody format retaining target binding capacity, antibody derivative or fragment retaining target binding capacity, which
(i) has a binding affinity for ROR1 that is at least as high or substantially as high as the binding affinity of an antibody, antibody-based binding protein, modified antibody format, antibody derivative or fragment according to any of the antibodies described above, and/or
(ii) competes with an antibody, antibody-based binding protein, modified antibody format, antibody derivative or fragment according to any of the antibodies described above for binding to ROR1.

In one embodiment of the antibody, antibody-based binding protein, modified antibody format, antibody derivative or fragment according to the above description, the Receptor tyrosine kinase-like orphan receptor-1 (ROR1) is human ROR1.

According to another embodiment of the invention, the antibody-based binding protein, modified antibody format, antibody derivative or fragment of any of the aforementioned claims is a bispecific antibody or a multispecific antibody.

The terms "bispecific antibody" and "multispecific antibody" refers to an antibody having the capacity to bind to two, or more, distinct epitopes either on a single antigen or two different antigens, out of which one is ROR1. Bispecific antibodies of the present invention can be produced via biological methods, such as somatic hybridization; or genetic methods, such as the expression of a non-native DNA sequence encoding the desired antibody structure in an organism; chemical methods, such as chemical conjugation of two antibodies; or a combination thereof (Kontermann, R. E. In: Bispecific Antibodies. Kontermann R E (ed.), Springer Heidelberg Dordrecht London New York, pp. 1-28 (2011)).

Chemically conjugated bispecific antibodies arise from the chemical coupling of two existing antibodies or antibody fragments. Typical couplings include cross-linking two different full-length antibodies, cross-linking two different Fab' fragments to produce a bispecific F(ab')2, and cross-linking a F(ab')2 fragment with a different Fab' fragment to produce a bispecific F(ab')3. For chemical conjugation, oxidative reassociation strategies can be used. Current methodologies include the use of the homo- or heterobifunctional cross-linking reagents (Id.). Heterobifunctional cross-linking reagents have reactivity toward two distinct reactive groups on, for example, antibody molecules. Examples of heterobifunctional cross-linking reagents include SPDP (N-succinimidyl-3-(2-pyridyldithio)propionate), SATA (succinimidyl acetylthioacetate), SMCC (succinimidyl trans-4-(maleimidylmethyl) cyclohexane-1-carboxylate), EDAC (1-ethyl-3-(3-dimethylaminopropyl) carbodiimide), PEAS (N-((2-pyridyldithio)ethyl)-4-azidosalicylamide), ATFB, SE (4-azido-2,3,5,6-tetrafluorobenzoic acid, succinimidyl ester), benzophenone-4-maleimide, benzophenone-4-isothiocyanate, 4-benzoylbenzoic acid, succinimidyl ester, iodoacetamide azide, iodoacetamide alkyne, Click-iT maleimide DIBO alkyne, azido (PEO)4 propionic acid, succinimidyl ester, alkyne, succinimidyl ester, Click-iT succinimidyl ester DIBO alkyne, Sulfo-SBED (Sulfo-N-hydroxysuccinimidyl-2-(6-[biotinamido]-2-(p-azido benzamido)-hexanoamido) ethyl-1,3'-dithioproprionate), photoreactive amino acids {e.g., L-Photo-Leucine and L-Photo-Methionine), NHS-haloacetyl crosslinkers such as, for example, Sulfo-SIAB, SIAB, SBAP, SIA, NHS-maleimide crosslinkers such as, for example, Sulfo-SMCC, SM(PEG)n series crosslinkers, SMCC, LC-SMCC, Sulfo-EMCS, EMCS, Sulfo-GMBS, GMBS, Sulfo-KMUS, Sulfo-MBS, MBS, Sulfo-SMPB, SMPB, AMAS, BMPS, SMPH, PEG12-SPDP, PEG4-SPDP, Sulfo-LC-SPDP, LC-SPDP, SMPT, DCC (N, N'-Dicyclohexylcarbodiimide), EDC (1-Ethyl-3-(3-dimethylaminopropyl) carbodiimide), NHS (N-hydroxysuccinimide), Sulfo-NHS (N-hydroxysulfosuccinimide), BMPH, EMCH, KMUH, MPBH, PDPH, and PMPI.

Homobifunctional cross-linking reagents have reactivity toward the same reactive group on a molecule, for example, an antibody. Examples of homobifunctional cross-linking reagents include DTNB (5,5'-dithiobis(2-nitrobenzoic acid), o-PDM (o-phenylenedimaleimide), DMA (dimethyl adipimidate), DMP (dimethyl pimelimidate), DMS (dimethyl suberimidate), DTBP (dithiobispropionimidate), BS(PEG)5, BS(PEG)9, BS3, BSOCOES, DSG, DSP, DSS, DST, DTSSP, EGS, Sulfo-EGS, TSAT, DFDNB, BM(PEG)n crosslinkers, BMB, BMDB, BMH, BMOE, DTME, and TMEA. [0030] Somatic hybridization is the fusion of two distinct hybridoma (a fusion of B cells that produce a specific antibody and myeloma cells) cell lines, producing a quadroma capable of generating two different antibody heavy (VHA and VHB) and light chains (VLA and VLB). (Kontermann, R. E. In: Bispecific Antibodies. Kontermann R E (ed.), Springer Heidelberg Dordrecht London New York, pp. 1-28 (2011)). These heavy and light chains combine randomly within the cell, resulting in bispecific antibodies (a VHA combined with a VLA and a VHB combined with a VLB), as well as some nonfunctional (e.g. two VHAs combined with two VLBs) and monospecific (two VHAs combined with two VLAs) antibodies. The bispecific antibodies can then be purified using, for example, two different affinity chromatography columns. Similar to monospecific antibodies, bispecific antibodies may also contain an Fc region that elicits Fc-mediated effects downstream of antigen binding. These effects may be reduced by, for example, proteolytically cleaving the Fc region from the bispecific antibody by pepsin digestion, resulting in bispecific F(ab')2 molecules (Id.).

Bispecific antibodies may also be generated via genetic means, e.g., in vitro expression of a plasmid containing a DNA sequence corresponding to the desired antibody structure. See, e.g., Kontermann, R. E. In: Bispecific Antibodies. Kontermann R E (ed.), Springer Heidelberg Dordrecht London New York, pp. 1-28 (2011). Such bispecific antibodies are discussed in greater detail below.

A bispecific antibody of the present invention may be bivalent, trivalent, or tetravalent. As used herein, "valent", "valence", "valencies", or other grammatical variations thereof, mean the number of antigen binding sites in an antibody molecule.

Further provided are
a) an isolated nucleic acid sequence, or a set thereof, that encodes an antibody, antibody-based binding protein, modified antibody format, antibody derivative or fragment according to the above description, or a bispecific antibody or a multispecific antibody according to the above description,
b) a vector comprising at least one such nucleic acid sequence,
c) an isolated cell expressing an antibody, antibody-based binding protein, modified antibody format, antibody derivative or fragment according to the above description, or a bispecific antibody or a multispecific antibody according to the above description,
d) and/or comprising a nucleic acid sequence, or a set thereof, according to the above description, or a vector according to the above description, and
e) a method of producing an antibody, antibody-based binding protein, modified antibody format, antibody derivative or fragment according to the above description, comprising culturing of a cell according to the above description, and purification of the antibody, antibody-based binding protein, modified antibody format, antibody derivative or fragment.

According to another aspect of the invention, an Immunoligand-Drug Conjugate having the general formula A-(L)n-(T)m is provided, in which
A is an Immunoligand targeting Receptor tyrosine kinase-like orphan receptor-1 (ROR1),
L is a linker,
T is a toxin
and in which n and m are integers between $\geq 1$ and $\leq 10$ In this construct, (L)n can mean several linkers which form a unitary chain that conjugates one toxin to the one Immunoligand, and/or several linkers which connect several toxins to the one Immunoligand. Likewise, (L)n can mean several linkers which conjugate two Subdomains of the same Immunoligand to two toxin molecules.

| Several linkers which form a unitary chain | Several linkers which connect several toxins to the one Immunoligand. | Several linkers which conjugate two subdomains (SD1, SD2) of the same Immunoligand to two toxin molecules |
|---|---|---|
| A-$L_1$-[ . . . ]-$L_n$-T | T-$L_1$-A-$L_1$-T | $A_{SD1}$-$L_1$-T<br>$A_{SD2}$-$L_1$-T |

The resulting Immunoligand-Toxin-Conjugate would thus have a Toxin/Immunoligand ratio of $\geq 1$ and $\leq 10$. Preferably, n and m are integers between $\geq 1$ and $\leq 4$. The resulting Immunoligand-Toxin-Conjugate would thus have an Toxin/Immunoligand ratio of $\geq 1$ and $\leq 4$.

As used herein, the term "immunoligand" is meant to define an entity, an agent or a molecule that has affinity to a given target, e.g., a receptor, a cell surface protein, a cytokine or the like. Such Immunoligand may optionally block or dampen agonist-mediated responses, or inhibit receptor-agonist interaction. Most importantly, however, the immunoligand may serve as a shuttle to deliver a payload to a specific site, which is defined by the target recognized by said immunoligand. Thus, an Immunoligand targeting a receptor, delivers its payload to a site which is characterized by abundance of said receptor.

In a further preferred embodiment, the Immunoligand is at least one selected from the group consisting of an
antibody,
antibody-based binding protein
modified antibody format retaining target binding capacity,
antibody derivative or fragment retaining target binding capacity, and/or
bispecific antibody or a multispecific antibody.

"Antibodies", also synonymously called "immunoglobulins" (Ig), are generally comprising four polypeptide chains, two heavy (H) chains and two light (L) chains, and are therefore multimeric proteins, or an equivalent Ig homologue thereof (e.g., a camelid antibody, which comprises only a heavy chain, single domain antibodies (dAbs) which can be either be derived from a heavy or light chain); including full length functional mutants, variants, or derivatives thereof (including, but not limited to, murine, chimeric, humanized and fully human antibodies, which retain the essential epitope binding features of an Ig molecule, and including dual specific, bispecific, multispecific, and dual variable domain immunoglobulins; Immunoglobulin molecules can be of any class (e.g., IgG, IgE, IgM, IgD, IgA, and IgY), or subclass (e.g., IgG1, IgG2, IgG3, IgG4, IgA1, and IgA2) and allotype.

An "antibody-based binding protein", as used herein, may represent any protein that contains at least one antibody-derived $V_H$, $V_L$, or $C_H$ immunoglobulin domain in the context of other non-immunoglobulin, or non-antibody derived components. Such antibody-based proteins include, but are not limited to (i) Fc-fusion proteins of binding proteins, including receptors or receptor components with all or parts of the immunoglobulin $C_H$ domains, (ii) binding proteins, in which $V_H$ and or $V_L$ domains are coupled to alternative molecular scaffolds, or (iii) molecules, in which immunoglobulin $V_H$, and/or $V_L$, and/or $C_H$ domains are combined and/or assembled in a fashion not normally found in naturally occurring antibodies or antibody fragments.

An "antibody drug conjugate" (ADC), as used herein, relates to either an antibody, or an antibody fragment, or an antibody-based binding protein, coupled to a small molecular weight active pharmaceutical ingredient (API), including, but not limited to a toxin (including e.g., but not limited to, tubulin inhibitors, actin binders, RNA polymerase inhibitors, DNA-intercalating and modifying/damaging drugs), a kinase inhibitor, or any API that interferes with a particular cellular pathway that is essential for the survival of a cell and/or essential for a particular physiologic cellular pathway.

An "antibody derivative or fragment", as used herein, relates to a molecule comprising at least one polypeptide chain derived from an antibody that is not full length, including, but not limited to (i) a Fab fragment, which is a monovalent fragment consisting of the variable light (V$_L$), variable heavy (V$_H$), constant light (C$_L$) and constant heavy 1 (C$_H$I) domains; (ii) a F(ab')2 fragment, which is a bivalent fragment comprising two Fab fragments linked by a disulfide bridge at the hinge region; (iii) a heavy chain portion of a F$_{ab}$ (Fa) fragment, which consists of the V$_H$ and C$_H$I domains; (iv) a variable fragment (F$_v$) fragment, which consists of the V$_L$ and V$_H$ domains of a single arm of an antibody, (v) a domain antibody (dAb) fragment, which comprises a single variable domain; (vi) an isolated complementarity determining region (CDR); (vii) a single chain F$_v$ Fragment (scF$_v$); (viii) a diabody, which is a bivalent, bispecific antibody in which V$_H$ and V$_L$ domains are expressed on a single polypeptide chain, but using a linker that is too short to allow for pairing between the two domains on the same chain, thereby forcing the domains to pair with the complementarity domains of another chain and creating two antigen binding sites; (ix) a linear antibody, which comprises a pair of tandem F$_v$ segments (V$_H$-C$_H$1-V$_H$-C$_H$1) which, together with complementarity light chain polypeptides, form a pair of antigen binding regions; (X) Dual-Variable Domain Immunoglobulin (xI) other non-full length portions of immunoglobulin heavy and/or light chains, or mutants, variants, or derivatives thereof, alone or in any combination.

The term "modified antibody format", as used herein, encompasses antibody-drug-conjugates, Polyalkylene oxide-modified scFv, Monobodies, Diabodies, Camelid Antibodies, Domain Antibodies, bi- or trispecific antibodies, IgA, or two IgG structures joined by a J chain and a secretory component, shark antibodies, new world primate framework+non-new world primate CDR, IgG4 antibodies with hinge region removed, IgG with two additional binding sites engineered into the CH3 domains, antibodies with altered Fc region to enhance affinity for Fc gamma receptors, dimerised constructs comprising CH3+VL+VH, and the like. The term "antibody mimetic", as used herein, refers to proteins not belonging to the immunoglobulin family, and even non-proteins such as aptamers, or synthetic polymers. Some types have an antibody-like beta-sheet structure. Potential advantages of "antibody mimetics" or "alternative scaffolds" over antibodies are better solubility, higher tissue penetration, higher stability towards heat and enzymes, and comparatively low production costs.

Another preferred embodiment is an Immunoligand comprising at least one antibody or antibody fragment with binding capacity to ROR1 as set forth in the above disclosure.

An "Immunoligand-Drug Conjugate" (IDC), as used herein, relates to a molecule that comprises a binding moiety of a humanized anti ROR1 antibody or antibody-based binding protein as disclosed herein, coupled to a small molecular weight active pharmaceutical ingredient (API), including, but not limited to a toxin (including e.g., but not limited to, tubulin inhibitors, actin binders, RNA polymerase inhibitors, DNA-intercalating and modifying/damaging drugs), a kinase inhibitor, or any API that interferes with a particular cellular pathway that is essential for the survival of a cell and/or essential for a particular physiologic cellular pathway.

Another preferred embodiment is an Immunoligand-Drug Conjugate as disclosed above comprising covalent a linker between an Immunoligand and preferably a small molecular weight active pharmaceutical ingredient (API).

In another preferred embodiment, said linker is at least one selected from the group consisting of an oligopeptide linker, optionally comprising cleavable spacers, that may be cleaved by changes in pH, redox potential and or specific intracellular enzymes and/or a maleimide linker, optionally comprising cleavable spacers, that may be cleaved by changes in pH, redox potential and or specific intracellular enzymes In a preferred embodiment, the linker comprises, or consists of, at least one selected from the group consisting of: an oligopeptide linker (including cleavable and non-cleavable oligopeptide linkers), a hydrazine linker, a thiourea linker, a self-immolative linker, a succinimidyl trans-4-(maleimidylmethyl)cyclohexane-1-carboxylate (SMCC) linker, a maleimide linker, a disulfide linker, a thioether linker, and/or a maleimide linker.

The skilled person understands that further linkers may be suitable. Such linkers may be non-cleavable or may be cleaved by changes in pH, redox potential or specific intracellular or tumor tissue associated enzymes. Cleavable oligopeptide linkers include protease- or matrix metalloprotease-cleavable linkers. It is understood that the linker may comprise combinations of the above. For example, the linker may be a valine-citruline PAB linker.

In a preferred embodiment, the linker comprises an oligopeptide that is recognized by sortase enzymes, including but not limited to amino acid sequences selected from LPXSGn (SEQ ID NO: 65), LPXAGn (SEQ ID NO: 66), LPXTGn (SEQ ID NO: 67), LAXTGn (SEQ ID NO: 68), LAETGn (SEQ ID NO: 69), LPXTAn (SEQ ID NO: 70) or NPQTGn (SEQ ID NO: 71) with n being an integer between >1 and <21, and X being any amino acid.

In still another preferred embodiment, the linker comprises an oligopeptide of the sequence LPXTGn (SEQ ID NO: 67) with n being an integer between ≥1 and ≤20, and X being any naturally occurring amino acid.

In another preferred embodiment, the linker is conjugated to the C-terminus of at least one subdomain of the Immunoligand.

In another preferred embodiment, prior to conjugation, the immunoligand bears a sortase recognition tag used or conjugated to the C-terminus of at least one subdomain thereof, and the toxin comprises a short glycine stretch with a length of 1-20 glycine residues, preferably with a length of 3 to 5 amino acids.

Preferably, the sortase recognition tag is:

LPXTG (SEQ ID NO: 58) or LPXAG (SEQ ID NO: 59), which is recognized by *Staphylococcus aureus* sortase A;

LPXSG (SEQ ID NO: 60), which is recognized by *Staphylococcus aureus* sortase A or an engineered sortase A 4S-9 from *Staphylococcus aureus;*

LAXTG (SEQ ID NO: 61), and particularly LAETG (SEQ ID NO: 62), which is recognized by engineered sortase A 2A-9 from *Staphylococcus aureus;*

LPXTA (SEQ ID NO: 63), which is recognized by *Streptococcus pyogenes* sortase A; or NPQTN (SEQ ID NO: 64) which is recognized by *Staphylococcus aureus* sortase B.

The following table shows the recognition tags and the peptides derived therefrom to be part of the linker (with n being an integer between ≥1 and ≤21, and X being any amino acid):

| Sortase type | "naked" recognition tag | peptide that eventually appears in the linker |
|---|---|---|
| *Staphylococcus aureus* sortase A | LPXTG (SEQ ID NO: 58) | LPXTG$_n$ (SEQ ID NO: 65) |
| | LPXAG (SEQ ID NO: 56) | LPXAG$_n$ (SEQ ID NO: 66) |
| *Staphylococcus aureus* sortase A or an engineered sortase A 4S-9 from *Staphylococcus aureus* | LPXSG (SEQ ID NO: 60) | LPXSG$_n$ (SEQ ID NO: 67) |
| engineered sortase A 2A-9 from *Staphylococcus aureus* | LAXTG (SEQ ID NO: 61) | LAXTG$_n$ (SEQ ID NO: 68) |
| | LAETG (SEQ ID NO: 62) | LAETG$_n$ (SEQ ID NO: 69) |
| *Streptococcus pyogenes* sortase A | LPXTA (SEQ ID NO: 63) | LPXTA$_n$ (SEQ ID NO: 70) |
| *Staphylococcus aureus* sortase B | NPQTN (SEQ ID NO: 64) | NPQTG$_n$ (SEQ ID NO: 71) |

Engineered sortases, including A 2A-9 and A 4S-9 from *Staphylococcus aureus*, are described in Dorr B M et al., PNAS 2014; 111, 13343-8, and Chen et al., PNAS 2011; 108(28); 11399-11404.

As background and to exemplify the general concept of sortase transpeptidation, Sortase A, for example, uses an oligo-glycine-stretch as a nucleophile to catalyze a transpeptidation by which the terminal amino group of the oligo-glycine effects a nucleophilic attack on the peptide bond joining the last two C-terminal residues of the sortase tag. This results in breakage of that peptide bond and the formation of a new peptide bond between the C-terminally second-to-last residue of the sortase tag and the N-terminal glycine of the oligo-glycine peptide, i.e. resulting in a transpeptidation.

Prior to sortase conjugation, the sortase tag may, at its C-terminus, furthermore carry other tags, like His-tags, Myc-tags or Strep-Tags® (see FIG. 4a of WO2014/140317, the content of which is incorporated by reference herein). However, because the peptide bond between the 4th and 5th amino acid of the sortase tag is cleaved upon sortase A mediated conjugation, these additional tags do not appear in the conjugated product.

Sortase tag may, for example, be fused to a C-terminus of a binding protein, or to a domain or subunit thereof, by genetic fusion, and are co-expressed therewith. In another preferred embodiment, the sortase tag may directly be appended to the last naturally occurring C-terminal amino acid of the immunoglobulin light chains or heavy chains, which in case of the human immunoglobulin kappa light chain is the C-terminal cysteine residue, and which in the case of the human immunoglobulin IgG1 heavy chain may be the C-terminal lysine residue encoded by human Fcγ1 cDNA. However, another preferred embodiment is also to directly append the sortase tag to the second last C-terminal glycine residue encoded by human Fcγ1 cDNA, because usually terminal lysine residues of antibody heavy chains are clipped off by posttranslational modification in mammalian cells. Therefore, in more than 90% of the cases naturally occurring human IgG1 lacks the C-terminal lysine residues of the IgG1 heavy chains.

Therefore, one preferred embodiment of the invention is to omit the C-terminal lysine amino acid residues of human IgG1 heavy chain constant regions in expression constructs for sortase recognition-motif tagged Igγ1 heavy chains. Another preferred embodiment is to include the C-terminal lysine amino acid residues of human IgG1 heavy chain constant regions in expression constructs for sortase recognition-motif tagged Igγ1 heavy chains.

In another preferred embodiment the sortase tag may be appended to the C-terminus of a human immunoglobulin IgG1 heavy chain where the C-terminal lysine residue encoded by human Fcγ1 cDNA is replaced by an amino acid residue other than lysine to prevent unproductive reactions of sortase with the ε-amino group of said C-terminal lysine residue leading to inter-heavy chain crosslinking.

We have described previously that in some cases (e.g. at the C-terminus of the Ig kappa light chains, see: Beerli et al. (2015) PloS One 10, e131177) it is beneficial to add additional amino acids between the C-terminus of the binding protein and the sortase tag. This has been shown to improve sortase enzyme conjugation efficiencies of payloads to the binding protein. In the case of Ig kappa light chains, it was observed that by adding 5 amino acids between the last C-terminal cysteine amino acid of the Ig kappa light chain and the sortase pentapeptide motif improved the kinetic of conjugation, so that the C-termini of Ig kappa light chains and Ig heavy chains could be conjugated with similar kinetics (see: Beerli et al. (2015) PloS One 10, e131177). Therefore, it is another preferred embodiment that optionally ≥1 and ≤11 amino acids are added in between the last C-terminal amino acid of a binding protein or antibody subunit and the sortase tag.

Figure 2A:
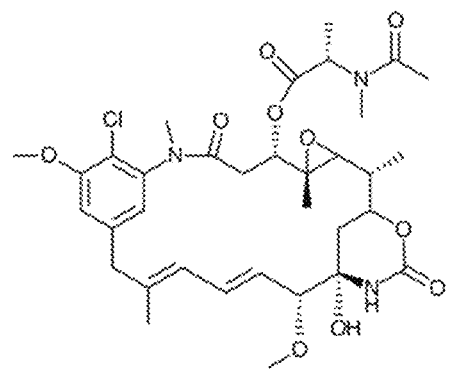
Figure 2B:
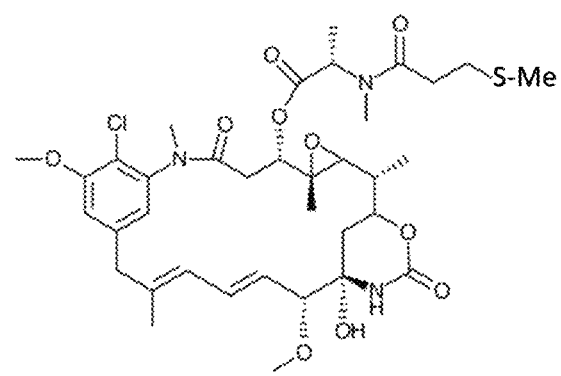
Figure 2C:
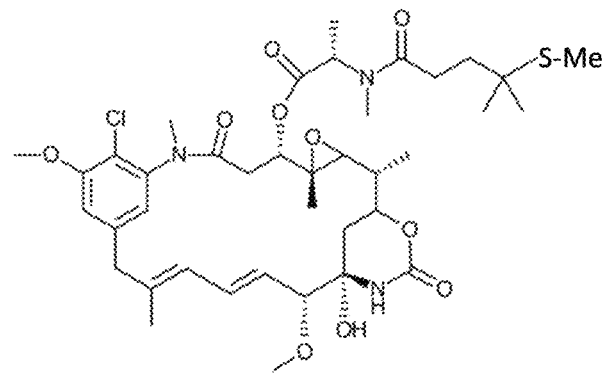
Figure 3:
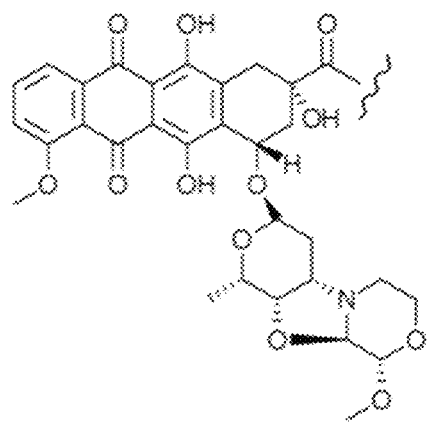
Figure 3:
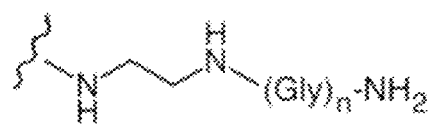

Further, the immunoligand can comprise, C-terminally of the sortase tag, other tags, like for instance, but not limited to a His tag, a Myc tag and/or a StrepII tag. See WO2014140317 A2 for more details, the subject matter of which is incorporated by reference herein In another preferred embodiment, the toxin is at least one selected from the group consisting of
    maytansinoids,
    auristatins,
    anthracyclins, preferably PNU-derived anthracyclins
    calicheamicins,
    tubulysins
    duocarmycins
    radioisotopes
    liposomes comprising a toxin payload,
    protein toxins
    taxanes, and/or
    pyrrolbenzodiazepines
Examples for preferred maytansinoid toxins are shown in FIGS. 1 and 2. The anthracycline derivatives disclosed herein also referred to as "PNU" are derivatives of PNU-159682, which is a metabolite of the anthracycline nemorubicin and has for the first time been disclosed by Quintierei et al. 2005. PNU-159682 is shown FIG. 5. A preferred anthracycline derivative is depicted in FIG. 3 (*a*).

Immunoligand Drug Conjugates comprising anthracycline derivatives are disclosed in WO2016102697 and applications claiming the priority thereof, the content of which is incorporated by reference herein.

Preferably, the Immunoligand-Drug Conjugates comprises two or more different toxins. In such way, the cell killing activity can be enhanced, by avoiding resistances against single toxins comprised in the Immunoligand-Drug Conjugates In another preferred embodiment, the Immunoligand-Drug Conjugate has a cell killing activity as set forth in FIG. 8 or FIG. 12.

In another embodiment, the Immunoligand-Drug Conjugate is created by sortase-mediated conjugation of (i) an Immunoligand carrying one or more sortase recognition tags and (ii) one or more toxins carrying an oligoglycine tag.

According to another aspect of the invention, a method of producing an Immunoligand-Drug Conjugate according to any of the aforementioned disclosure is provided, which method comprises the following steps:
a) providing an Immunoligand according to the list set forth above, which Immunoligand carries a sortase recognition tag,
b) providing one or more toxins carrying an oligoglycine tag, and
c) conjugating the Immunoligand and the toxin by means of sortase-mediated conjugation.

The method of conjugating an Immunoligand to a payload by means of a sortase or a split intein is disclosed in full detail in WO2014140317, the subject matter of which is incorporated by reference herein.

According to yet another embodiment, a ROR1 specific chimeric antigen receptor (CAR) is provided, comprising
a) at least one antibody, antibody-based binding protein, modified antibody format or antibody derivative or fragment according to the above description, or
b) a bi- or multispecific antibody according to the above description,
which is fused or conjugated to at least one transmembrane region and at least one intracellular domain.

Chimeric antigen receptors (CAR), sometimes also called artificial T cell receptors, are engineered receptors, which graft an arbitrary specificity onto an immune effector cell.

Typically, these receptors are used to graft the specificity of a monoclonal antibody onto a T cell; with transfer of their coding sequence facilitated by retroviral vectors. The receptors are called chimeric because they are composed of parts from different sources.

CARs are potential candidates as a therapy for cancer, using a technique called adoptive cell transfer. T cells are removed from a patient and modified so that they express CARs specific to the patient's particular cancer, by specifically binding to a cancer-specific antigen, as is the case in ROR1. The T cells, which can then recognize and kill the cancer cells, are reintroduced into the patient.

The structure of the prototypic CAR is modular, designed to accommodate various functional domains and thereby to enable choice of specificity and controlled activation of T cells. In the context of the present invention, a CAR comprises an antibody-like binding domain derived from an antibody, antibody-based binding protein, modified antibody format, antibody derivative or fragment, which targets ROR1. Such entity can be, e.g., but is not limited to, a single chain variable fragment (scFv) that combines the specificity and binding residues of both the heavy and light chain variable regions of a monoclonal antibody in a single polypeptide chain, fused or conjugated to at least one transmembrane region and at least one intracellular domain.

Preferably, said transmembrane region comprises a CD8a transmembrane domain. Preferably, said CAR further comprises a hinge region disposed between the transmembrane domain and the antibody, antibody-based binding protein, modified antibody format retaining target binding capacity, or antibody derivative. Preferably, said intracellular domain comprises a T-cell receptor signaling domain. More preferably, said signaling domain comprises or is derived from a zeta chain of a CD3-zeta chain. Preferably, said intracellular domain further comprises one or more intracellular signaling domain of a T cell costimulatory molecule.

A preferred intracellular signaling domain of a T cell costimulatory molecule is selected from the group consisting of 4-1BB, CD-28, OX40 and/or CD278/ICOS. Combination of two or more of these domains are specifically preferred.

According to another embodiment of the invention, a cell comprising such chimeric antigen receptor is provided.

Said cell is preferably an engineered T cell, also called "CAR T cell". CAR T cells are genetically engineered T cells armed with CARs whose extracellular recognition unit is comprised of an antibody-derived recognition domain and whose intracellular region is derived from lymphocyte stimulating moiety(ies). By arming T cells with such chimeric receptors, the engineered cell is redirected with a predefined specificity to any desired target antigen, in a non-HLA restricted manner. CAR constructs are introduced ex vivo into T cells from peripheral lymphocytes of a given patient using retroviral or lentiviral vectors or transposable elements. Following infusion of the resulting CAR-engineered T cells back into the patient, they traffic, reach their target site, and upon interaction with their target cell or tissue, they undergo activation and perform their predefined effector function. Therapeutic targets for the CAR approach include cancer and HIV-infected cells, or autoimmune effector cells. Alternatively, said cell is preferably an engineered natural killer cell (NK cell).

Another aspect of the invention is the use of the antibody-based binding protein, modified antibody format retaining target binding capacity, antibody derivative or fragment of any of claims according to the above description, the bi- or multispecific antibody according to the above description, the Immunoligand-Drug Conjugate according to the above description, or the CAR or cell according to the above description, for the treatment of a patient that is
suffering from,
at risk of developing, and/or
being diagnosed for
a neoplastic disease.

In a preferred embodiment, the neoplastic disease is at least one selected from the group consisting of
blood cancer, such as lymphomas and leukemias, like chronic lymphocytic leukemia (CLL), acute lymphocytic leukemia (ALL), non-Hodgkin lymphomas (NHL), Mantle Cell lymphoma (MCL), acute myeloid leukemia (AML), and
solid cancers such as cancer of colon, lung, breast, ovarian and pancreatic cancers According to a further aspect of the invention, a pharmaceutical composition is provided, which comprises the antibody or antibody-based binding protein, modified antibody format retaining target binding capacity, antibody derivative or fragment according to the above description, the bi- or multispecific antibody according to the above description, the Immunoligand-Drug Conjugate according to the above description, or the CAR or cell according to the above description, together with one or more pharmaceutically acceptable ingredients.

According to a further aspect of the invention, a method of killing or inhibiting the growth of a cell expressing ROR1 in vitro or in a patient is provided, which method comprises administering to the cell a pharmaceutically effective amount or doses of (i) the antibody or antibody-based binding protein, modified antibody format retaining target binding capacity, antibody derivative or fragment according to the above description, the bi- or multispecific antibody according to the above description, the Immunoligand-Drug Conjugate according to the above description, or the CAR or cell according to the above description, or (ii) of a pharmaceutical composition according to the above description Preferably, wherein the cell expressing ROR1 is a cancer cell, preferably, blood cancer, such as lymphomas and leukemias, like chronic lymphocytic leukemia (CLL), acute lymphocytic leukemia (ALL), non-Hodgkin lymphomas (NHL), Mantle Cell lymphoma (MCL), acute myeloid leukemia (AML), or solid cancer such as cancer of colon, lung, breast, ovarian and pancreatic cancer.

Further preferably, the ROR1 is human ROR1.

EXPERIMENTS AND FIGURES

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

All amino acid sequences disclosed herein are shown from N-terminus to C-terminus; all nucleic acid sequences disclosed herein are shown 5'→3'.

EXPERIMENTAL RESULTS

Generation and Selection of Humanized Anti-ROR1 Antibodies Via Transpo-mAb Display Screening In order to humanized mouse 2A2 (Baskar S et al. (2012) mAbs 4, 1-13) and two rabbit monoclonal antibodies (R12 and R11 (Yang J et al. (2011) PLoS ONE 6, e21018) specific for the cancer cell surface marker ROR1, we have decided to humanized variable regions of said antibodies by first aligning the parental antibody sequences by proprietary algorithms to a proprietary database containing next-generation sequencing data of human variable region sequences for human IgG antibodies. Based on the proprietary algorithm, best matches were identified and CDRs of the parental mAbs were in silico grafted into selected human $V_H$ and $V_L$ frameworks. This has resulted in to the in silico prediction of 64 humanized $V_H$ sequences for the $V_H$ of mAb 2A2 and 49 humanized $V_L$ sequences for the $V_L$ of mAb 2A2. In the case of R11, 101 humanized variants of $V_H$ and 82 humanized variants of $V_L$ have been generated in silico. Lastly, 25 humanized $V_H$ and 25 humanized $V_L$ sequences were predicted in the case of R12. As described herein libraries of transposable IgG heavy and light chain expression vectors have been cloned. The vector libraries have been stably transposed into L11 host cells as described in herein in order to generate cellular libraries by transposition in which individual cells express a single combination of a humanized ROR1 IgG heavy and light chains. Based on binding of cells to ROR1 recombinant antigen by FACS (FIG. 9 (a)), individual binders were selected by single-cell FACS sorting and supernatants from individual clones were screened by SPR for high-affinity binders (FIG. 9 (b)). ROR1 affinities of sixty (2A2) and thirty (R11) cell clone supernatants were determined using single-concentration measurements. We subsequently chose to recover the sequences from those five clones for each humanization that showed the highest affinities, as described in herein. After sequence recovery and validation of individual HC/LC pairs by transient transfection into HEK293T cells and analysis of supernatants for antigen binding by ELISA, we chose to express and purify at a larger scale those three mAbs that showed the best binding (data not shown).

Figure 10:
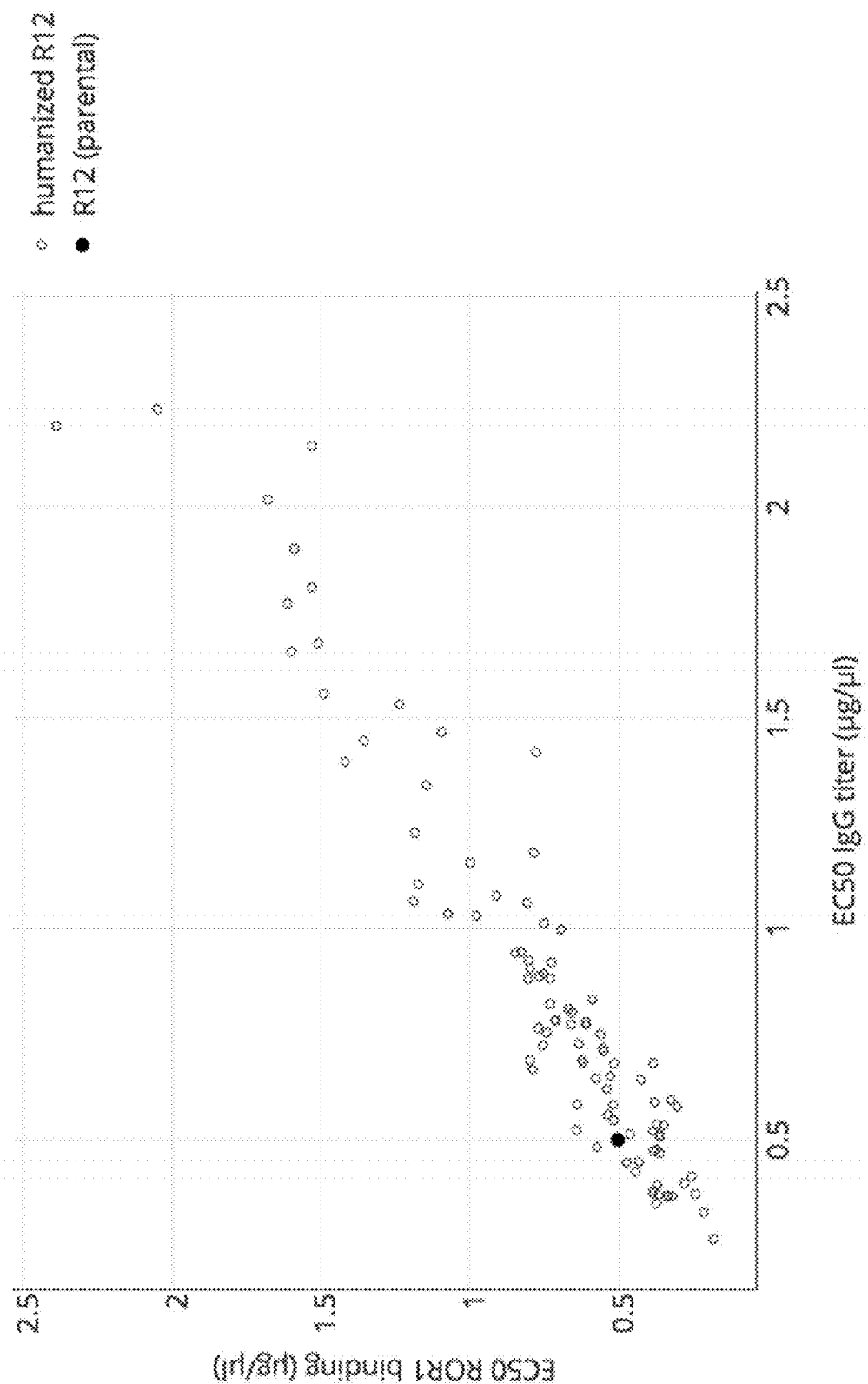

For the humanization of the R12 clone, we chose to screen L11 cell clone supernatants for most promising clones by ELISA. To rate clones according to their strength of antigen binding, we determined their individual antigen-binding: IgG-titer ratios (FIG. 10). We subsequently chose to recover the sequences from those sixteen cell clones that showed the highest antigen-binding:IgG-titer ratios, i.e. showed highest binding normalized to IgG-titer. After sequence recovery and validation of individual HC/LC pairs by transient transfection of the respective antibody expression constructs into HEK293T cells and analysis of supernatants for antigen-binding:IgG-titer ratios by ELISA, we proceeded to measure affinities of those eight mAbs that showed the highest antigen-binding:IgG-titer ratio in ELISA by surface plasmon resonance (SPR), using HEK293T supernatants obtained from transient transfections and including supernatants from HEK293T cells transiently transfected with expression constructs coding for parental mAb R12 in parallel as a reference. This analysis demonstrated that the affinities of the isolated humanized anti-ROR1 mAbs were remarkably superior to those of the parental mAb (Table 2). To confirm this observation, three humanized R12 mAbs were expressed at large scale in HEK293T cells, purified and determination of affinities by SPR was repeated with these purified mAbs (FIG. 13).

This analysis confirmed a substantial gain in monovalent affinity of humanized versus parental mAb R12 of more than 5-fold.

Figure 13:
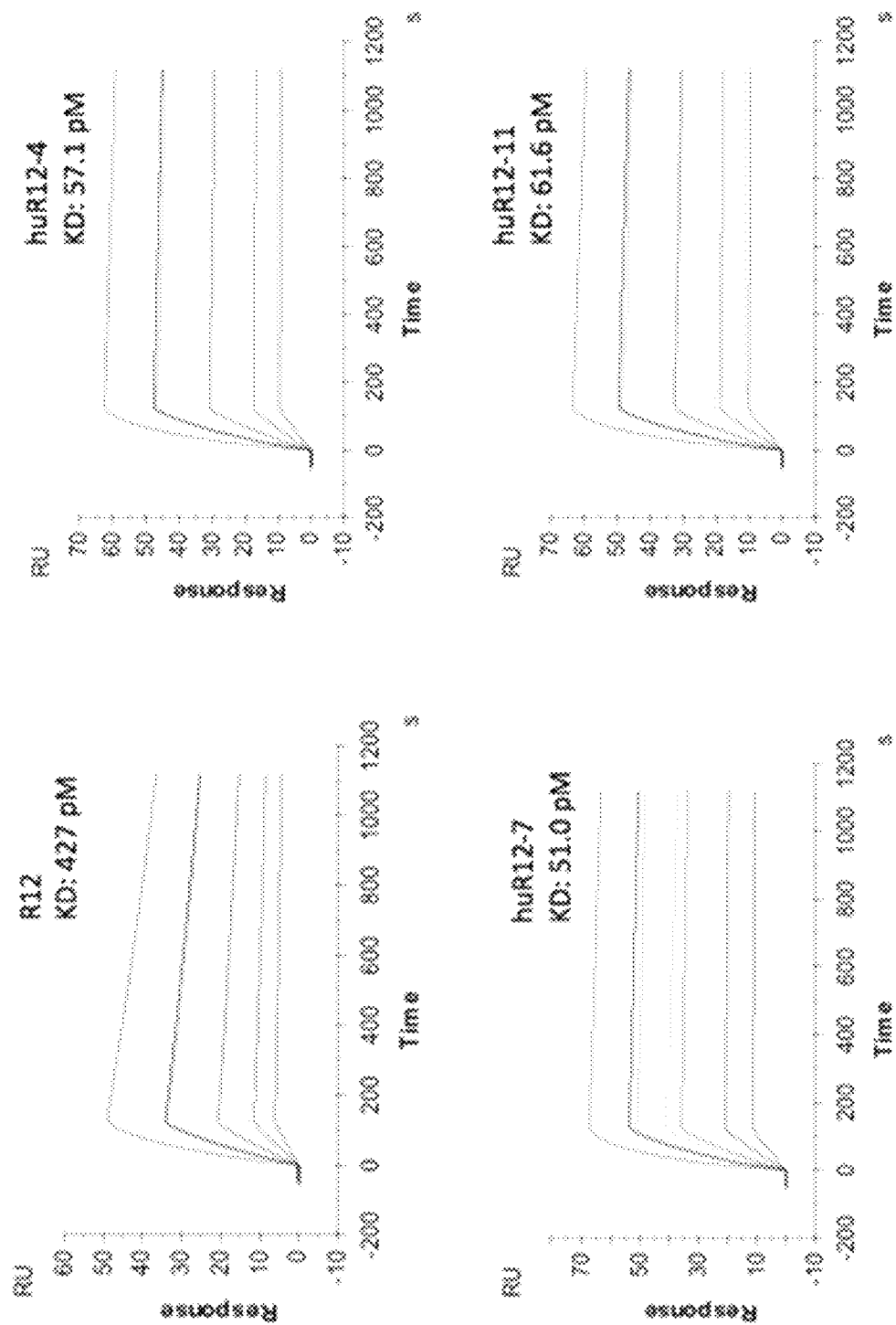

Therefore, multi-cycle Surface Plasmon Resonance (SPR) for the top humanized anti-ROR1 humanized mAbs demonstrated that the affinities of the selected humanized anti-ROR1 mAbs were in the same range of the respective parental mAbs in the case of 2A2 and R11 (FIG. 9 (c) and Table 1) or even significantly higher affine in the case of R12 (Table 2 and FIGS. 13 (a) and (b)).

This finding is extremely surprising, because, antibody humanization does regularly lead to a significant reduction or complete loss of binding affinity, which then has to be re-gained by subsequent affinity maturation.

Analysis of the Degree of Humanization

Analysis of the degree of humanization among these clones was also performed. To do so, we determined the similarity in percent of each chain's framework regions to those of the human germline sequence that was most closely related to the entire variable region sequence of the humanized mAbs (FIG. 11). Overall, the average degree of humanization of the library and isolated mAbs compared well to humanized antibodies that have been clinically approved (FIG. 11).

Evaluation of In Vitro Cell Killing Activity of ADCs with Humanized ROR1 mAbs

Figure 6:
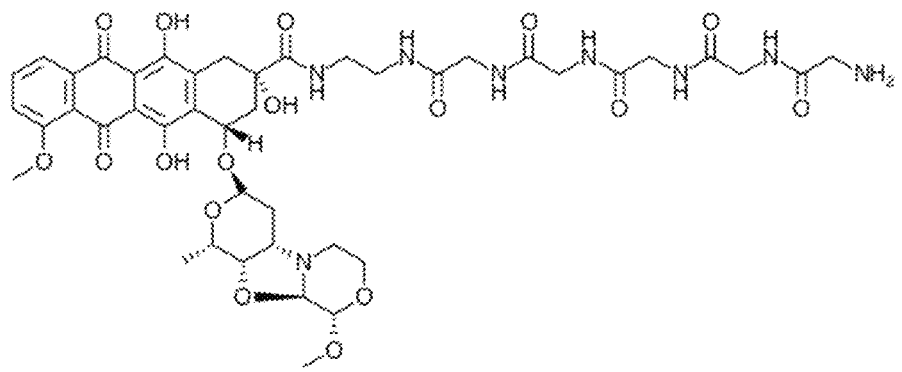

To evaluate the potency of the isolated humanized antibody clones as antibody-drug-conjugates (ADCs), antibodies were expressed and purified as LPETG-tagged versions to allow conjugation of anthracyclin-derived toxins (FIG. 6) employing SMAC-Technology™. 2A2-based anti-ROR1 antibodies conjugated to the cytostatic drug depicted in FIG. 6 (PNU-EDA-Gly$_5$) potently affected cell viability of the ROR1-positive 697 ALL cell line, while cold competition of the ADCs with unconjugated antibody significantly reduced cytotoxicity suggesting that cytotoxicity was indeed target-mediated (FIG. 8 (b)). ADCs based on humanized versions showed highly similar cell killing efficiencies as well as target-specificity. Likewise, ADCs based on parental and humanized R12 antibodies were able to specifically and potently kill ROR1-positive human 697 ALL cancer cells (FIG. 12 (b), as well as murine cancer cells overexpressing human ROR1 (EMT6-ROR1) but not the parental cell line (EMT6) not expressing human ROR1 (FIG. 12 (c)).

ADCs and their In Vivo Efficacy

Mice treated with SMAC-conjugated hu2A2b-Q11-based ADC showed prolonged survival relative to those treated with isotype control ADC (FIG. 8 (c)). In particular, the median survival time of mice treated with the hu2A2b-Q11-based ADC was of 28.3 days, whereas it was of 23.5 days in the isotype control group. No significant body weight loss difference was observed between the groups (data not shown).

EXAMPLES

The following section describes experimental details how the anti-ROR1 antibodies disclosed herein were created.

Generation of EBNA-Based Chimeric Antibody Expression Constructs

Parental anti-ROR1 mouse mAb 2A2 (Baskar S et al. (2012) mAbs 4, 1-13), rabbit mAb R12 and rabbit mAb R11 (Yang J et al. (2011) PLoS ONE 6, e21018) were produced as chimeric full-length IgG1 antibodies with human constant regions as follows. Variable region coding sequences including flanking restriction sites 5'NotI/3'-NheI ($V_H$) and NotI/BsiWI (Vkappa) or NotI/KasI (Vlambda) were produced by total gene synthesis (GenScript, Piscataway, USA) using MNFGLRLIFLVLTLKGVQC (SEQ ID NO:54) as leader sequence. Human IgH-gamma 1 and IgL-kappa (2A2 and R11) or -lambda (R12) constant region sequences for soluble antibody expression bearing appended c-terminal tags (IgH-chain-tag: LPETG-G-WSHPQFEK (SEQ ID NO:56); IgL-chain-tag: GGGGS-LPETG-G-WSHPQFEK (SEQ ID NO:57)) were produced by total gene synthesis (GenScript, Piscataway, USA) including flanking restriction sites 5'NheI/3'BstBI (IgH-gamma 1) and 5'BsiwI/3'BstBI (IgL-kappa) or 5'KasI/3'BstBI (IgL-lambda). Antibody variable and constant region fragments were double-digested individually according to their flanking restriction sites and were assembled by ligation in the expression vector pCB14b (FIG. 14) that was previously linearized by double-digestion with NotI/BstBI restriction enzymes. pCB14b is a derivative of the episomal mammalian expression vector pCEP4 (Invitrogen), carrying the EBV replication origin and encoding the EBV nuclear antigen (EBNA-1) to permit extrachromosomal replication, and contains a puromycin selection marker in place of the original hygromycin B resistance gene. FIG. 15 shows plasmid maps of the resulting pCB14b-based expression constructs for heavy chain (2A2 and R12, FIGS. 15(a) and (c), respectively), kappa light chain (2A2, FIG. 15(b)) and lambda light chain (R12, FIG. 15(d)) expression. R11 constructs (kappa light chain) are analogous to 2A2 constructs, however bearing R11 variable regions.

Expression and Purification of Antigens

StrepII-tagged ROR1-extracellular domain was produced as follows: the nucleotide sequence encoding the extracellular domain of human ROR1 (NP_005003) was N-terminally fused to a signal sequence MNFGLRLIFLVLTLKGVQC (SEQ ID NO:54) and C-terminally fused with a sequence encoding a strepII-tag GWSHPQFEK (SEQ ID NO:55) (FIG. 16). The entire nucleotide sequences with flanking 5'NotI and 3'HindIII sites were produced by total gene synthesis (GenScript, Piscataway, USA), assembled in the proprietary mammalian expression vector pEvi5 linearized by double-digest with NotI/HindIII restriction enzymes by Evitria (Schlieren, Switzerland) and verified by DNA sequencing. Expression of the proteins was performed in suspension-adapted CHO K1 cells by Evitria (Schlieren, Switzerland). Supernatants from pools of transfected CHO K1 cells were harvested by centrifugation and sterile filtered (0.2 μm) before FPLC-based affinity purification using StrepTactin columns (IBA GmbH, Goettingen, Germany).

Construction of Vectors for PiggyBac Transposon Expression of IgGs

Figure 17:
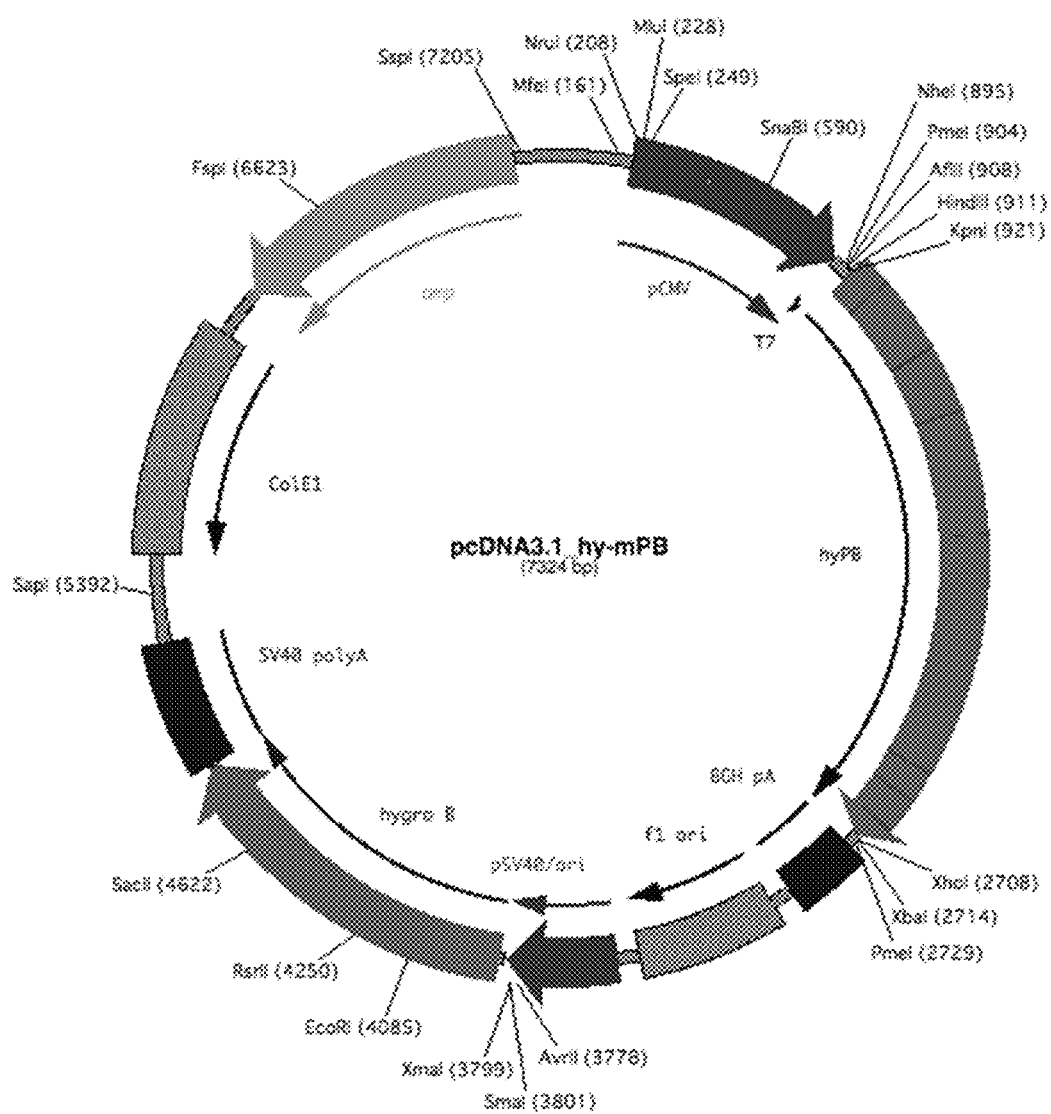

All DNA syntheses to generate plasmid backbones and antibody sequences were performed by GenScript (Piscataway, USA). The amino-acid sequence of hyperactive PiggyBac transposase (hyPB) according to (Yusa K et al. (2011) Proc Natl Acad Sci USA 108, 1531-1536) was codon-optimized for murine expression, synthesized with flanking restriction sites and cloned into the transient expression vector pcDNA3.1 (FIG. 17). Backbones for generating transposable antibody expression constructs (pPB) were assembled from modular parts with flanking restriction sites that were synthesized or derived from sequence-verified commercially available vectors, and are described in detail in Patent WO2014013026A1.

Antibody ORFs were assembled in transposable vector backbones as follows by two- or three-way cloning: antibody variable regions along with the leader sequence MNFGLRLIFLVLTLKGVQC (SEQ ID NO:54) were introduced using 5'NotI/3'NheI (IgHV) and 5'NotI/3'BsiWI (IgkappaV) or 5'NotI/3'KasI (IglambdaV) restriction sites, in-frame with constant region fragments using 5'NheI/3'BstBI (IgHC-gamma 1) or 5'BsiWI/3'BstBI (IgKC) or 5'KasI/3'BstBI (IgLC) restriction sites.

Construction of Expression Libraries for Humanized ROR-1 IgG Heavy and Light Chains Humanized framework regions for rabbit anti ROR1 antibodies R11 and R12 (Yang J et al. (2011) PLoS ONE 6, e21018) and murine anti-ROR1 antibody 2A2 (Baskar S et al. (2012) mAbs 4, 1-13) have been aligned with millions of human $V_H$ and $V_L$ sequences derived by next-generation sequencing (NGS) from healthy donors and by way of proprietary algorithms, most homologous human frameworks relative to the rodent parental mAbs have been selected. Selected frameworks have been assembled by proprietary algorithms in silico with the CDRs of the parental mAbs of rodent anti-ROR1 mAbs R11, R12, and 2A2.

The selected human variable regions along with the leader sequence MNFGLRLIFLVLTLKGVQC (SEQ ID NO; 54) were synthesized by Gen9, Inc. (Cambridge, USA).

For humanization of 2A2, 64 VH×49 VL variants were synthesized, for humanization of R11, 101 VH×82 VL variants were synthesized and for humanization of R12, 25 VH×25 VL were synthesized in total.

Aliquots of synthesized $V_H$s and $V_L$s were pooled to equimolar amounts and amplified by PCR using forward primer univ-NotI-SP-F, comprising a NotI restriction enzyme recognition site for later directional cloning of the $V_H$ and $V_L$ sequence libraries.

(SEQ ID NO: 45)
GAGGAGGCGGCCGCCATGAACTTTGGG and reverse primers huCG1-B, comprising a NheI restriction enzyme recognition site for later directional cloning of the $V_H$ sequence library.

(SEQ ID NO: 46)
AAGACCGATGGGCCCTTGGTG

Reverse Primer huCK-B

GAAGACAGATGGTGCAGCCAC (SEQ ID NO: 47)

was used as for amplification of Vκ sequence libraries, comprising a BsiWI restriction enzyme recognition site for later directional cloning of the Vκ sequence library.
Reverse Primer huCL-B

GGAAACAGAGTCACGCTTGG (SEQ ID NO: 48)

was used as for amplification of Vλ sequence libraries, comprising a KasI restriction enzyme recognition site for later directional cloning of the Vλ sequence library.

Figure 18:
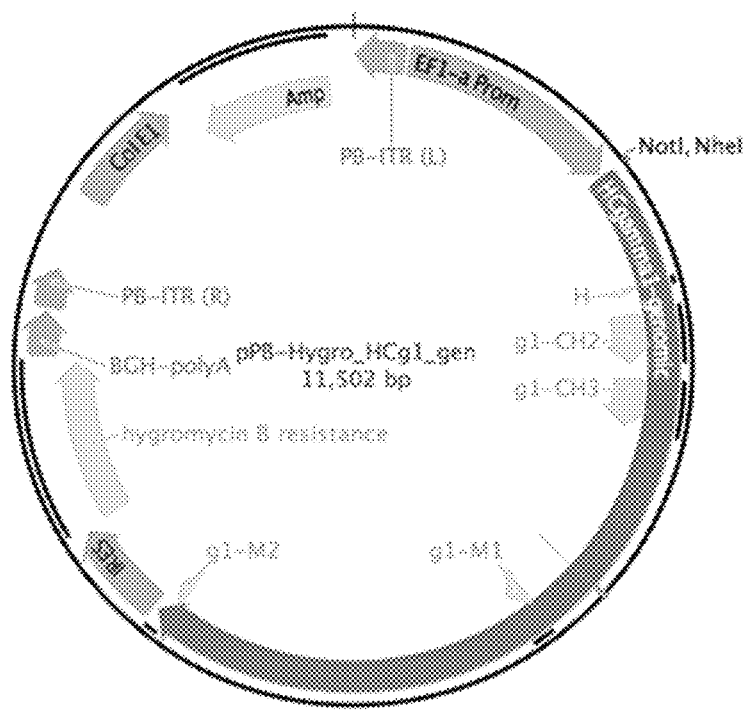
Figure 18:
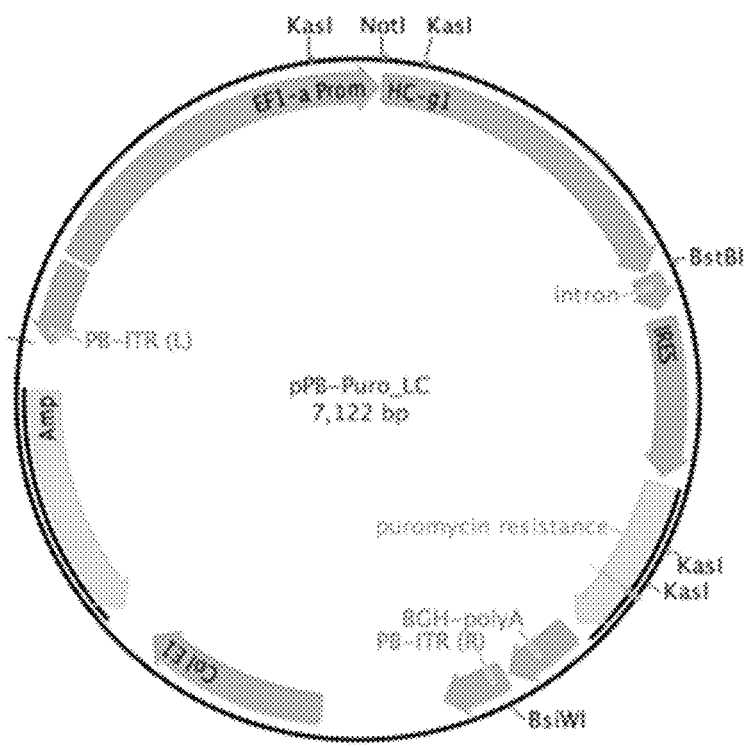

PCR amplified library fragments were column-purified, digested using NotI/NheI (IgHV) or NotI/BsiWI (IgkappaV) or NotI/KasI (IglambdaV), and cloned into transposable vectors described in above by 2-way (HC constructs) or 3-way cloning (LC constructs). Vector fragments for HC constructs were prepared by digestion of pPB-Hygro-HCg1-gen (FIG. 18 (a)) with NotI/NheI. Vector fragments for LC constructs were prepared by digestion of pPB-Puro-LC (FIG. 18 (b) with NotI/BstBI restriction enzymes. Constant region sequences including flanking restriction sites 5'BsiWI/3'-BstBI (Ckappa) and 5'KasI/3'-BstBI (Clambda) were produced by total gene synthesis and cloned into pUC57 (GenScript, Piscataway, USA). Constant region fragments for assembly of libraries were generated by digestion of DNA maxi-preps of the respective plasmids containing kappa or lambda constant regions with BsiWI/BstBI (to generate kappa constant region fragments) or KasI/BstBI (to generate lambda constant region fragments). Library ligations were transformed into Neb5-alpha electrocompetent cells (Neb, Ipswich, USA), pre-cultured for 1 hour, amplified in selective LB-media containing 0.1 mg/ml ampicillin overnight, and plasmid DNA was isolated using NucleoBond Xtra Maxi Plus kit (Macherey&Nagel, Dueren, Germany). Library sizes were determined by plating out serial dilutions of the pre-culture onto selective agar plates (titration plates) and obtained clone numbers were calculated to estimate library complexities. At least 12 clones from titration plates were analyzed by restriction digest and sequencing of variable regions using primer pPBseq13 (GGCCAGCTTGGCACTTGATG (SEQ ID NO:49)).

Expression, Display and Identification of Best Humanized ROR1 mAbs

For the Display of humanized antibody libraries L11 murine preB cells were used, which represent an in-house generated subclone of the Abelson murine leukemia virus (A-MuLV) transformed preB cell line 63-12 isolated from RAG-2 deficient mice (Shinkai Y et al. (1992) Cell, 68(5), 855-867). The cells were cultured in SF-IMDM media supplemented with 2% fetal calf serum, 2 mM L-Glutamine, 100 IU Penicillin, 0.1 mg/ml Streptomycin (Amimed, Bio-Concept Ltd., Allschwil, Switzerland) and 5 μM b-mercaptoethanol (Amresco, Solon, USA) in screwcap bottles (Sarstedt, Nümbrecht, Germany) at 37° under 7.5% $CO_2$.

EMT6 cells, a kind gift of Prof. A. Zippelius (University of Basel) and 293T cells were both grown in DMEM supplemented with 10% FCS, 2 mM L-Glutamine, 100 IU Penicillin, 0.1 mg/ml Streptomycin and 0.25 μg/ml Fungizone (Amimed) at 37° under 5% $CO_2$. 697 cells were grown in RPMI supplemented with 10% FCS, 2 mM L-Glutamine, 100 IU Penicillin, 0.1 mg/ml Streptomycin and 0.25 μg/ml Fungizone (Amimed) at 37° under 7.5% $CO_2$.

Transposition and Selection of L11 Cells Expressing Humanized Anti-ROR1 IgG Libraries:

One day before electroporation, L11 cells were seeded at a density of 0.2E+6 cells/ml to obtain log-phase growing cells the next day. The entire procedure of electroporation was performed at room temperature. Cells were harvested by centrifugation at 1200 rpm for 6 min and resuspended in plain RPMI medium to a concentration of 8E+7 cells/ml. Per cuvette, 25 μg of total DNA was diluted in 400 μl RPMI (using HC/LC/tranposase weight ratios as shown in FIG. S2B) and 400 μl cell suspension was combined with diluted DNA and transferred to a 0.4 cm gap gene pulser cuvette (BioRad, Hercules, USA). Electroporation was done with a BioRad GenePulser II equipped with capacitance extender set to 300V and 950 μF. After incubation for 5-10 min in cuvettes in order to allow pores to close, cells were washed once in complete SF-IMDM growth medium, resuspended and seeded into T175 tissue culture flasks at a total volume of 64 ml of complete growth medium. For selection, 1 μg/ml Puromycin and 800 μg/ml Hygromycin (0240.4 and CP12.2, respectively; Carl Roth, Karlsruhe, Germany) were added simultaneously, and selection was allowed to proceed for 4-5 days without exchange of medium or subculturing, until selection was complete.

FACS Staining and FACS Sorting of Cellular Libraries

Cells were stained on ice in FACS-buffer (PBS supplemented with 2% FCS) at a concentration of 1E+7 cells/ml. Wash steps were performed by pelleting cells by centrifugation at 1300 rpm for 3 min, resuspending in FACS-buffer using a 5× volume of staining reactions, pelleting again and resuspending in FACS buffer using 1× volume of staining reaction.

For analysis of surface-antibody expression, cells were stained using 1:200 diluted Ig-kappaLC-APC labeled antibody (MH10515, Life Technologies, Carlsbad, USA) for 30 minutes. Cells were washed once and analysed by flow cytometry on a FACSCalibur instrument (Becton-Dickinson, Franklin Lakes, USA).

For staining of cellular libraries expressing IgG libraries, previously determined limiting concentrations of antigen (0.25 μg/ml ROR1-strep) and 1:250 diluted anti-Human-IgG (Fc gamma-specific) PE (ebioscience 12-4998-82) were added and cells were incubated on ice in the dark for 30 minutes. After washing cells once, 1:500 diluted Strep-mAb classic Oyster 645 (2-1555-050 iba, Goettingen, Germany) was used to detect strep-tagged antigen bound to cells for 30 minutes. After a final wash, cells were filtered using cell strainer cap FACS tubes (BD Falcon). Sorting was performed on a FACSAriaII instrument (Becton-Dickinson, Franklin Lakes, USA).

Screening of Anti-ROR1 IgG Expressing L11 Clones by ELISA

Antigen-binding analysis by ELISA was performed by coating of Nunc-Immuno MaxiSorp 96-well plates (Thermo Scientific, Waltham, USA) with antigen diluted in coating buffer (100 mM bicarbonate/carbonate buffer) over night at 4° C. For sandwich ELISA, plates were coated with 2 μg/ml AffiniPure F(ab')2 fragment donkey anti-human IgG (Jackson Immunoresearch, West Grove, USA) diluted in coating buffer over night at 4° C. After coating, plates were washed twice with PBS/0.05% Tween-20 (PBS-T), blocked with PBS-T containing 3% bovine serum albumin (BSA) (Carl Roth, Karlsruhe, Germany) for 1 hour at 37° C. and washed again 5 times with PBS/T. L11 clone supernatants were pre-diluted 3-fold, while supernatants from 293T cells were pre-diluted 50-fold. Parental mAbs diluted to 0.5 µg/ml were used to generate standard curves. 3.5-fold serial dilutions of samples were added and plates were incubated for 1 hour at 37° C. After 5 washes with PBS/T, HRPO-conjugated F(ab)2 anti-human FC-gamma (Jackson Immunoresearch, West Grove, USA) was added at 10'000-fold dilution in PBS/T containing 1% BSA, and plates were incubated for 1 hour at 37° C. Finally, plates were washed 5 times with PBS/T and 50 µl of Sigmafast OPD Peroxidase substrate (Sigma-Aldrich, St. Louis, USA) were added. Reactions were stopped by adding 50 µl of 2M $H_2SO_4$. Absorption was measured at 490 nm. OD50 values of standards with known concentrations and samples determined by 4-point curve fitting models were used to calculate EC50.

Analysis of Affinity by Surface Plasmon Resonance (SPR)

Affinities were determined using a Biacorel® T200 instrument (GE Healthcare, Buckinghamshire, UK) and data was evaluated using Biacorel® Evaluation T200 V2.0 software. To capture mAbs, goat α-human Fc-gamma-specific IgG (Jackson ImmunoResearch, #109-005-098) was covalently immobilized on a CM5 chip (GE Healthcare, #BR-1005-30).

For measurement of L11 clone supernatants, antibodies were diluted to 0.3 µg/ml with complete SF-IMDM cell culture medium and captured for 120 s with a flow of 10 µl/min. ROR1-strep was diluted to 40 nM in running buffer. Association was measured at a flow rate of 30 µl/min for 120 s, and dissociation was followed for 200 s. Curves were fitted using 30 s dissociation due to upper plateau formation at later timepoints. Capture levels ranged from 29.1 RU to 57.7 RU.

For determination of anti-ROR1 affinities of selected 2A2- and R11-based humanized clones and comparison to parental mAbs, purified mAbs were diluted to 0.3 µg/ml with running buffer and captured for 120 s with a flow of 10 µl/min. ROR1-strep was diluted in running buffer using 2-fold serial dilutions ranging from 20 nM to 2.5 nM. Association was measured at a flow of 30 µl/min for 120 s, and dissociation was followed for 200 s. Curves were fitted using 30 s dissociation due to upper plateau formation at later timepoints. Capture levels ranged from 29.1 RU to 57.7 RU.

For initial determination of huR12 clone affinities and parental R12 using transient HEK293T supernatants, IgG expression vectors were transiently transfected into 293T cells and IgG titers in supernatants were quantified by ELISA. For SPR, supernatants were diluted to 1 µg/ml IgG with running buffer (HBS-EP+pH 7.4 (10 mM HEPES, 150 mM NaCl, 3 mM EDTA, 0.05% Tween® 20)) and captured for 200s with a flow of 30 µl/min. ROR1-strep was diluted in running buffer using 2-fold serial dilutions ranging from 20 nM to 2.5 nM. Association was measured at a flow of 30 µl/min for 120s, and dissociation was followed for 1000s. Capture levels ranged from 26.9 RU to 54.1 RU.

For determination of huR12 clone affinities and parental R12 using purified IgG, mAbs were diluted to 2 µg/ml IgG with running buffer (HBS-EP+pH 7.4 (10 mM HEPES, 150 mM NaCl, 3 mM EDTA, 0.05% Tweed® 20)) and captured for 200s with a flow of 30111/min. ROR1-strep was diluted in running buffer using 2-fold serial dilutions ranging from 1.25 nM to 20 nM. Association was measured at a flow of 30 µl/min for 120s, and dissociation was followed for 1000s. Capture levels ranged from 26.9 RU to 54.1 RU.

All measurements were performed at 25° C. All curves were fitted using a 1:1 binding model with RI=0. Regeneration was done for 90 s using 100 mM $H_3PO_4$ at a flow of 30 µl/min.

Recovery and Identification of VH and VL Sequences from L11 Clones Displaying Strong ROR1 Binding Specificity RNA was extracted from ~2E+6 cells grown in 24-well plates using Tri-Reagent (Sigma-Aldrich, St. Louis, USA) and reverse transcribed with ProtoScriptII Reverse transcriptase (Neb, Ipswich, USA) using random nonamers, according to manufacturer's instructions. Variable regions were amplified by PCR using Q5 DNA polymerase (Neb, Ipswich, USA) by means of forward primer EF1aNotI_F (CCATTTCAGGTGTCGTGAGC (SEQ ID NO:50)) and reverse primers CG-revseq-1 (GTTCGGG-GAAGTAGTCCTTG (SEQ ID NO:51)) for VH and Intron-rev-1 (GTGGATGTCAGTAAGACCAATAGGTGCC (SEQ ID NO:52)) for VL. PCR products were purified by column purification (Macherey&Nagel, Dueren, Germany) according to the manufacturers instructions, digested with restriction enzymes and purified by agarose-gel purification. Recovered variable regions were cloned into pCB14b, along with human Ig-gamma1 or Ig-kappa constant regions by 2- or 3-way cloning, respectively. Variable regions from several bacterial clones were sequenced by Sanger sequencing (performed at Microsynth AG, Balgach, Switzerland) using sequencing primer CMVseq2 (GCAGTGTAGTCT-GAGCAGTAC (SEQ ID NO:53)) and were aligned to library sequences using Geneious Software (Biomatters, New Zealand).

Expression of Recombinant IgG Antibodies in 293T Cells

Expression of recombinant antibodies was performed by transfecting pCB14b-based expression constructs into HEK-293T cells and harvesting of cell supernatants.

For transient antibody expression, cells were transfected in 6-well-plates using Lipofectamine LTX plus (LifeTechnologies, Carlsbad, USA). Per well, 2.5 µg of total DNA was transfected, and fresh growth medium was added the next day and conditioned for 4 days. Supernatants were sterile-filtered and stored at −20° C. until analysis.

For large-scale, semi-stable antibody expression, cells were transfected in 10 cm dishes using Lipofectamine LTX plus, enriched by selection with 2 µg/ml Puromycin (0240.4, Carl Roth, Karlsruhe, Germany), expanded to 14 cm dishes coated with poly-L lysine and maintained in DMEM/F12 serum-free medium (Gibco) containing 161 µg/ml N-Acetyl-L-Cysteine, 10 mg/ml L-Glutathione and 1 µg/ml Puromycin. Supernatants containing antibodies were harvested twice a week, sterile-filtered and stored at 4° C. until purification. Purification by FPLC was performed using an Äkta purifier instrument (GE Lifesciences). After passing supernatants over Amsphere protein A columns (JWT203CE, JSR Micro, Sunnyvale, USA), followed by washing with PBS, antibodies were eluted with 0.1M Glycine pH 2.5 and immediately neutralized with 1M Tris pH 8.0. Buffer exchange with PBS was performed using Amicon Ultra-4 Centrifugal Filters (Merck Millipore).

Figure 19:
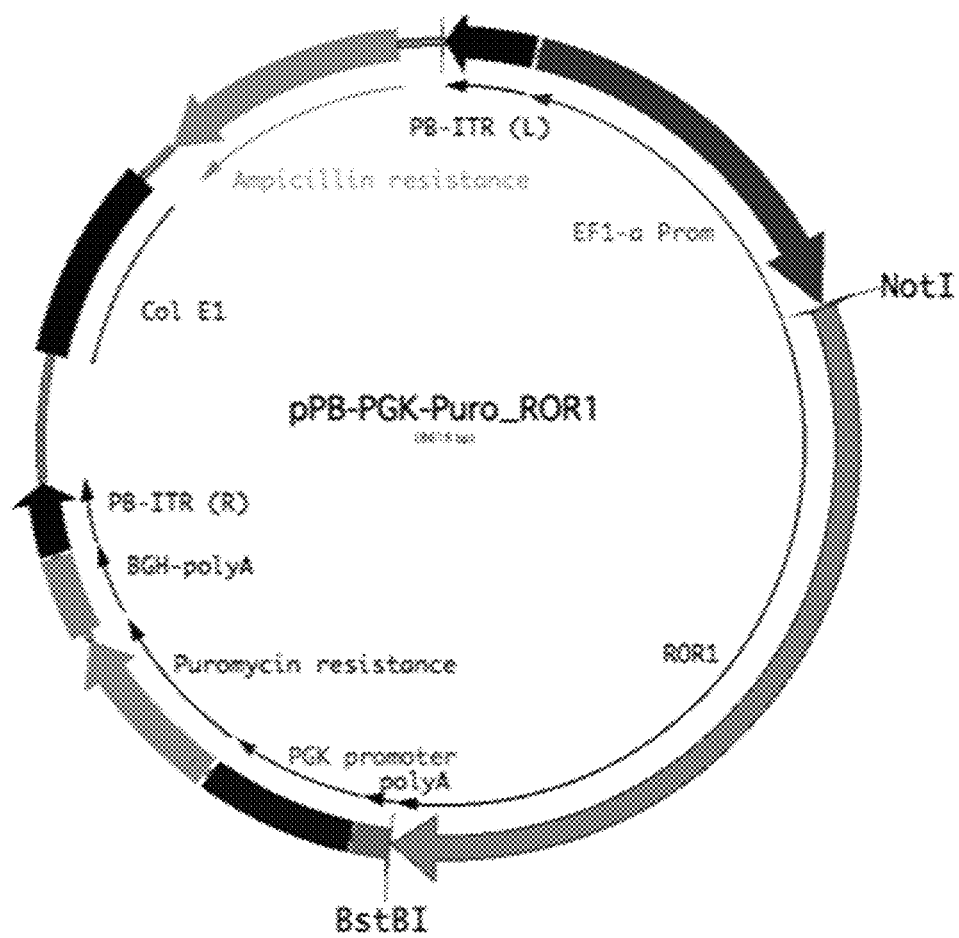

Generation of EMT-6 Cell Breast Cancer Cells Overexpressing Human ROR1 Target Antigen Murine EMT6 cells overexpressing human ROR1 antigen were generated by transposition. An expression construct for expression of full-length human ROR1 (NP_005003.2) was created using a PiggyBac-transposable expression vector containing a puromycin selection marker (pPB-PGK-Puro-ROR1) (FIG. 19). This vector was derived by replacing IRES-driven expression of antibiotic selection markers with selectable marker expression driven by a separate phosphoglycerate kinase promoter (PGK). Electroporation of EMT6 cells with the pPB-PGK-Puro-ROR1 expression vector and a PiggyBac expression vector pcDNA3.1-mPB (FIG. 17) was performed the same way as for L11 cells, except that EMT6 cell pellets were resuspended to 5E+6 cells/ml in RPMI, and 20 µg of total DNA was used (pPB-PGK-Puro-ROR1:transposase=3:2). After electroporation, cells were seeded on a 6-well plate and selection was performed using 3 µg/ml Puromycin for 6 days. Single cell clones were isolated by staining transposed and selected cells as follows: Cells were stained with 2 µg/ml anti-ROR1 antibody 2A2 (mouse-human IgG chimeric) diluted in FACS-buffer (PBS/ 2% FCS) for 30 min on ice. After washing with FACS-buffer, the primary antibody was detected using PE-coupled Fc-specific anti-human-IgG diluted 1:200 in FACS buffer for 30 min on ice. After a final wash, single cells were sorted into 96-well plates using a FACSAriaII instrument with FACSDiva software (Becton-Dickinson, Franklin Lakes, USA). After expansion, clones were verified to homogenously express antigen by staining as above and flow cytometry analysis.

Sortase-Mediated Antibody Conjugation

Sortase-mediated antibody conjugation was performed essentially as described (Beerli et al., PloS One, 10(7), e0131177, 2015). Briefly, sortase-tagged mAbs [10 µM] were incubated with oligo-glycine modified toxin [200 µM] in the presence of 3 µM Sortase A in 50 mM HEPES, 150 mM NaCl, 1 mM $CaCl_2$, 10% Glycerol, pH 7.5 for 3.5 h at 25° C. The reaction was stopped by passing it through an rProtein A GraviTrap column (GE Healthcare) equilibrated with 25 mM HEPES, 150 mM NaCl, pH 7.5, followed by washing with 20 column volumes (CVs) of wash buffer (25 mM HEPES pH 7.5, 150 mM NaCl, 10% v/v Glycerol). Bound conjugate was eluted with 5 CVs of elution buffer (0.1M Glycine, 50 mM NaCl, pH 2.5), with 0.5 CV fractions collected into tubes containing 25% v/v 1M HEPES pH 8 to neutralize the acid. Protein-containing fractions were pooled and formulated using ZebaSpin desalting columns (GE Healthcare, Thermo) according to the manufacturer's instructions. ADCs based on chimeric and humanized versions of mAbs 2A2 and R11 were formulated in PBS without $Ca^{2+}$ and $Mg^{2+}$ (Amimed-Bioconcept). ADCs based on chimeric mAb R12 were formulated in 20 mM HEPES, pH6.8, 175 mM Sucrose, 0.02% Tween20, while ADCs based on humanized R12 mAbs were formulated in 15 mM Histidine, pH 6.0, 175 mM Sucrose, 0.02% Tween20.

In Vitro Cell Killing Assays

Cytotoxicity of ADCs was investigated in cell killing assays essentially as described (Beerli et al., 2015). Briefly, cells were plated on 96 well plates in 75 µgrowth medium and grown at 37° C. in a humidified incubator in a 7.5% $CO_2$ atmosphere. Cells were seeded at 1'000 cells/well (EMT6 and derived clones thereof) or 10'000 cells/well (for testing 2A2 and hu2A2 ADCs on 697 cells) or 75'000 cells (for testing huR12-4 ADC on 697 cells) into 96-well plates. The following day, 25 µL of 3.5-fold serial dilutions of each ADC in growth medium was added, resulting in final ADC concentrations from 20 µg/mL to 0.02 ng/ml. For competition, ADC serial dilutions were done in growth medium containing unconjugated mAb ("comp") at a concentration of 200 µg/mL. After 4 additional days, plates were removed from the incubator and equilibrated at room temperature. After approximately 30 minutes, 50 µL medium was carefully removed from each well and replaced with 50 µL CellTiter-Glo® Luminescent Solution (Promega, Cat. No G7570). After shaking the plates at 450 rpm for 5 min followed by 10 min incubation in the dark without shaking, luminescence was measured on a Tecan Spark 10M with an integration time of 250 milliseconds per well.

Disseminated Xenograft Model of Human B Cell Leukemia Cells (697) in NOD-SCID Mice The efficacy of an antibody drug conjugate (ADC) based on hu2A2b-Q11, SMAC-conjugated with the glycine modified toxin of FIG. 6, was investigated and compared to a group treated with isotype control-ADC (trastuzumab, targeting HER2) in a disseminated xenograft model of female NOD-SCID mice carrying tumors derived from human 697 leukemia cancer cells. Twelve 9-week old mice, each weighing at least 20 g, were inoculated with 697 tumor cells ($5\times10^6$ cell/animal, in 200 µL PBS (Dulbecco's Phosphate Buffered Saline)) on study day 0. Test ADC, formulated in PBS, was administered (i.v.) in a group of 6 mice at 1.0 mg/kg on days 7, 14 and 21, with administration of mouse IgG (Privigen IVIG (CSL Behring, Lot. 4335500037), 30 mg/kg) 20 hours before each ADC administration. One isotype control ADC (HER2-targeting trastuzumab, SMAC-conjugated with the glycine modified toxin of FIG. 6), was administered under the same conditions and protocol in a group of 6 mice. Any animal showing clinical signs of moderate pain, moderate distress or any degree of suffering was humanely euthanized. Furthermore; any animal was humanely euthanized if it exhibited clinical signs that exceed the limits of the study specific humane endpoints according to the European and Danish legislation on animals in experimental studies. Body weight of each animal was measured three times weekly throughout the study. Data analysis was performed using the software PRISM.

FIGURES

FIG. 1: Chemical structures of the $Gly_5$ modified maytansine toxins used for SMAC-Technology™ immunoligand conjugation.

In the upper part of FIG. 1 displays the maytansinoid is DM1 ([$N^{2'}$-deacetyl-$N^{2'}$-(3-mercapto-1-oxopropyl)-maytansine], containing the so-called SMCC linker to which the oligo-glycine peptide ($Gly_n$), in order to allow conjugation by SMAC-Technology™, This SMCC linker is only an optional component for the SMAC-Technology™ conjugated immunoligand toxin conjugates, and of no importance for the conjugation of the payload.

Instead of DM1, other optional linker structures, like the SPDB linker of the maytansinoid payload DM4 ([N20-deacetyl-N20-(4-mercapto-4-methyl-1-oxo-pentyl)-maytansine] may optionally be included, see FIG. 2.

In the lower part of FIG. 1, the maytansinoid is maytansine itself, which in the unconjugated form has the structure of FIG. 2 (*a*), may be used to generate the oligo-glycine peptide ($Gly_n$) derivative depicted here, which has formed the basis for the immunoligand maytansine conjugates analyzed herein.

FIGS. 2(*a*)-2(*c*): Three Maytansinoids that can be used in the context of the present invention. FIG. 2(*a*): Maytansine, FIG. 2(*b*): DM1 ([$N^{2'}$-deacetyl-$N^{2'}$-(3-mercapto-1-oxopropyl)-maytansine], FIG. 2(*c*): DM4 ([N20-deacetyl-N20-(4-mercapto-4-methyl-1-oxo-pentyl)-maytansine].

Figure 5:
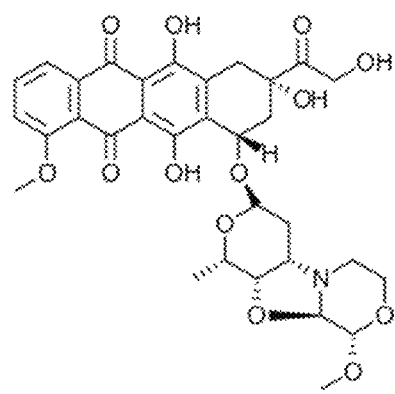

FIG. 3 (*a*): An anthracycline (PNU) derivative that can be used with the Immunoligand-Toxin-conjugate according to the invention. The derivative may comprise at its wavy line a chemical structure comprising an oligo-glycine peptide ($Gly_n$) (SEQ ID NO: 72) coupled to said anthracyline derivative in such a way that the oligo-glycine ($Gly_n$) (SEQ ID NO: 72) peptide has a free amino terminus, and wherein n is an integer between >1 and <21. The derivative is derived from anthracycline PNU-159682 having the formula (v) as depicted in FIG. 5.

FIG. 3 (*b*): An oligo-glycine peptide ($Gly_n$) (SEQ ID NO: 72) is coupled to the anthracyline derivative as seen in FIG.

3 (a) by means of an ethylenediamino linker (EDA), which ethylenediamino linker is coupled to the anthracycline derivative by means of a first amide bond, while it is conjugated to the carboxyterminus of the oligo-glycine peptide by means of a second amide bond, said ethylenediamino linker and oligo-glycine peptide.

Figure 4:
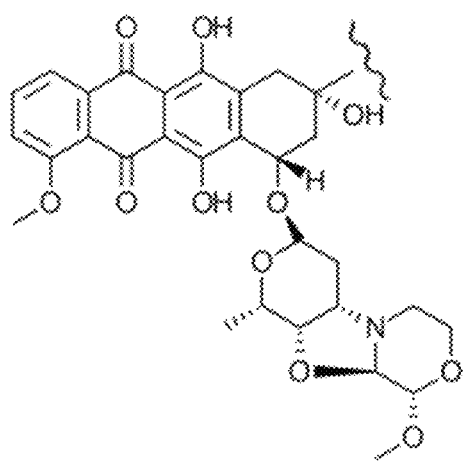
Figure 4:
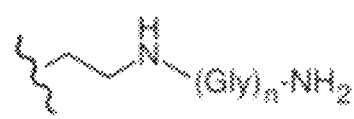

FIG. 4 (a): Another anthracycline (PNU) derivative that can be used with the Immunoligand-Toxin-conjugate according to the invention. The derivative may comprise at its wavy line a chemical structure comprising an oligo-glycine peptide $(Gly_n)$ (SEQ ID NO: 72) coupled to said anthracyline derivative in such a way that the oligo-glycine $(Gly_n)$ (SEQ ID NO: 72) peptide has a free amino terminus, and wherein n is an integer between >1 and <21. The derivative is derived from anthracycline PNU-159682 having the formula (v) as depicted in FIG. 5.

FIG. 4 (b): An oligo-glycine peptide $(Gly_n)$ (SEQ ID NO: 72) is coupled to the anthracyline derivative as seen in FIG. 4 (a) by means of an ethylenediamino linker (EDA), which ethylenediamino linker is coupled to the anthracycline derivative by means of a first amide bond, while it is conjugated to the carboxyterminus of the oligo-glycine peptide by means of a second amide bond, said ethylenediamino linker and oligo-glycine peptide.

FIG. 5: Structure of PNU-159682 as described in the prior art (e.g. WO2009099741, or Quintieri L et al (2005) Clin Cancer Res. 11, 1608-17.

FIG. 6: Structure of PNU-EDA-Gly$_5$ as utilized for the SMAC-technology conjugation to C-terminally LPETG (SEQ ID NO: 73) sortase tagged monoclonal antibodies using sortase enzyme as disclosed in the examples herein.

Figure 7:
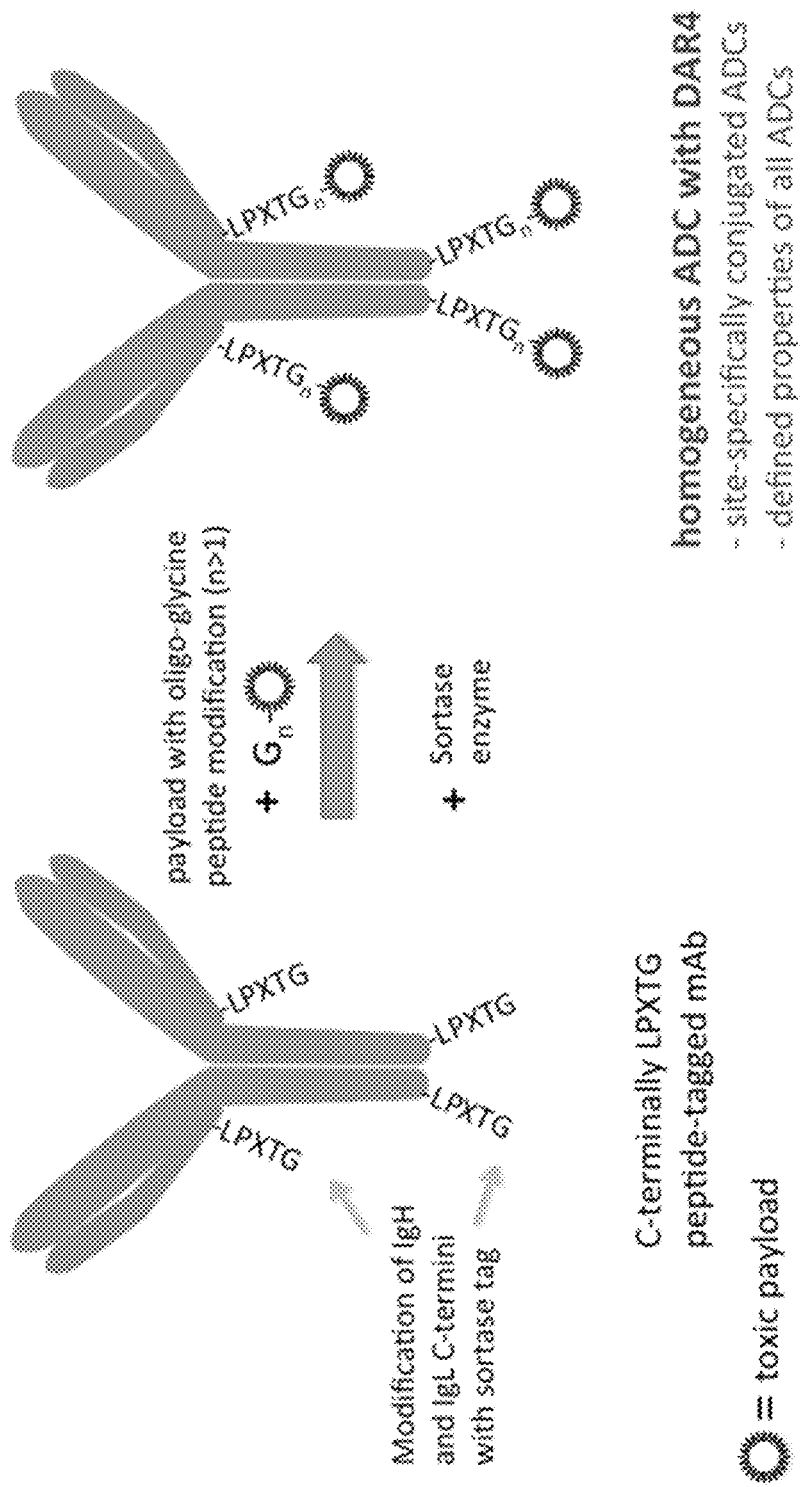

FIG. 7: Schematic drawing of site-specific sortase mediated antibody conjugation (SMAC-technology). The monoclonal antibodies need to be produced with C-terminal LPXTG (SEQ ID NO: 58) sortase tags. The toxic payload needs to be produced to contain an oligoglycine peptide stretch (Glyn-stretch) with a certain number of glycine (n>1 and <21, preferably n>3 and <10, most preferably n=5) residues in a row. Sortase A enzyme from Staph, aureus specifically recognizes the LPXTG (SEQ ID NO: 58) pentapeptide motif and catalyzes the transpeptidation of the oligo-glycine peptide stretch to the threonine-glycine peptide bond of LPXTG (SEQ ID NO: 58), thereby generating a new stabile peptide bond between the threonine and the N-terminal glycine of the oligo-glycine stretch.

Figure 8A:
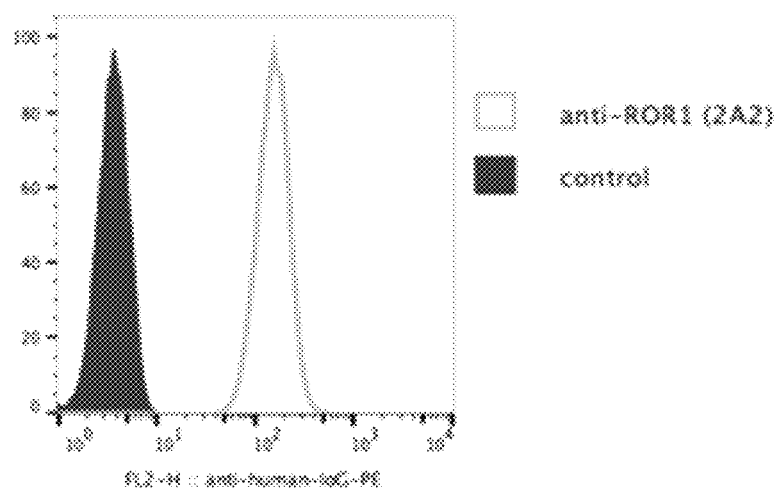
Figure 8B:
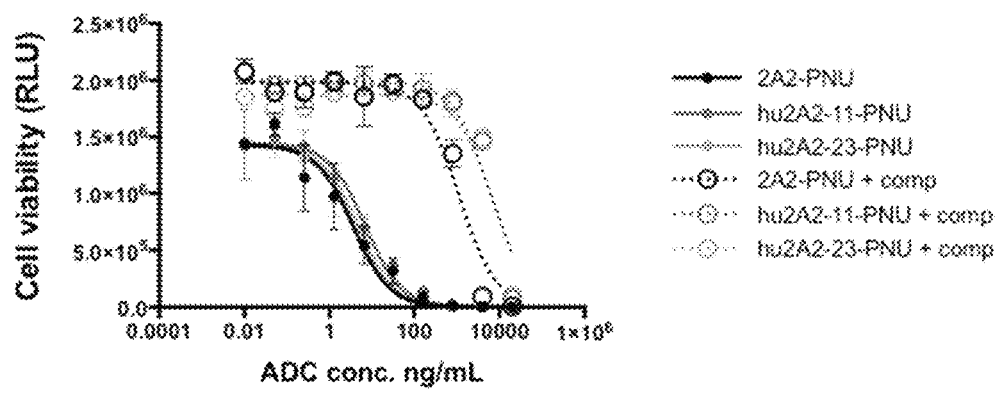
Figure 8C:
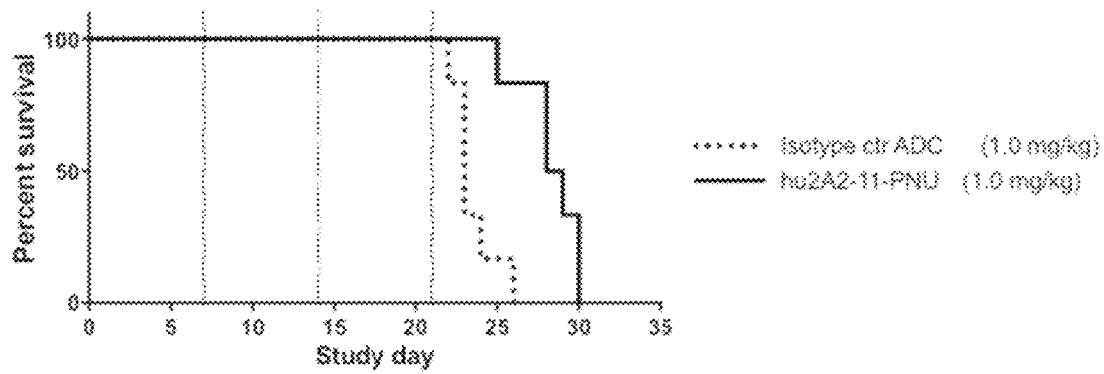

FIGS. 8A-8C: To evaluate performance of humanized 2A2 antibodies and to compare with potency of the parental, chimeric mAb in the form of antibody-drug conjugates (ADCs). To generate ADCs antibodies were expressed heavy and light chains C-terminally tagged with sequences comprising a sortase A recognition motif, and were coupled to the Gly5-modified anthracyclin PNU159682-derivative using Sortase-mediated conjugation (WO2014140317) and were then tested in in vitro killing assays using ROR1-expressing ALL cancer cell lines. 697 ALL expressed ROR1 as revealed by staining with 2A2 anti-ROR1 antibody and analysis by flow cytometry (FIG. 8A). When cell killing was performed, both chimeric 2A2-PNU and humanized versions efficiently killed 697 cells, and this effect was target-specific because it could be competed with unconjugated antibody ("cold competition"). After four days of treatment, viable cells were quantified using a luminescent cell viability assay. Each data point represents the mean of duplicates and error bars represent SD (FIG. 8B). Efficacy of humanized 2A2 ADC was evaluated in vivo in a disseminated mouse model established with human 697 ALL cell line. Kaplan-Meyer survival curves are shown and compared with a group treated with an isotype control (FIG. 8C). Mice treated with the humanized 2A2 ADC display a prolonged survival relative to the control.

FIGS. 9A-9C: Humanization of mouse 2A2 and rabbit R11 anti-ROR1 antibodies by Transpo-mAb. Transposable humanized libraries consisted of 64 VH×49 VL (mouse) and 101 VH×82 VL (rabbit) sequences and were transposed using a DNA weight ratio of 4:2:1 (HC:LC:transposase). The cellular library was enriched for antibody expression by antibiotic selection and labelled for antigen binding using soluble antigen (ROR1-strep) at previously determined limiting concentrations. Antigen binding was detected using a fluorophore labeled anti-strep-tag antibody (StrepMAB-645). To normalize for antibody surface expression levels, libraries were co-stained with anti-IgG-PE. Antigen-binding single-cells were then isolated by FACS. FIG. 9A shows flow cytometry plots of humanized cellular libraries analyzed for antigen-binding (x-axis) and antibody surface expression (y-axis) as analyzed immediately prior to sorting. After single-cell sorting, clone supernatants were expanded, thereby generating antibody-containing conditioned supernatants which were screened by SPR. FIG. 9B shows an isoaffinity plot displaying $k_a$ and $k_d$ determined by SPR with single-cell sorted clone supernatants (unicates) or purified parental mAbs (triplicates). Antibody sequences of 5 clones showing best KDs were recovered by RT-PCR and deconvoluted/validated by ELISA. Sequences not matching library design were not pursued further. The top 3 clones from this analysis were expressed in 293T cells, purified and affinities were measured by SPR. FIG. 9C shows an isoaffinity plot of these purified top 3 mAbs of each screen.

FIG. 10: Humanization of rabbit R12 antibody by Transpo-mAb. Transposable humanized libraries consisted of 25 VH×25 VL sequences and were transposed into L11 cells using a DNA weight ratio of 0.25:0.125:1 (HC:LC:transposase). Cells transposed with the humanized R12 cDNA library were enriched for antibody surface expression by antibiotic selection and then single-cell sorted for antigen binding. The resulting clones were expanded and culture supernatants were analysed by ELISA. Shown is a scatter-plot of single-cell clone supernatants analyzed in parallel for antigen binding and IgG titer by ELISA. Serial dilutions of clonal supernatants grown in 96-well plates were directly used for assessing binding to ELISA plates that were coated with limiting concentrations of ROR1 to minimize avidity effects. IgG levels were determined by sandwich ELISA. EC50 values were calculated using standard curves obtained with known concentrations of parental mAb R12. Those sixteen clones with highest ROR1-binding:IgG-titer ratios were chosen for antibody variable region sequence recovery.

FIG. 11: Comparison of generated humanized antibodies alongside clinically approved humanized mAbs with human germline genes. Variable regions of indicated antibodies were subjected to Ig-Blast database search (ncbi.nlm.nih-.gov/igblast/) for the closest human germline sequence each, and sequence identity within framework regions 1, 2 and 3 were determined. Average identity with human germline over all three frameworks was considered as a measure of humanization grade and is shown in percent. For libraries, mean values over all sequences within the library are shown. FDA approval status and sequences of reference humanized antibodies and were retrieved from imgt.org/.

Figure 12A:
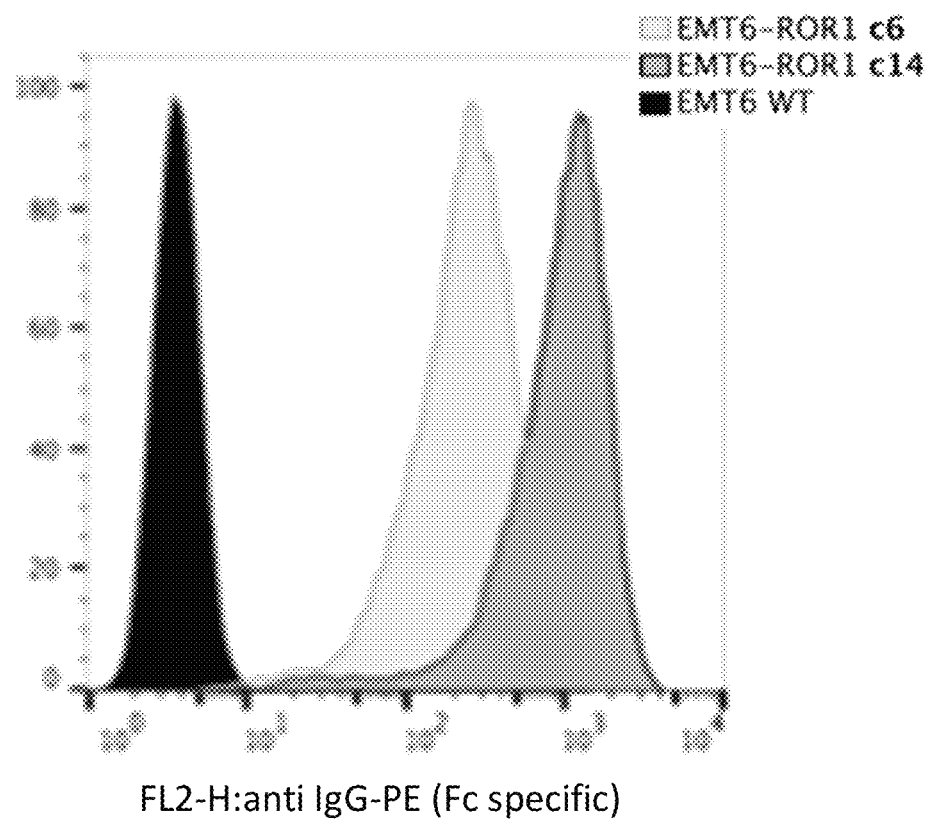
Figure 12B:
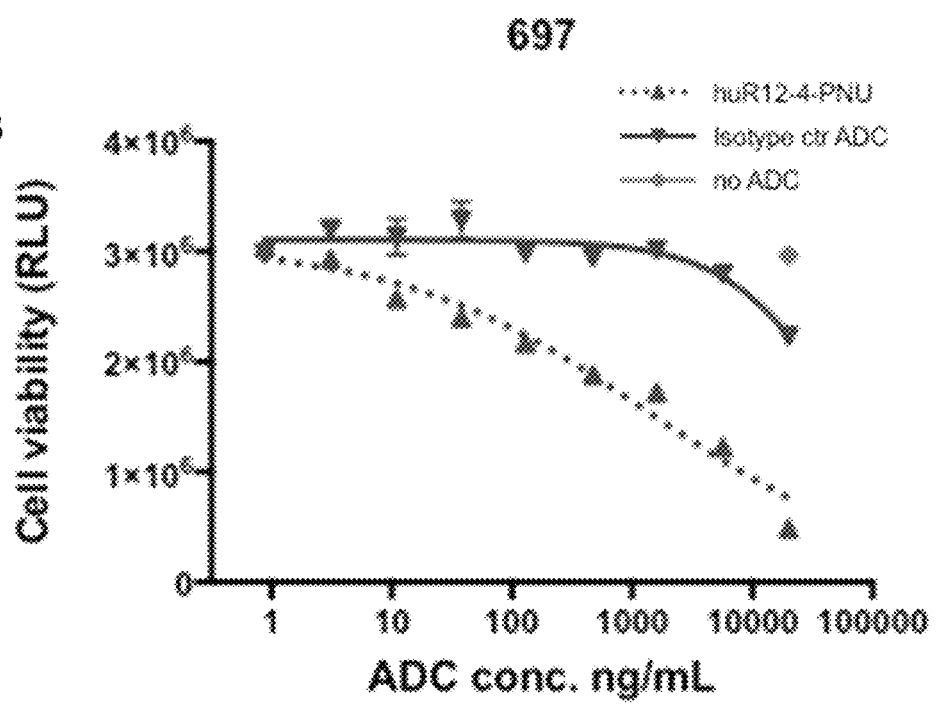
Figure 12C:
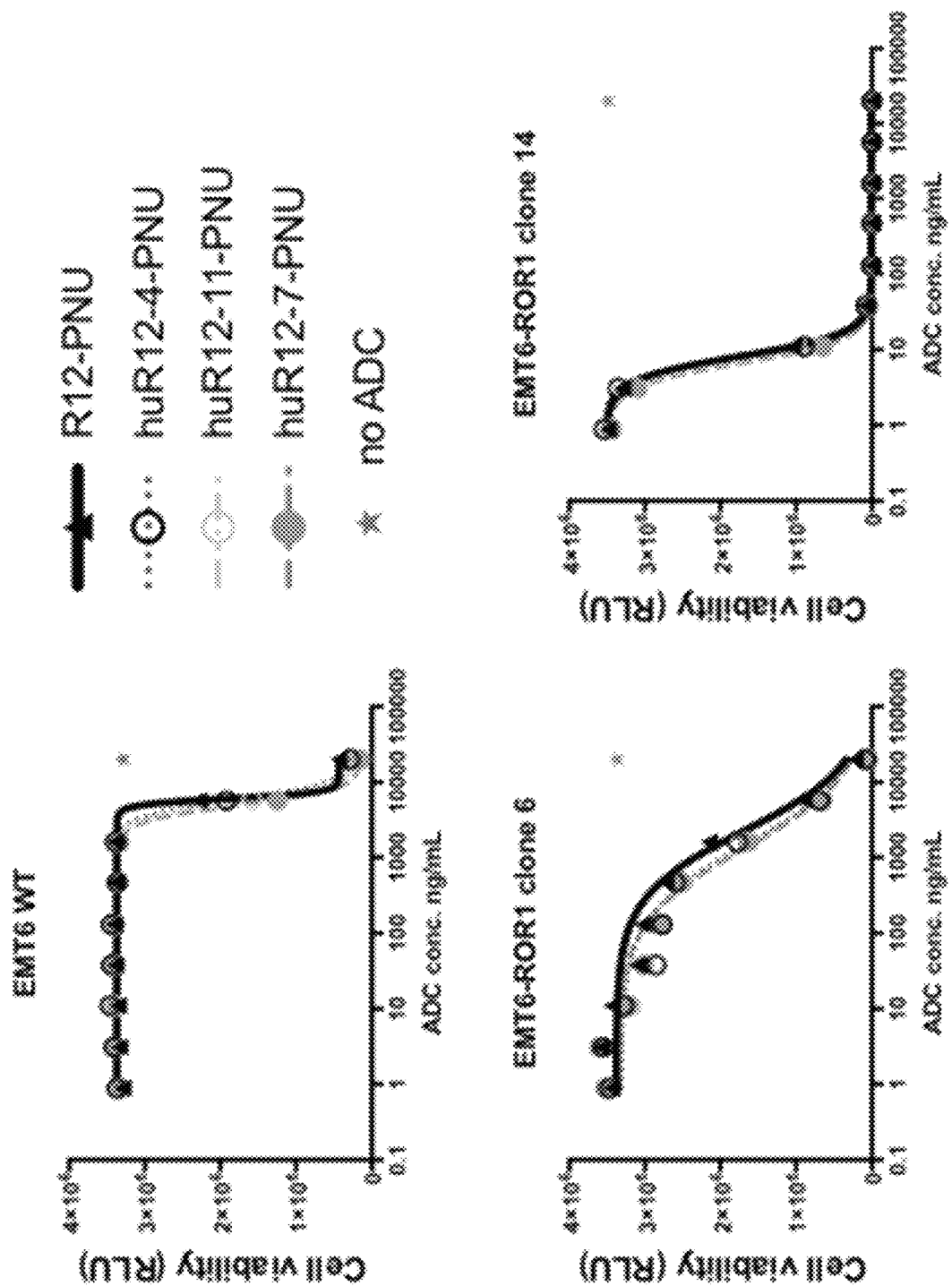

FIGS. 12A-12C: Performance of humanized R12 antibodies and comparison with potency of the parental, chimeric mAb in the form of antibody-drug conjugates (ADCs). To generate ADCs, antibodies were expressed with heavy- and light-chains comprising a c-terminal sortase A recognition motif, and were coupled to a Gly5-modified anthracycline (as per FIG. 6) using Sortase-mediated conjugation (WO2014140317). The resulting ADCs were tested in in vitro killing assays using human 697 ALL cells expressing endogenous levels of ROR1 (FIG. 8A), and using clones of murine EMT6 cells overexpressing human ROR1 (EMT6-ROR1 clone 6, EMT6-ROR1 clone 14), or parental EMT6 cells (EMT WT). To verify the absence or presence of antigen surface expression on EMT6 cell variants, cells were stained with 2 µg/ml 2A2 anti-ROR1 antibody and were subsequently analysed by flow cytometry (FIG. 12A). To assess the potency of the ADCs generated, human ALL cancer cells (697), as well as murine EMT6 cells overexpressing human ROR1 (EMT6-ROR1 clone 6, EMT6-ROR1 clone 14), or parental EMT6 cells (EMT WT) were exposed to ADCs for 4 days and cell viability was quantified using a luminescence-based cell viability assay (FIG. 12B and FIG. 12C, respectively). In all cases, cell viability of ROR1-expressing cells was reduced (in positive correlation with ROR1 expression) when treated with humanized R12-based ADCs, whereas treatment with control ADCs solely resulted in non-specific killing at highest doses.

FIG. 13: Comparison of affinities of humanized and parental R12 mAbs determined by SPR using purified antibody. The three humanized R12 mAbs indicated were expressed at large scale in HEK293T cells, purified by Protein A affinity chromatography and subjected to SPR analysis for determination of affinity towards soluble ROR1-strep. Antibodies were captured using a goat α-human Fc-gamma-specific IgG. ROR1-strep was diluted in running buffer using 2-fold serial dilutions ranging from 1.25 nM to 20 nM. Association was measured 120 s, and dissociation was followed for 1000 s. Capture levels ranged from 26.9 RU to 54.1 RU. This analysis confirms a substantial gain in affinity of humanized versus parental mAb R12 of more than 5-fold.

Figure 14:
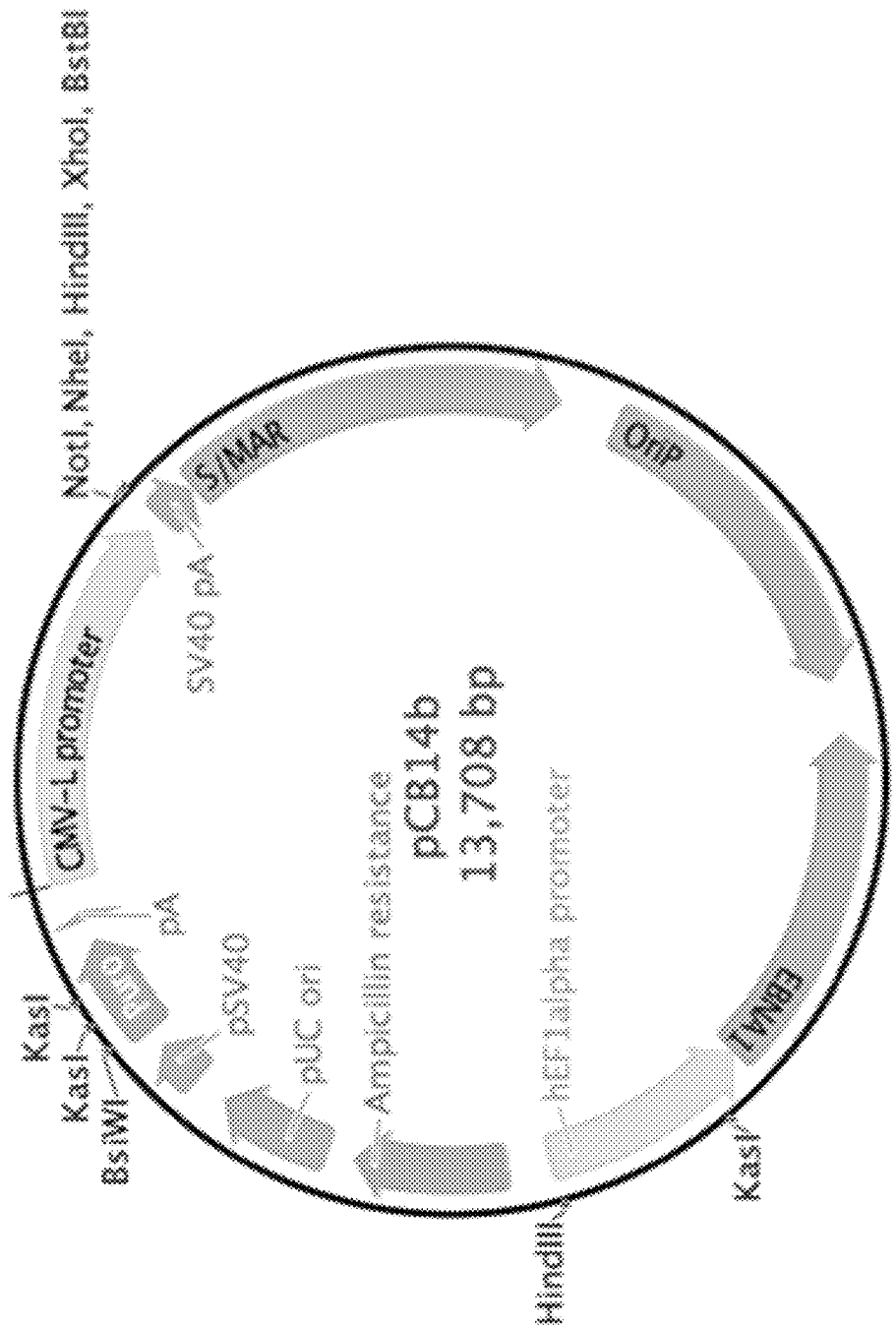
Figure 15:
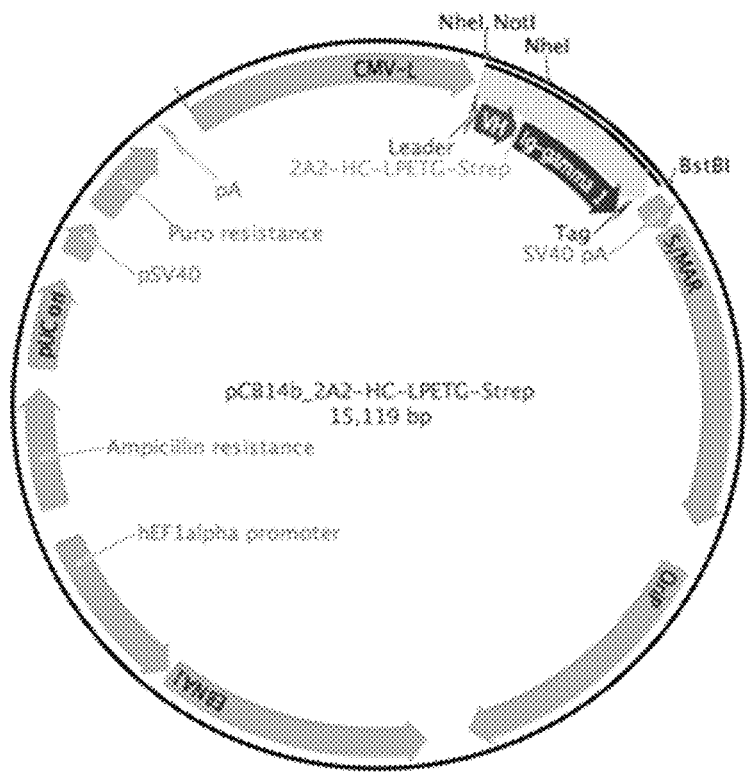
Figure 15:
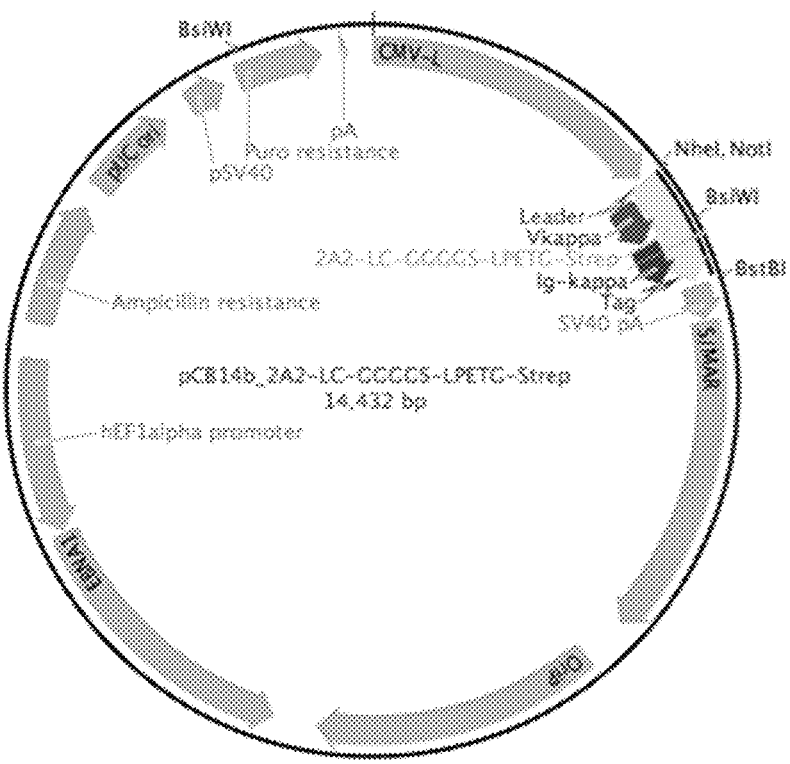
Figure 15:
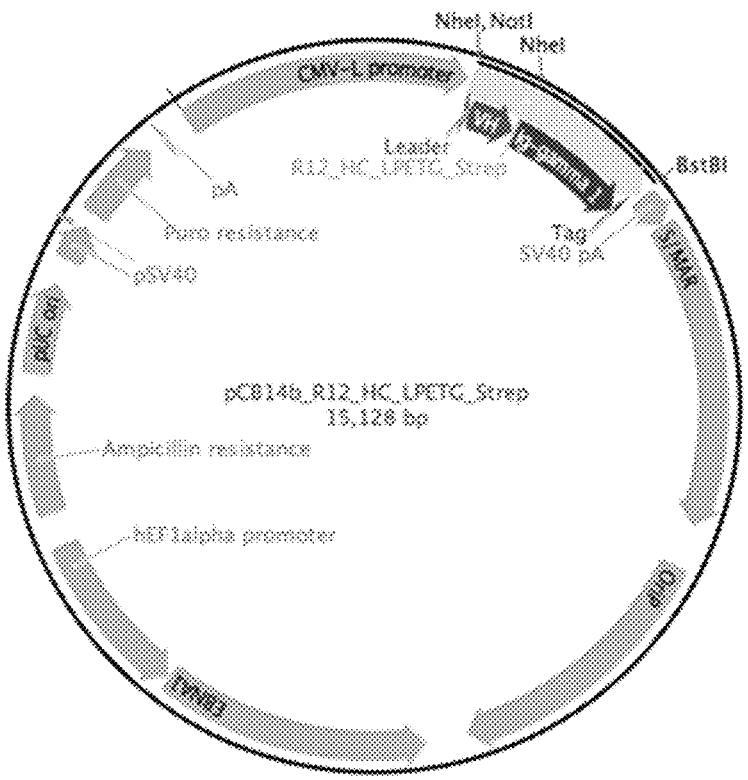
Figure 15:
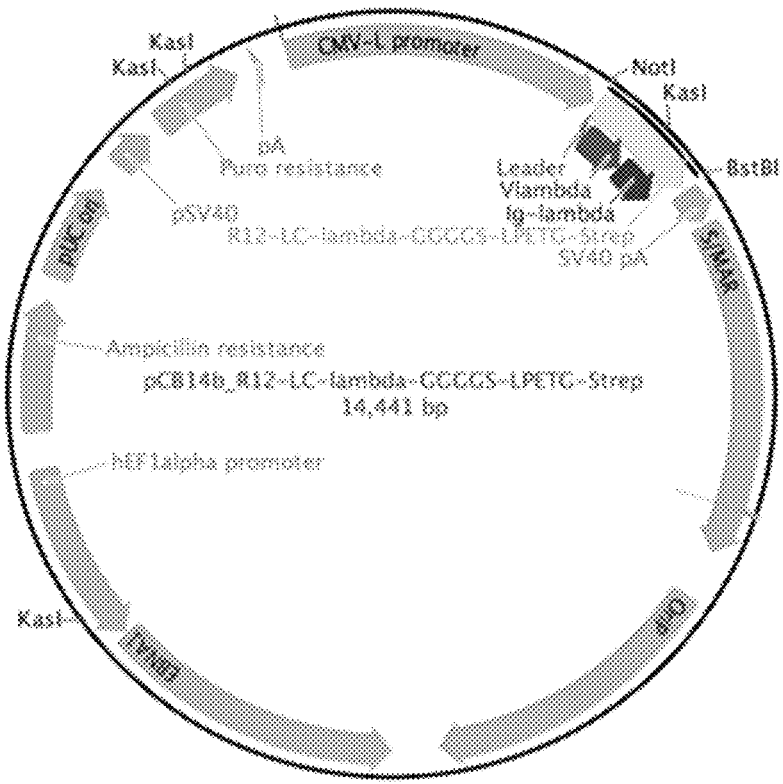

FIG. 14: EBNA-based expression vector pCB14b for transient or semi-stable antibody expression in HEK293T cells. Shown are the principal components of the vector and the restriction sites used for the described clonings.

FIGS. 15(a)-15(d): Transposable antibody expression constructs. Shown are the principal components of the vector and the restriction sites used for the described clonings. FIG. 15(a) Transposable 2A2 heavy chain expression vector. FIG. 15(b) Transposable 2A2 light chain expression vector. FIG. 15(c) Transposable R12 heavy chain expression vector. FIG. 15(d) Transposable R12 light chain expression vector.

FIG. 16: Sequence of Strep-tagged human ROR1. Shown is the amino acid sequence of the extracellular domain of human ROR1, N-terminally tagged with a strep-tag (WSHPQFEK (SEQ ID NO: 74)).

FIG. 17: Construct for transient expression of hyperactive PiggyBac transposase (hyPB).

FIGS. 18(a)-18(b): Vectors used as backbones to generate transposable heavy chain libraries. Shown are the principal components of the vector and the restriction sites used for the described clonings. FIG. 18(a) Vector used for insertion of humanized heavy chain variable region fragments. Heavy chain variable region fragments were introduced using NotI/NheI sites. FIG. 18(b) Vector used for insertion of humanized light chain variable region fragments along with constant region fragments of kappa or lambda type. Kappa light chain variable region fragments digested with NotI/BsiWI were introduced into this vector linearized with NotI/BstBI, along with kappa light chain constant region fragments digested with BsiWI/BstBI. Lambda light chain variable region fragments digested with NotI/KasI were introduced into this vector linearized with NotI/BstBI, along with lambda light chain constant region fragments digested with KasI/BstBI.

FIG. 19: Transposable vector for expression of full-length ROR1. Shown are the principal components of the vector and the restriction sites used for the described clonings.

Sequences

| SEQ ID NO | Sequence Type | antibody type | Sequence |
|---|---|---|---|
| 1 | CDR1 HC | 2A2 | GYTFSDYE |
| 2 | CDR2 HC | 2A2 | IDPETGGT |
| 3 | CDR3 HC | 2A2 | TGYYDYDSFTY |
| 4 | CDR1 LC | 2A2 | QNVDAA |
| 5 | CDR2 LC | 2A2 | SAS |
| 6 | CDR3 LC | 2A2 | QQYDIYPYT |
| 7 | VR HC | chimeric mAb 2A2 | QVQLQQSGAELVRPGASVTLSOKASGYTFSDYEMHWVIQTPVHGLEWIGAIDPETGGTAYNQKFKGK AILTADKSSSTAYMELRSLTSEDSAVYYCTGYYDYDSFTYWGQGTLVTVSA |
| 8 | VR LC | chimeric mAb 2A2 | DIVMTQSQKIMSTTVGDRVSITCKASQNVDAAVAWYQQKPGQSPKLLIYSASNRYTGVPDRFTGSGS GTDFTLTISNMQSEDLADYFCQQYDIYPYTFGGGTKLEIK |
| 9 | VD HC | hu2A2b-Q11, humanized from 2A2 | EVQLVQSGAEVKKPGASVKVSOKASGYTFSDYEMHWVRQAPGQGLEWLGAIDPETGGTAYNQKFKGR VTMTGDTSISTAYMELSRLTSDDTAVYYQTGYYDYDSFTYWGQGTLVSVSS |
| 10 | VD LC | hu2A2b-Q11, humanized from 2A2 | DIQMTQSPSSLSTSVGDRVTITCKASQNVDAAVAWYQQKPGKAPKLLIYSASNRYTGVASRFSGSGS GTDFTFTISSLQSEDLADYFCQQYDIYPYTFGQGTKLEIK |

| SEQ ID NO | Sequence Type | antibody type | Sequence |
|---|---|---|---|
| 11 | VD HC | hu2A2-D23, humanized from 2A2 | QVQLVESGAEVKKPGASVKLSQKASGYTFSDYEMHWVRQAPGQRLEWMGAIDPETGGTAYNQKFKGR VTITVDKSASTAYMELSSLRSEDTAVYYQTGYYDYDSFTYWGPGTTVTVSS |
| 12 | VD LC | hu2A2-D23, humanized from 2A2 | DIVMTQSPSTLSASVGDRVTITCKASQNVDAAVAWYQQKPGTAPKLLIYSASNRYTGVPSRFSGSGS GTEFTLTISSLQSEDLADYFCQQYDIYPYTFGQGTKLEIK |
| 13 | VD HC | hu2A2-D16, humanized from 2A2 | EVQLVESGAEVKKPGASVKVSQKASGYTFSDYEMHWVRQAPGQGLEWVGAIDPETGGTAYNQKFKGR VTMTRDTSTSTVYMELSSLRSEDTAVYYQTGYYDYDSFTYWGQGTLVTVSS |
| 14 | VD LC | hu2A2-D16, humanized from 2A2 | DIQMTQSPSSLSASVGDRVTITCKASQNVDAAVAWYQQKPGKAPKLLIYSASNRYTGIPTRFSGSGS GTDFTLTISSLQSEDLADYFCQQYDIYPYTFGQGTKVEIK |
| 15 | CDR1 HC | R11 | GSDINDYP |
| 16 | CDR2 HC | R11 | INSGGST |
| 17 | CDR3 HC | R11 | GYSTYYGDFNI |
| 18 | CDR1 LC | R11 | QSIDSN |
| 19 | CDR2 LC | R11 | RAS |
| 20 | CDR3 LC | R11 | LGGVGNVSYRTS |
| 21 | VD HC | chimeric mAb R11 | QSVKESEGDLVTPAGNLTLTCTASGSDINDYPISWVRQAPGKGLEWIGFINSGGSTWYASWVKGRFT ISRTSTTVDLKMTSLTTDDTATYFCARGYSTYYGDFNIWGPGTLVTISS |
| 22 | VD LC | chimeric mAb R11 | ELVMTQTPSSTSAVGGTVTINCQASQSIDSNLAWFQQKPGQPPTLLIYRASNLASGVPSRFSGSRS GTEYTLTISGVQREDAATYYCLGGVGNVSYRTSFGGGTEVVVK |
| 23 | VR HC | rbQ11, humanized from R11 | MNFGLRLIFLVLTLKGVQCEVQLVQSGGGLVQPGGSLRLSCAASGSDINDYPISWVRQAPGKGLEWV SFINSGGSTWYASWVKGRFTISRDNAKNSLYLQMNSLRDDDTATYFCARGYSTYYGDFNIWGQGTLVTVSS |
| 24 | VR LC | rbQ11, humanized from R11 | MNFGLRLIFLVLTLKGVQCDIVMTQSPSSLSASVGDRVTITCQASQSIDSNLAWFQQKPGKAPKSLI YRASNLASGVPSKFSGSGSGTDFTLTISSLQREDAATLYCLGGVGNVSYRTSFGGGTKVEIK |
| 25 | VR HC | rbD4, humanized from R11 | EVQLVESGGGLVQPGRSLRLSCTASGSDINDYPISWFRQAPGKGLEWVGFINSGGSTWYASWVKGRF TISRDDSKSIALLQMNSLKTDDTATYFCARGYSTYYGDFNIWGQGTTVTVSS |
| 26 | VR LC | rbD4, humanized from R11 | DVVMTQSPSSLSASVGDRVTITCQASQSIDSNLAWFQQKPGKAPNLLIYRASNLASGVPSRFSGSGS GTEFTLTISSLQREDAATYYCLGGVGNVSYRTSFGQGTKVEIK |
| 27 | VR HC | rbQ12, humanized from R11 | EVQLVESGGGLVQPGGSLRLSCAASGSDINDYPISWVRQAPGKGLEWVSFINSGGSTWYASWVKGRF TISRDNAKNSLYLQMNSLRADDTATYFCARGYSTYYGDFNIWGQGTMVTVSS |
| 28 | VR LC | rbQ12, humanized from R11 | EIVMTQSPSSLSASVGDRVTITCQASQSIDSNLAWFQQKPGKAPNLLIYRASNLASGVPSRFSGSGS GTEFTLTISSLQREDAATYYCLGGVGNVSYRTSFGQGTKVEIK |
| 29 | CDR1 HC | R12 | GFDFSAYY |
| 30 | CDR2 HC | R12 | IYPSSGKT |
| 31 | CDR3 HC | R12 | ARDSLADDGAIFNI |
| 32 | CDR1 LC | R12 | SAHKTDT |
| 33 | CDR2 LC | R12 | VQSDGSY |
| 34 | CDR3 LC | R12 | GADYIGGYV |
| 35 | VR HC | Chimeric mAb R12 | QEQLVESGGRLVTPGGSLTLSCKASGFDFSAYYMSWVRQAPGKGLEWIATILPSSGKTYLATWVNG RFTISSDNAQNTVDLQMNSLTAADRATYFCARDSLADDGAIFNIWGPGTLVTISS |

Sequences

| SEQ ID NO | Sequence Type | antibody type | Sequence |
|---|---|---|---|
| 36 | VR LC | Chimeric mAb R12 | ELVLTQSPSVSAALGSPAKITCTLSSAHKTDTIDWYQQLQGEAPRYLMQVQSDGSYTKRPGVPDRF SGSSSGADRYLIIPSVQADDEADYYCGADYIGGYVFGGGTQLTVT |
| 37 | VR HC | huR12_4, humanized from R12 | QVQLVESGGELVQPGGSLTLSCKASGFDFSAYYMSWVRQAPGKGLEWIATILPSSGKTYLAASVQG RFTISADNAKNTVYLQMNSLTAADTATYFCARDSLADDGAIFNIWGKGTLVTVSS |
| 38 | VR LC | huR12_4, humanized from R12 | QLVLTQSPSVSAALGSSAKITCTLSSAHKTDTIDWYQQLAGQAPRYLMYVQSDGSYEKRSGVPDRF SGSASGADRYLAISRVQADDEADYYCGADYIGGYVFGGGTQLTVLG |
| 39 | VR HC | huR12_7, humanized from R12 | QVQLVESGGELVQPGGSLTLSCKASGFDFSAYYMSWVRQAPGKGLEWIATILPSSGKTYLAASVQG RFTISADNAKNTVSLQMNSLTAADTATYFCARDSLADDGAIFNIWGKGTLVTVSS |
| 40 | VR LC | huR12_7, humanized from R12 | QLVLTQSPSVSAALGSSAKITCTLSSAHKTDTIDWYQQLAGQAPRYLMYVQSDGSYEKRSGVPDRF SGSSSGADRYLIISSVQADDEADYYCGADYIGGYVFGGGTQLTVLG |
| 41 | VR HC | huR12_11, humanized from R12 | QVQLVESGGAIVQPGGSLTLSQKASGFDFSAYYMSWVRQAPGKGLEWIATIYPSSGKTYLAASVQG RFTISADNAKNTVYLQMNSLTAADTATYFCARDSLADDGAIFNIWGQGTLVTVSS |
| 42 | VR LC | huR12_11, humanized from R12 | QLVLTQSPSVSAALGSSAKITCTLSSAHKTDTIDWYQQLAGQAPRYLMYVQSDGSYEKRSGVPDRF SGSSSGADRYLIISSVQADDEADYYCGADYIGGYVFGGGTQLTVG- |
| 43 | VR HC | huR12_16, humanized from R12 | QVQLVESGGELVTPGGSLTLSCKASGFDFSAYYMSWVRQAPGKGLEWIASILPSSGKTYLAAAVQG RFTISADNAKNTVYLQMNSLTAADTATYFCARDSLADDGAIFNIWGQGTLVTVSS |
| 44 | VR LC | huR12_16, humanized from R12 | QLVLTQSPSVSAALGSSAKITCTLSSAHKTDTIDWYQQLAGQAPRYLMYVQSDGSYEKRSGVPDRF SGSSSGADRYLIISSVQADDEADYYCGADYIGGYVFGGGTQLTVG- |

INCORPORATION BY REFERENCE

This specification comprises several references to the sortase mediated antibody conjugation (SMAC). This technology is fully disclosed in WO2014140317, content of which is incorporated by reference herein for enabling purposes.

TABLE 1

| Ligand | Ligand Level (RU) | ka ($M^{-1}s^{-1}$) | kd ($s^{-1}$) | KD (nM) | Rmax (RU) | Chi$^2$ ($RU^2$) |
|---|---|---|---|---|---|---|
| chim 2A2 | 37.1 | 1.69E+06 | 9.68E-03 | 5.7 | 16.2 | 0.0437 |
| hu2A2-Q11 | 36 | 1.75E+06 | 1.73E-02 | 9.9 | 15 | 0.0216 |
| hu2A2-D23 | 38.2 | 1.72E+06 | 1.38E-02 | 8 | 14.5 | 0.0273 |
| hu2A2-D16 | 57.7 | 1.73E+06 | 1.89E-02 | 10.9 | 11.8 | 0.0143 |
| chim R11 | 29.1 | 9.57E+05 | 3.28E-03 | 3.4 | 10.1 | 0.0152 |
| huR11-Q11 | 44.9 | 8.21E+05 | 4.98E-03 | 6.1 | 13.4 | 0.0183 |
| huR11-Q12 | 50.3 | 7.33E+05 | 1.04E-02 | 14.2 | 13.6 | 0.00801 |
| huR11-D4 | 40.6 | 7.85E+05 | 7.10E-03 | 9 | 11.9 | 0.0101 |

TABLE 2

| Ligand | Ligand Level (RU) | ka ($M^{-1}s^{-1}$) | kd ($s^{-1}$) | KD (pM) | Rmax (RU) | Chi$^2$ ($RU^2$) |
|---|---|---|---|---|---|---|
| huR12_11 | 26.9 | 1.15E+06 | 9.65E-05 | 84 | 10.9 | 0.0157 |
| huR12_4 | 29.8 | 1.09E+06 | 9.93E-05 | 91 | 12.3 | 0.0339 |
| huR12_16 | 41 | 9.60E+05 | 8.79E-05 | 92 | 11.4 | 0.0174 |
| huR12_7 | 28.2 | 1.05E+06 | 1.16E-04 | 110 | 12.6 | 0.11 |
| huR12_14 | 38.7 | 7.91E+05 | 1.07E-04 | 136 | 14.6 | 0.0592 |
| huR12_1 | 36.9 | 5.80E+05 | 9.92E-05 | 171 | 11.7 | 0.00673 |
| huR12_5 | 51.7 | 6.83E+05 | 1.41E-04 | 206 | 14.6 | 0.0177 |
| huR12_13 | 54.1 | 5.12E+05 | 1.56E-04 | 304 | 13.6 | 0.00569 |
| R12 | 36.8 | 3.49E+05 | 3.61E-04 | 1030 | 13 | 0.0394 |

What is claimed is:

1. A humanized antibody, antibody derivative or antibody fragment retaining target binding capacity, which targets Receptor tyrosine kinase-like orphan receptor-1 (ROR1) and comprises three heavy chain CDR sequences consisting of amino acid sequences:
SEQ ID NO. 29 (CDR1 HC),
SEQ ID NO. 30 (CDR2 HC), and
SEQ ID NO. 31 (CDR3 HC), respectively,
and three light chain CDR sequences consisting of amino acid sequences:
SEQ ID NO. 32 (CDR1 LC),
SEQ ID NO. 33 (CDR2 LC), and
SEQ ID NO. 34 (CDR3 LC), respectively,
and which comprises a heavy chain variable region sequence that is at least 95% identical to a sequence selected from the group consisting of
SEQ ID NO. 37, SEQ ID NO. 39, SEQ ID NO. 41, and SEQ ID NO. 43, and
a light chain variable region sequence that is at least 95% identical to a sequence selected from the group consisting of SEQ ID NO. 38, SEQ ID NO. 40, SEQ ID NO. 42, and SEQ ID NO. 44.

2. The antibody, antibody derivative or antibody fragment according to claim 1, which comprises a heavy chain variable region sequence and a light chain variable sequence according to
SEQ ID NO. 37 and SEQ ID NO. 38, or
SEQ ID NO. 39 and SEQ ID NO. 40, or
SEQ ID NO. 41 and SEQ ID NO. 42, or
SEQ ID NO. 43 and SEQ ID NO. 44.

3. The antibody according to claim 2, wherein the antibody is selected from the group consisting of huR12-4, huR12-7, huR12-11, and huR12-16.

4. An Immunoligand-Drug Conjugate having the general formula A-(L)n-(T)m, in which
(a) A is a humanized antibody, wherein the antibody is selected from the group consisting of huR12-4, huR12-7, huR12-11, and huR12-16
(b) L is a linker, and
(c) T is a toxin
and in which n and m are integers between ≥1 and ≤10.

5. An Immunoligand-Drug Conjugate having the general formula A-(L)n-(T)m, in which
(a) A is a humanized anti-ROR-1 antibody,
wherein the humanized anti-ROR1 antibody comprises:
at least one heavy chain variable region that comprises a sequence selected from the group consisting of SEQ ID NO: 37, SEQ ID NO: 39, SEQ ID NO: 41, and SEQ ID NO: 43; and
at least one light chain variable region that comprises a sequence selected from the group consisting of SEQ ID NO: 38, SEQ ID NO: 40, SEQ ID NO: 42, and SEQ ID NO: 44,
(b) L is a linker, and
(c) T is a PNU-derived anthracycline,
in which amino acid sequences of A, of L, if comprising amino acids, and of T, if comprising amino acids, are from N-terminus to C-terminus, and in which n and m are integers between ≥1 and ≤10.

6. The Immunoligand-Drug Conjugate according to claim 5, wherein the antibody, antibody derivative or antibody fragment comprises a heavy chain variable region sequence and a light chain variable sequence according to
SEQ ID NO. 37 and SEQ ID NO. 38, or
SEQ ID NO. 39 and SEQ ID NO. 40, or
SEQ ID NO. 41 and SEQ ID NO. 42, or
SEQ ID NO. 43 and SEQ ID NO. 44.

7. The Immunoligand-Drug Conjugate according to claim 6, wherein the antibody is selected from the group consisting of huR12-4, huR12-7, huR12-11, and huR12-16.

8. A pharmaceutical composition comprising the Immunoligand-Drug Conjugate according to claim 5, together with one or more pharmaceutically acceptable ingredients.

* * * * *